(12) United States Patent
Webb et al.

(10) Patent No.: US 8,985,119 B1
(45) Date of Patent: Mar. 24, 2015

(54) METHOD AND APPARATUS FOR OPTICAL STIMULATION OF NERVES AND OTHER ANIMAL TISSUE

(75) Inventors: James S. Webb, Seattle, WA (US); Charles E. Hamilton, Kenmore, WA (US); Heather A. Ralph, Seattle, WA (US); Mark P. Bendett, Kirkland, WA (US); Charles A. Lemaire, Apple Valley, MN (US)

(73) Assignee: Lockheed Martin Corporation, Bethesda, MD (US)

(*) Notice: Subject to any disclaimer, the term of this patent is extended or adjusted under 35 U.S.C. 154(b) by 1293 days.

(21) Appl. No.: 12/797,544

(22) Filed: Jun. 9, 2010

Related U.S. Application Data

(62) Division of application No. 11/257,793, filed on Oct. 24, 2005, now Pat. No. 7,736,382.

(60) Provisional application No. 60/715,884, filed on Sep. 9, 2005.

(51) Int. Cl.
   *A61B 19/00* (2006.01)
   *A61N 5/06* (2006.01)

(52) U.S. Cl.
   USPC .................. 128/898; 607/88; 607/89; 606/15

(58) Field of Classification Search
   USPC .......... 607/88–96, 100, 108–110; 606/3, 4, 9, 606/15–18; 128/898
   See application file for complete search history.

(56) References Cited

U.S. PATENT DOCUMENTS

| | | | |
|---|---|---|---|
| 4,064,872 A | 12/1977 | Caplan |
| 4,232,678 A | 11/1980 | Skovajsa |
| 4,296,995 A | 10/1981 | Bickel |
| 4,558,703 A | 12/1985 | Mark |
| 4,596,992 A | 6/1986 | Hornbeck |

(Continued)

FOREIGN PATENT DOCUMENTS

| | | |
|---|---|---|
| WO | WO 0025112 | 5/2000 |
| WO | PCTUS0951080 | 11/2009 |
| WO | PCTUS0959591 | 11/2009 |

OTHER PUBLICATIONS

Augustine, George J., "Combining patch-clamp and optical methods in brain slices", "Journal of Neuroscience Methods", 1994, pp. 163-169, vol. 54.

(Continued)

*Primary Examiner* — Ahmed Farah
(74) *Attorney, Agent, or Firm* — Charles A. Lemaire; Jonathan M. Rixen; Lemaire Patent Law Firm, P.L.L.C.

(57) ABSTRACT

A nerve-stimulation device and method using light to provide a source of precise stimulation on one or more nerve fibers. In some embodiments, this simulation is provided through a device and method wherein a laser- or LED-light-generating source is operatively coupled to an optical fiber, which in turn is coupled to a plug in the end of a holder in a sheath. Light is then passed from the light source through the optical fiber to the holder and out a selected optical tip on the sheath to provide an efficacious amount of light to simulate nerves. In some embodiments, the device is constructed from non-magnetic material such as glass, plastic or ceramics. In some embodiments, the light emanating from the optical tip can be controlled manually or automatically. Some embodiments omit the fiber and use light directly from the laser diode.

21 Claims, 17 Drawing Sheets

(56) References Cited

U.S. PATENT DOCUMENTS

| | | |
|---|---|---|
| 4,671,285 A | 6/1987 | Walker |
| 4,681,791 A | 7/1987 | Shibahashi et al. |
| 4,724,835 A | 2/1988 | Liss et al. |
| 4,768,516 A | 9/1988 | Stoddart et al. |
| 4,813,418 A | 3/1989 | Harris |
| 4,840,485 A | 6/1989 | Gratton |
| 4,928,695 A | 5/1990 | Goldman et al. |
| 4,930,504 A | 6/1990 | Diamantopoulos et al. |
| 4,972,331 A | 11/1990 | Chance |
| 4,989,605 A | 2/1991 | Rossen |
| 5,062,428 A | 11/1991 | Chance |
| 5,088,493 A | 2/1992 | Giannini et al. |
| 5,122,974 A | 6/1992 | Chance |
| 5,139,025 A | 8/1992 | Lewis et al. |
| 5,150,704 A | 9/1992 | Tatebayashi et al. |
| 5,151,909 A | 9/1992 | Davenport et al. |
| 5,152,278 A | 10/1992 | Clayman |
| 5,187,672 A | 2/1993 | Chance et al. |
| 5,192,278 A | 3/1993 | Hayes et al. |
| 5,212,386 A | 5/1993 | Gratton et al. |
| 5,213,093 A | 5/1993 | Swindle |
| 5,213,105 A | 5/1993 | Gratton et al. |
| 5,257,202 A | 10/1993 | Feddersen et al. |
| 5,259,382 A | 11/1993 | Kronberg |
| 5,261,822 A | 11/1993 | Hall et al. |
| 5,323,010 A | 6/1994 | Gratton et al. |
| 5,327,902 A | 7/1994 | Lemmen |
| 5,353,799 A | 10/1994 | Chance |
| 5,386,827 A | 2/1995 | Chance et al. |
| 5,402,778 A | 4/1995 | Chance |
| 5,419,312 A | 5/1995 | Arenberg et al. |
| 5,430,175 A | 7/1995 | Hess et al. |
| 5,445,146 A | 8/1995 | Bellinger |
| 5,464,960 A | 11/1995 | Hall et al. |
| 5,480,482 A | 1/1996 | Novinson |
| 5,484,432 A | 1/1996 | Sand |
| 5,548,604 A | 8/1996 | Toepel |
| 5,553,614 A | 9/1996 | Chance |
| 5,564,417 A | 10/1996 | Chance |
| 5,608,519 A | 3/1997 | Gourley et al. |
| 5,664,574 A | 9/1997 | Chance |
| 5,704,899 A | 1/1998 | Milo |
| 5,754,578 A | 5/1998 | Jayaraman |
| 5,755,752 A | 5/1998 | Segal |
| 5,792,051 A | 8/1998 | Chance |
| 5,796,889 A | 8/1998 | Xu et al. |
| 5,799,030 A | 8/1998 | Brenner |
| 5,851,223 A | 12/1998 | Liss et al. |
| 5,899,865 A | 5/1999 | Chance |
| 5,913,884 A | 6/1999 | Trauner et al. |
| 6,033,431 A | 3/2000 | Segal |
| 6,048,359 A | 4/2000 | Biel |
| 6,066,127 A | 5/2000 | Abe |
| 6,074,411 A | 6/2000 | Lai et al. |
| 6,104,957 A | 8/2000 | Alo et al. |
| 6,110,195 A | 8/2000 | Xie et al. |
| 6,152,882 A | 11/2000 | Prutchi |
| 6,171,239 B1 | 1/2001 | Humphrey |
| 6,184,542 B1 | 2/2001 | Alphonse |
| 6,224,969 B1 | 5/2001 | Steenbergen et al. |
| 6,246,892 B1 | 6/2001 | Chance |
| 6,257,759 B1 | 7/2001 | Witonsky et al. |
| 6,258,082 B1 | 7/2001 | Lin |
| 6,263,221 B1 | 7/2001 | Chance et al. |
| 6,267,779 B1 | 7/2001 | Gerdes |
| 6,272,367 B1 | 8/2001 | Chance |
| 6,284,078 B1 | 9/2001 | Witonsky et al. |
| 6,294,109 B1 | 9/2001 | Ratna et al. |
| 6,301,279 B1 | 10/2001 | Garbuzov et al. |
| 6,310,083 B1 | 10/2001 | Kao et al. |
| 6,312,451 B1 | 11/2001 | Streeter |
| 6,314,324 B1 | 11/2001 | Lattner et al. |
| 6,330,388 B1 | 12/2001 | Bendett et al. |
| 6,339,606 B1 | 1/2002 | Alphonse |
| 6,353,226 B1 | 3/2002 | Khalil et al. |
| 6,358,272 B1 | 3/2002 | Wilden |
| 6,363,188 B1 | 3/2002 | Alphonse |
| 6,417,524 B1 | 7/2002 | Alphonse |
| 6,421,474 B2 | 7/2002 | Jewell et al. |
| 6,444,313 B1 | 9/2002 | Ono et al. |
| 6,456,866 B1 | 9/2002 | Tyler et al. |
| 6,459,715 B1 | 10/2002 | Khalfin et al. |
| 6,475,800 B1 | 11/2002 | Hazen et al. |
| 6,488,704 B1 | 12/2002 | Connelly et al. |
| 6,493,476 B2 | 12/2002 | Bendett |
| 6,505,075 B1 | 1/2003 | Weiner |
| 6,542,772 B1 | 4/2003 | Chance |
| 6,546,291 B2 | 4/2003 | Merfeld et al. |
| 6,556,611 B1 | 4/2003 | Khalfin et al. |
| 6,564,076 B1 | 5/2003 | Chance |
| 6,585,411 B2 | 7/2003 | Hammarth et al. |
| 6,585,722 B1 | 7/2003 | Abe |
| 6,592,611 B1 | 7/2003 | Zawada |
| 6,630,673 B2 | 10/2003 | Khalil et al. |
| 6,636,678 B1 | 10/2003 | Bendett et al. |
| 6,639,930 B2 | 10/2003 | Griffel et al. |
| 6,669,379 B2 | 12/2003 | Janosik et al. |
| 6,669,765 B2 | 12/2003 | Senga et al. |
| 6,688,783 B2 | 2/2004 | Janosik et al. |
| 6,690,873 B2 | 2/2004 | Bendett et al. |
| 6,735,474 B1 | 5/2004 | Loeb et al. |
| 6,735,475 B1 | 5/2004 | Whitehurst et al. |
| 6,744,548 B2 | 6/2004 | Abeles |
| 6,748,275 B2 | 6/2004 | Lattner et al. |
| 6,823,109 B2 | 11/2004 | Sasaki et al. |
| RE38,670 E | 12/2004 | Asah et al. |
| 6,836,685 B1 | 12/2004 | Fitz |
| 6,871,084 B1 | 3/2005 | Kingsley et al. |
| 6,902,528 B1 | 6/2005 | Garibaldi et al. |
| 6,909,826 B2 | 6/2005 | Cai et al. |
| 6,921,413 B2 | 7/2005 | Mahadevan-Jansen et al. |
| 6,956,650 B2 | 10/2005 | Boas et al. |
| 6,980,579 B2 | 12/2005 | Jewell |
| 6,989,023 B2 | 1/2006 | Black |
| 7,003,353 B1 | 2/2006 | Parkhouse |
| 7,004,645 B2 | 2/2006 | Lemoff et al. |
| 7,006,749 B2 | 2/2006 | Illich et al. |
| 7,031,363 B2 | 4/2006 | Biard et al. |
| 7,040,805 B1 | 5/2006 | Ou et al. |
| 7,068,878 B2 | 6/2006 | Crossman-Bosworth et al. |
| 7,069,083 B2 | 6/2006 | Finch |
| 7,079,900 B2 | 7/2006 | Greenburg et al. |
| 7,085,300 B2 | 8/2006 | Werner et al. |
| 7,095,770 B2 | 8/2006 | Johnson |
| 7,116,886 B2 | 10/2006 | Colgan et al. |
| 7,139,603 B2 | 11/2006 | Chance |
| 7,156,866 B1 | 1/2007 | Riggs et al. |
| 7,194,063 B2 | 3/2007 | Dilmanian et al. |
| 7,225,028 B2 | 5/2007 | Della Santina et al. |
| 7,231,256 B2 | 6/2007 | Wahlstrand et al. |
| 7,244,253 B2 | 7/2007 | Neev |
| 7,302,296 B1 | 11/2007 | Hoffer |
| 7,309,335 B2 | 12/2007 | Altshuler et al. |
| 7,311,722 B2 | 12/2007 | Larsen |
| 7,324,852 B2 | 1/2008 | Barolat et al. |
| 7,329,251 B2 | 2/2008 | Yamada et al. |
| 7,337,004 B2 | 2/2008 | Classen et al. |
| 7,355,155 B2 | 4/2008 | Wang |
| 7,391,561 B2 | 6/2008 | Di Teodoro et al. |
| 7,402,167 B2 | 7/2008 | Nemenov |
| RE40,587 E | 11/2008 | McKinnon |
| 7,647,112 B2 | 1/2010 | Tracey et al. |
| 7,654,750 B2 | 2/2010 | Brenner et al. |
| 7,787,170 B2 | 8/2010 | Patel et al. |
| 7,797,029 B2 | 9/2010 | Gibson et al. |
| 7,904,139 B2 | 3/2011 | Chance |
| 7,951,181 B2 | 5/2011 | Mahadevan-Jansen et al. |
| 8,078,263 B2 | 12/2011 | Zeman et al. |
| 2002/0002391 A1 | 1/2002 | Gerdes |
| 2002/0123781 A1 | 9/2002 | Shanks et al. |
| 2002/0147400 A1 | 10/2002 | Chance |
| 2003/0083724 A1 | 5/2003 | Jog et al. |
| 2003/0236458 A1 | 12/2003 | Hochman |
| 2004/0073101 A1 | 4/2004 | Chance |

(56) References Cited

U.S. PATENT DOCUMENTS

| | | |
|---|---|---|
| 2004/0116985 A1 | 6/2004 | Black |
| 2004/0225339 A1 | 11/2004 | Yaroslaysky et al. |
| 2004/0243111 A1 | 12/2004 | Bendett et al. |
| 2004/0243112 A1 | 12/2004 | Bendett et al. |
| 2005/0065531 A1 | 3/2005 | Cohen |
| 2005/0096720 A1 | 5/2005 | Sharma et al. |
| 2005/0099824 A1 | 5/2005 | Dowling et al. |
| 2005/0142344 A1 | 6/2005 | Toepel |
| 2005/0143789 A1 | 6/2005 | Whitehurst et al. |
| 2005/0169597 A1 | 8/2005 | Colgan et al. |
| 2005/0228256 A1 | 10/2005 | Labadie et al. |
| 2006/0095105 A1 | 5/2006 | Jog et al. |
| 2006/0129210 A1 | 6/2006 | Cantin et al. |
| 2006/0149337 A1 | 7/2006 | John |
| 2006/0155348 A1* | 7/2006 | deCharms .................. 607/89 |
| 2006/0161218 A1 | 7/2006 | Danilov |
| 2006/0161227 A1 | 7/2006 | Walsh et al. |
| 2006/0167564 A1 | 7/2006 | Flaherty et al. |
| 2006/0276861 A1 | 12/2006 | Lin |
| 2007/0053996 A1 | 3/2007 | Boyden et al. |
| 2007/0054319 A1 | 3/2007 | Boyden et al. |
| 2007/0060983 A1 | 3/2007 | Merfeld |
| 2007/0060984 A1 | 3/2007 | Webb et al. |
| 2007/0142874 A1 | 6/2007 | John |
| 2007/0179557 A1 | 8/2007 | Maschino et al. |
| 2007/0261127 A1 | 11/2007 | Boyden et al. |
| 2008/0009748 A1 | 1/2008 | Gratton et al. |
| 2008/0077198 A1 | 3/2008 | Webb et al. |
| 2008/0077200 A1 | 3/2008 | Bendett et al. |
| 2008/0086206 A1 | 4/2008 | Nasiatka et al. |
| 2008/0140149 A1 | 6/2008 | John et al. |
| 2008/0161697 A1 | 7/2008 | Chance |
| 2009/0030327 A1 | 1/2009 | Chance |
| 2009/0069863 A1* | 3/2009 | Pless et al. .................. 607/45 |
| 2009/0076115 A1 | 3/2009 | Wharton et al. |
| 2009/0163982 A1 | 6/2009 | deCharms |
| 2009/0177255 A1 | 7/2009 | Merfeld |
| 2010/0280571 A1* | 11/2010 | Sloan ............................. 607/45 |

OTHER PUBLICATIONS

Banghart, Matthew, et al., "Light-activated ion channels for remote control of neuronal firing", "Nature Neuroscience", Nov. 21, 2004, pp. 1381-1386, vol. 7, No. 12.
Boyden, Edward S., et al., "Millisecond-timescale, genetically targeted optical control of neural activity", "Nature Neuroscience ", Sep. 2005, pp. 1263-1268, vol. 8, No. 9.
Bureau, Ingrid, et al., "Precise Development of Functional and Anatomical Columns in the Neocortex", "Neuron", Jun. 10, 2004, pp. 789-801, vol. 42.
Deal, Walter J., et al., "Photoregulation of Biol. Activity by Photochromic Reagents, 3. Photoreg. of Bioelectricity by Acetylcholine Receptor INH", "Proc. Natl. Acad. Sci.", 1969, pp. 1230-1234, vol. 64, No. 4.
Dodt, H.-U., et al., "Circuitry of rat barrel cortex investigated by infrared-guided laser stimulation", "NeuroReport", Mar. 24, 2003, pp. 623-627, vol. 14, No. 4.
Dodt, H.-U., et al., "Precisely Localized LTD in the Neocortex Revealed by Infrared-Guided Laser Stimulation.", "Science ", Oct. 1, 1999, pp. 110-113, vol. 286.
Eder, Matthias, et al. , "Neocortical Long-Term Potentiation and Long-Term Depression: Site of Expression Investigated by IR-Guided Laser Stim.", "Journal of Neuroscience", Sep. 1, 2002, pp. 7558-7568, vol. 22, No. 17.
Naples, et al., "A spiral nerve cuff electrode for peripheral nerve stimulation", "IEEE Trans Biomed Eng", Nov. 1988, pp. 905-916, vol. 35, No. 11.
Vogel, Alfred, et al., "Mechanisms of pulsed laser ablation of biological tissues.", "Chemical Reviews", 2003, pp. 577-644, vol. 103, No. 2.

Wells, Jonathon, et al., "Optical stimulation of neural tissue in vivo", "Optics Letters", Mar. 1, 2005, pp. 504-506, vol. 30, No. 5.
Yoo, et al., "Selective recording of the canine hypoglossal nerve using a multicontact flat interface nerve electrode", "IEEE Trans Biomed Eng", Aug. 2005, pp. 1461-1469, vol. 52, No. 8.
Zemelman, Boris V., et al. , "Photochemical gating of heterologous ion channels: Remote control over genetically designated populations of neurons", "Proceedings of the National Academy of Sciences", Feb. 4, 2003, pp. 1352-1357, vol. 100, No. 3.
Allegre, et al., "Stimulation in the rat of a nerve fiber bundle by a short UV pulse from an excimer laser", "NeuroScience Letters", 1994, pp. 261-264, vol. 180.
Arridge, et al., "The theoretical basis for the determination of optical pathlengths in tissue: temporal and frequency analysis", "Phys. Med. Biol.", 1992, pp. 1531-1560, vol. 37.
Chance, et al., "Comparison of time-resolved and -unresolved measurements of deoxyhemoglobin in brain", "Proc. Nati. Acad. Sci. USA", Jul. 1988, pp. 4971-4975, vol. 85.
Desmurget, et al., "Movement Intention after Parietal Cortex Stimulation in Humans", "Science", May 8, 2009, pp. 811-813, vol. 324.
Fork, Richard L., "Laser Stimulation of Nerve Cells in Aplysia", "Science, New Series", Mar. 5, 1971, pp. 907-908, vol. 171, No. 3974.
Haggard, "The Sources of Human Volition", "Science", May 8, 2009, pp. 731-733, vol. 324.
Izzo, et al., "Laser Stimulation of the Auditory Nerve", "Lasers in Surgery and Medicine", 2006, Publisher: Wiley-Liss, Inc.
Izzo, et al., "Selectivity of neural stimulation in the auditory system: an comparison of optic and electric stimuli", "Journal of Biomedical Optics", Mar./Apr. 2007, pp. 021008 , vol. 12, No. 2.
Izzo, Agnella D., et al., "Optical Parameter Variability in Laser Nerve Stimulation: A Study of Pulse Duration, Repetition Rate, and Wavelength.", "IEEE Transactions on Biomedical Engineering", Jun. 2007, p. 1108-1114, vol. 54, No. 6(1).
Maiorov, M., et al., "218 W quasi-CW operation of 1.83 um two-dimensional laser diode array", "Electronics Letters", Apr. 15, 1999, pp. 636-638, vol. 35, No. 8.
Nakagawa, Atsuhiro, et al., "Pulsed holmium:yttrium-aluminum-garnet laser-induced liquid jet as a novel dissection device in neuroendoscopic surgery", "J. Neurosurg.", Jul. 2004 , pp. 145-150, vol. 101.
Passos, D., et al., "Tissue phantom for optical diagnostics based on a suspension of microspheres with a fractal size distribution", "Journal of Biomedical Optics.", Nov.-Dec. 2005 , pp. 064036, vol. 10, No. 6.
Princeton Lightwave , "High Power Multimode Laser Arrays", "www.princetonlightwave.com/content/pli_high_power_multimode_laser_arrays.pdf", 2005.
Princeton Lightwave , "High Power Water Cooled Laser Stack", "http://www.princetonlightwave.com/content/pli_high_power_multimode_laser_stacks.pdf", 2005 (downloaded 12.
Princeton Lightwave, "High Power Single Element Laser", "www.princetonlightwave.com/content/HP%20Single%20Element%20Laser%20version%202.pdf", 2005.
Rolfe, "In Vivo Near-Infrared Spectroscopy", "Annu. Rev. Biomed. Eng.", 2000, pp. 715-754 , vol. 2.
Schwartz, et al., "Auditory Brainstem Implants", "Neurotherapeutics: The Journal of the American Society for Experimental NeuroTherapeutics", Jan. 2008, pp. 128-136, vol. 5.
Tarler, et al., "Comparison of joint torque evoked with monopolar and tripolar-cuff electrodes", "IEEE Trans Neural Syst Rehabil Eng", 2003, pp. 227-235, vol. 11, No. 3.
Teudt, et al., "Optical Stimulation of the Facial Nerve: A New Monitoring Technique?", "The Laryngoscope", 2007, pp. 1641-1647, vol. 117, No. 9.
Wells, Jonathon, et al., "Application of Infrared Light for in vivo Neural Stimulation.", "Journal of Biomedical Optics", Nov. 2005, pp. 064003-1 to 064003-12, vol. 10, No. 6.
Moller, et al., "Intraoperative Neurophysiologic Monitoring", "American Journal of Otology", Jan. 1995, pp. 115-117, vol. 16, No. 1.

* cited by examiner

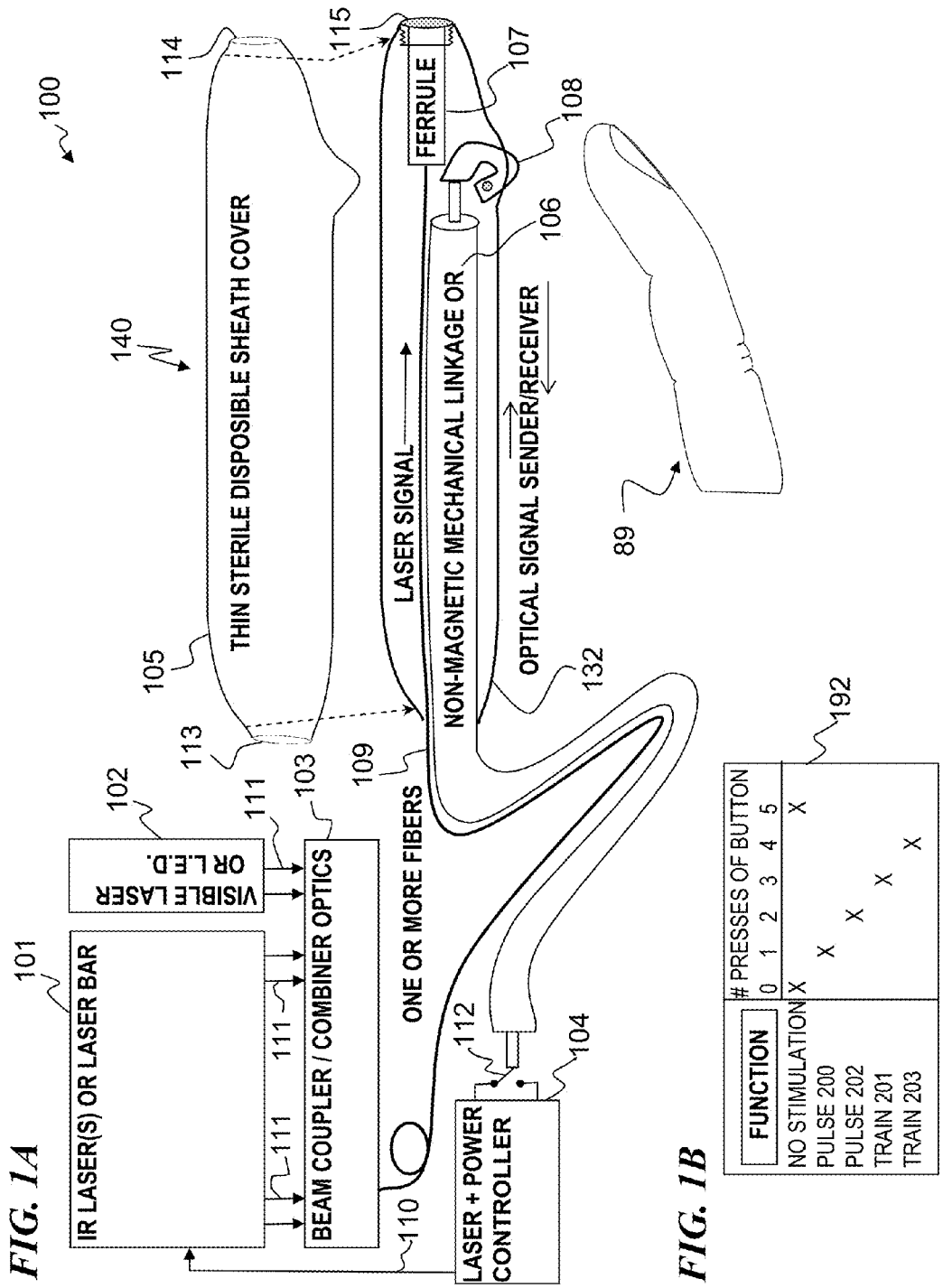

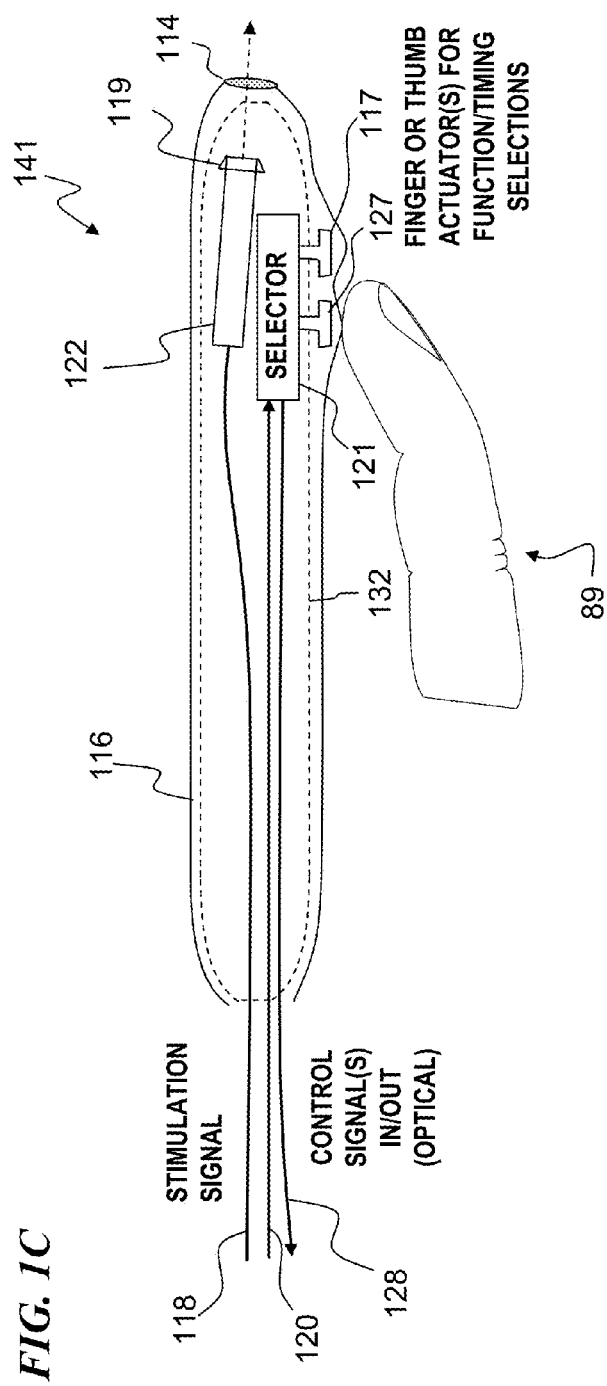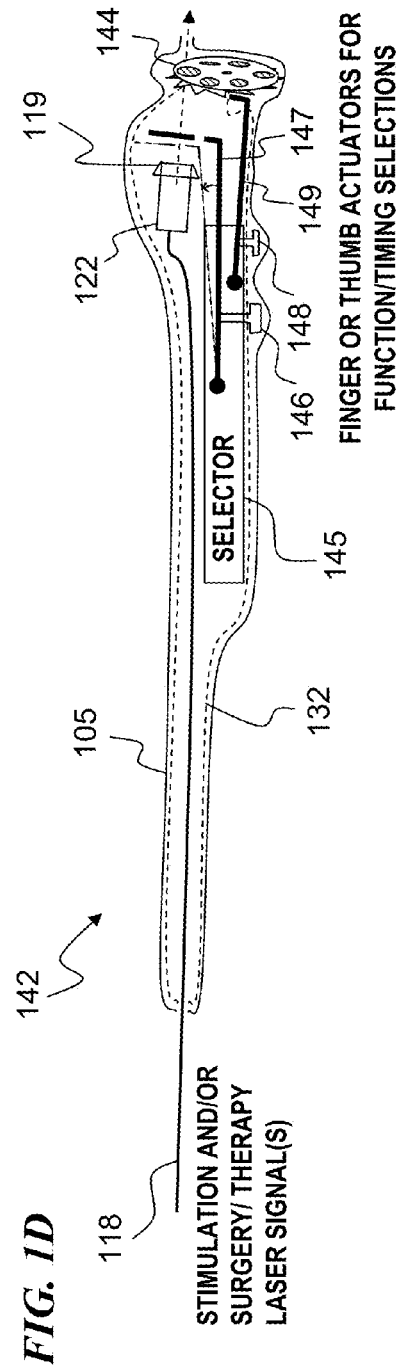

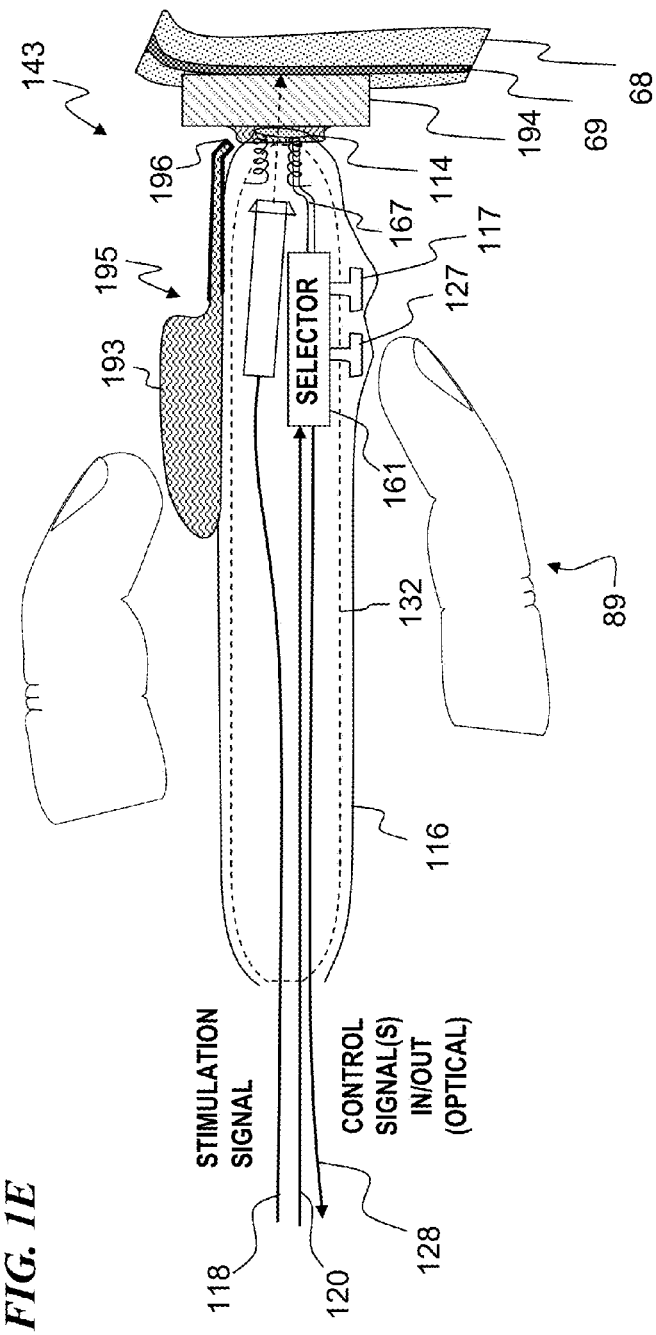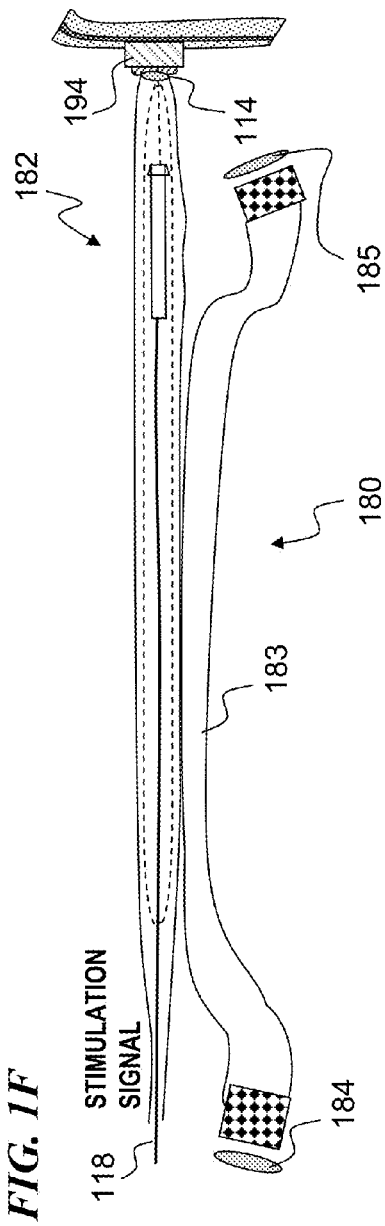

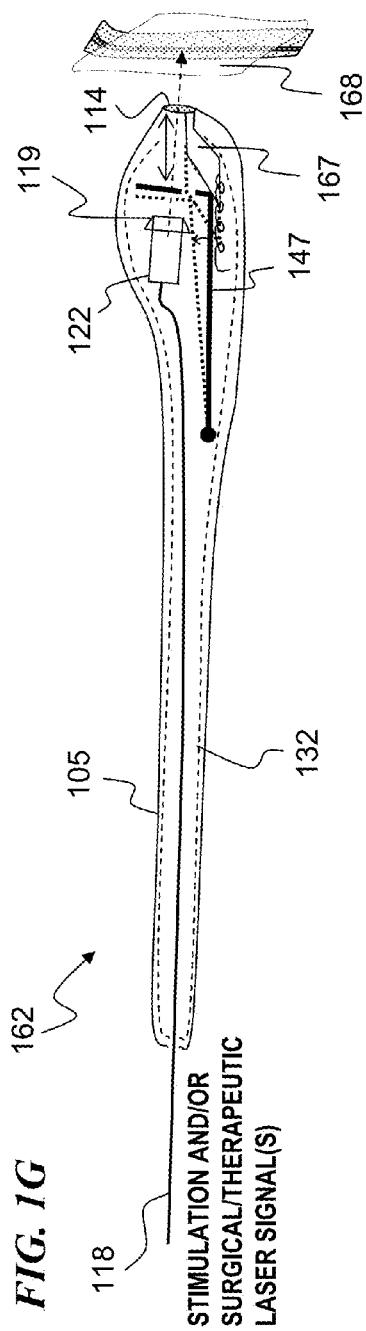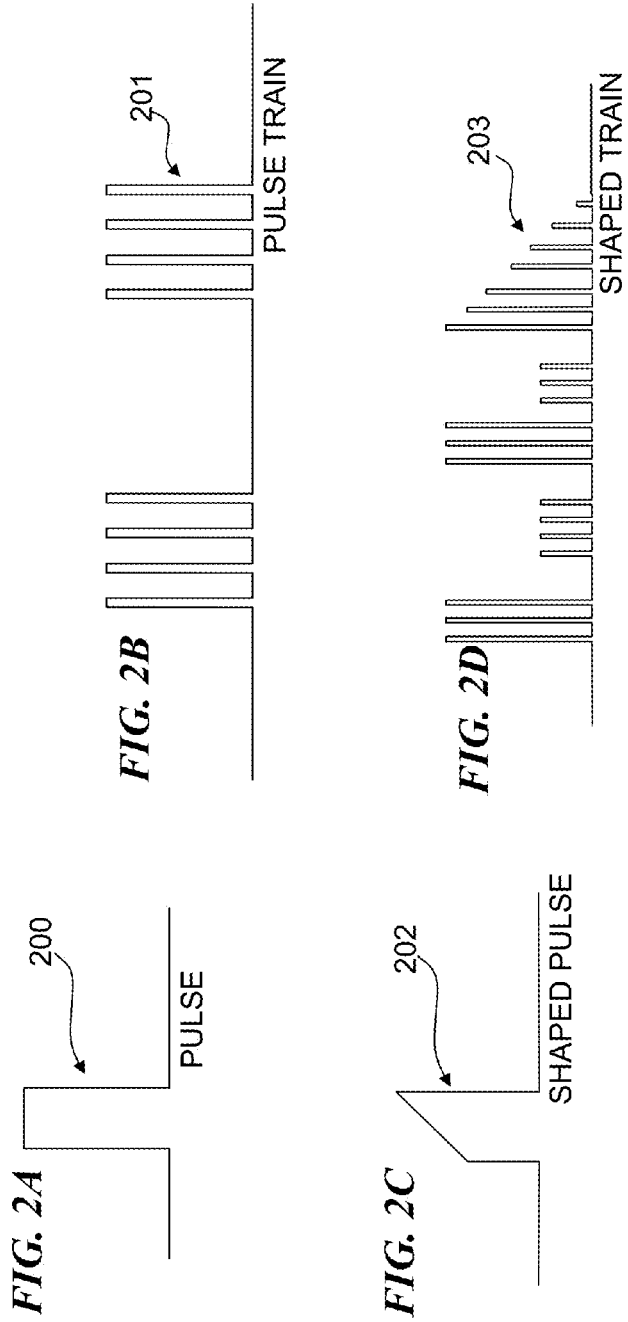

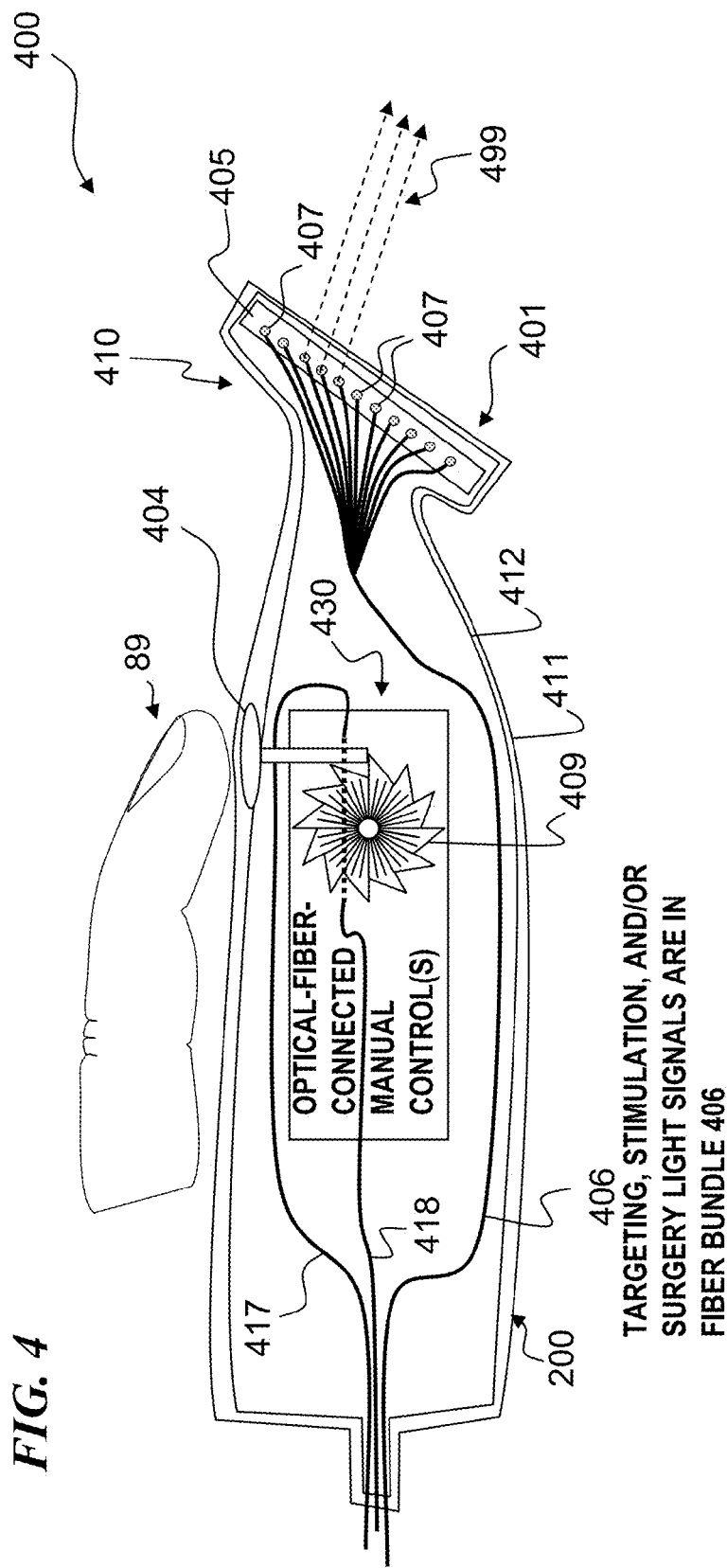

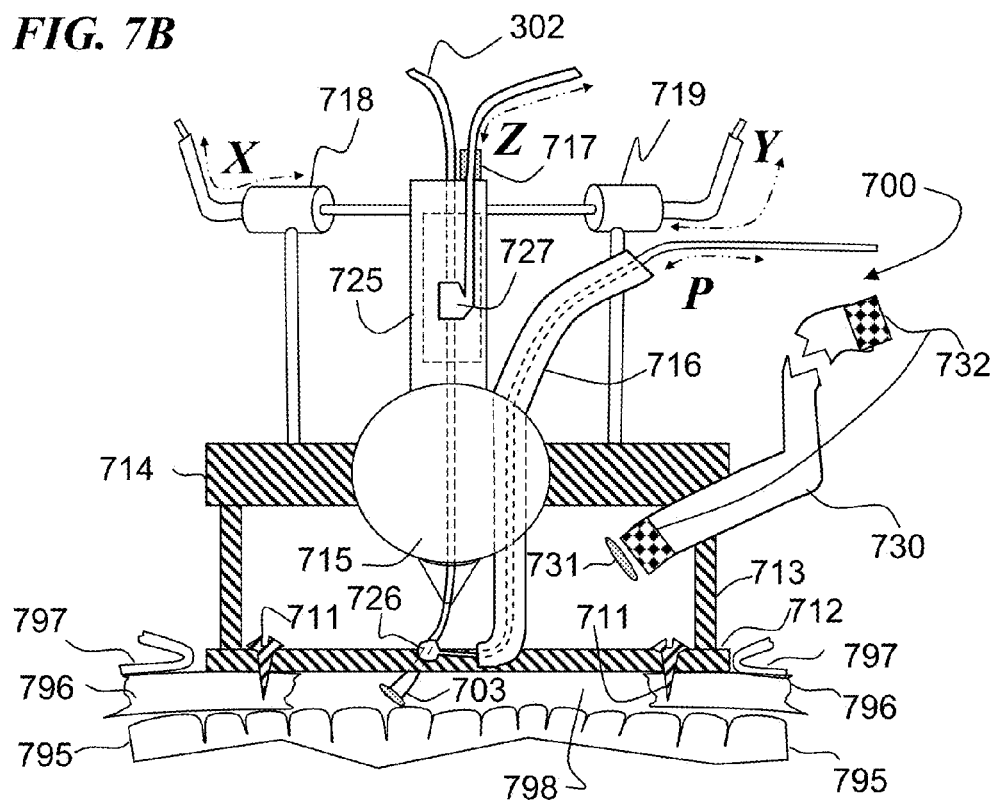

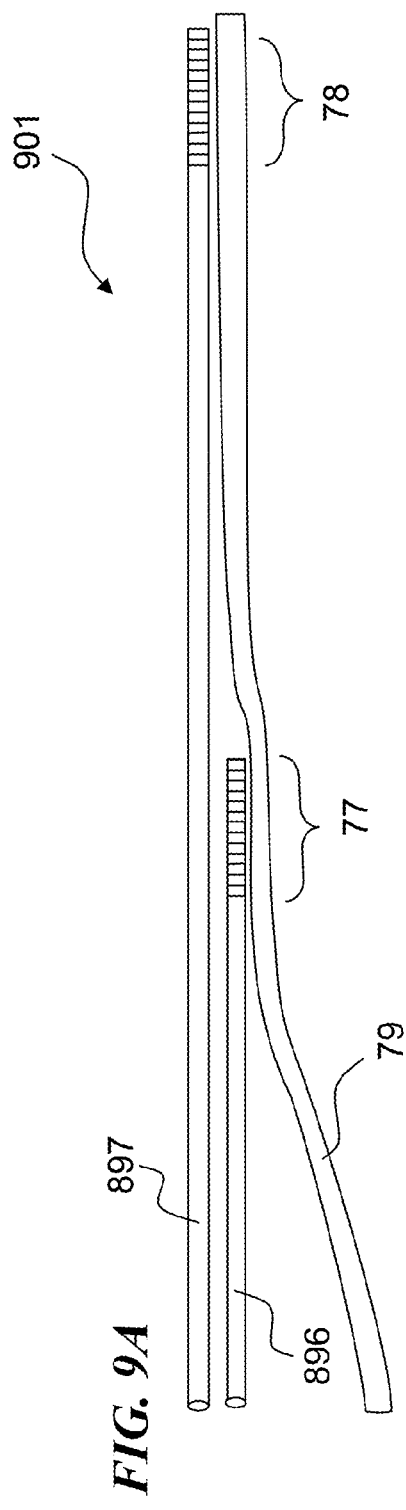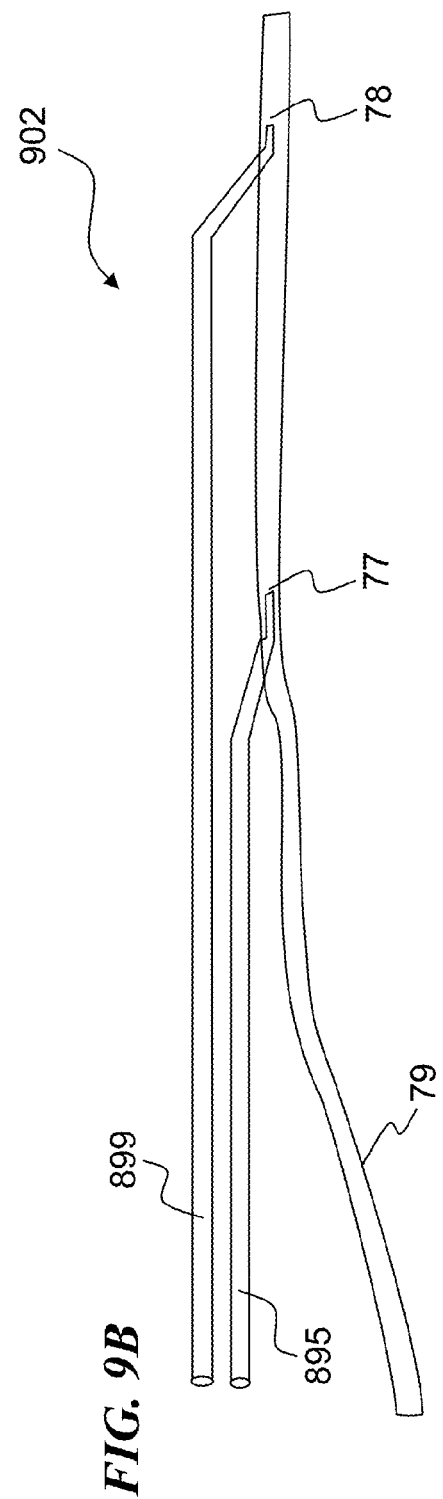

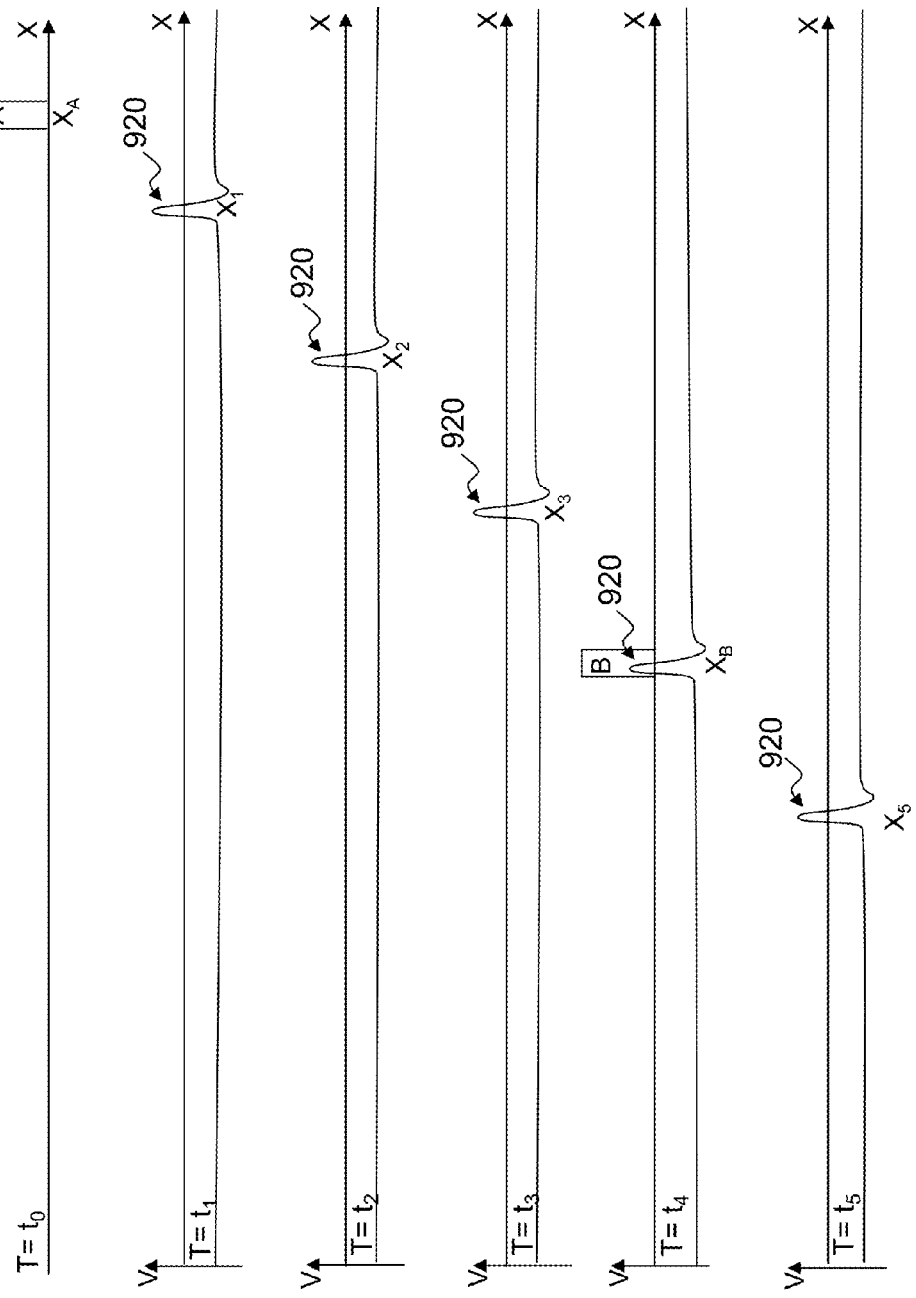

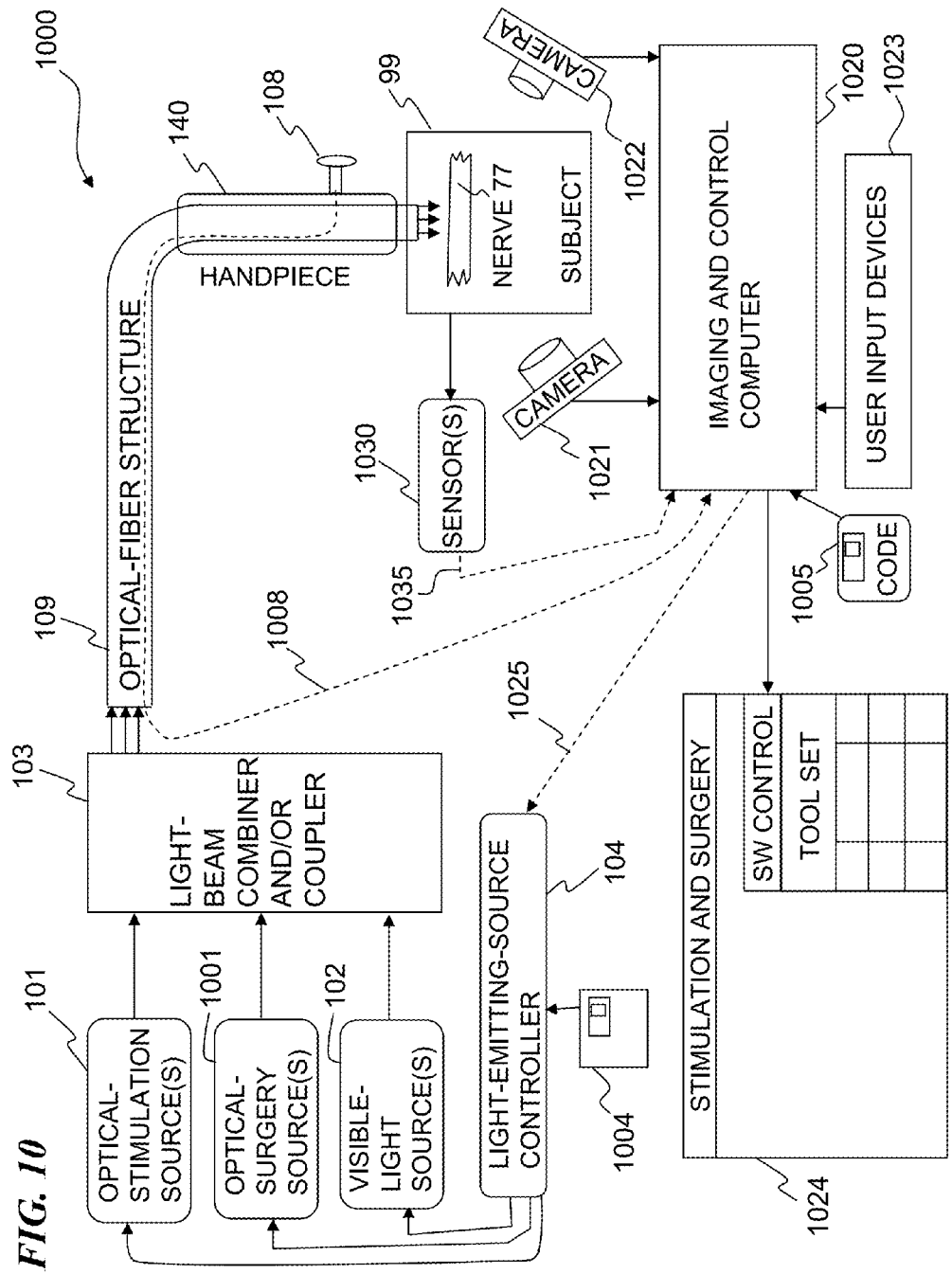

METHOD AND APPARATUS FOR OPTICAL STIMULATION OF NERVES AND OTHER ANIMAL TISSUE

CROSS-REFERENCE TO RELATED APPLICATIONS

This application is a divisional of U.S. patent application Ser. No. 11/257,793 filed on Oct. 24, 2005, titled "APPARATUS AND METHOD FOR OPTICAL STIMULATION OF NERVES AND OTHER ANIMAL TISSUE" (which issued as U.S. Pat. No. 7,736,382 on Jun. 15, 2010), which claimed benefit of U.S. Provisional Patent Application No. 60/715,884 filed Sep. 9, 2005, titled "APPARATUS AND METHOD FOR OPTICAL STIMULATION OF NERVES," each of which is incorporated herein by reference in its entirety.

FIELD OF THE INVENTION

The invention relates generally to optical nerve stimulation, and more particularly to methods and apparatus to generate, direct, and control the optical signal used to stimulate nerves and other animal tissue, and in particular, neural tissue.

BACKGROUND OF THE INVENTION

A nerve can be stimulated in a number of different ways, including electrical, mechanical, thermal, chemical, and now optical. A nerve is a filament of neural tissue composed of cells each having a cell body and one or more axons and dendrites. The axons extend peripherally as either myelinated or unmyelinated fibers. A chain of Schwann cells surrounds each myelinated nerve fiber with a multilayered myelin sheath. Groups of unmyelinated fibers are associated with single Schwann cells. Both types of nerve fibers are bound by endoneurium to form bundles, or fascicles. A perineurial membrane surrounds each fascicle. Groups of fascicles are held together by internal and external epineurium to form the peripheral nerves. The cell body of a motor neuron lies in the anterior horn of the spinal cord, while the cell body of a sensory neuron is located in the dorsal root ganglion, near the cord. (Christine Cheng; See *Nerve Compression Syndromes of the Upper Limb*, by Martin Dunitz, published by Taylor & Francis Group, 2002.)

Functional magnetic-resonance-imaging (fMRI) systems use extremely strong magnetic fields in generating images of an animal subject (e.g., a human) to discern functions and abnormalities of various portions of the body, and in particular, of the brain (e.g., during various mental activities or thought patterns). The high static magnetic fields ($B_0$ fields) created by an MRI machine create a danger of projectile accidents from any object having magnetic properties that may be near the MRI machine. Using metal probes to deliver electrical stimulation to nerves of a subject poses one such danger. It would be desirable to stimulate a nerve without using metal probes.

Further, it is desirable to cause a controlled stimulation of individual nerves. U.S. Pat. No. 6,921,413 issued to Mahadevan-Jansen et al. on Jul. 26, 2005, and titled "Methods and devices for optical stimulation of neural tissues," is incorporated herein by reference. Mahadevan-Jansen et al. note that traditional methods of stimulation include electrical, mechanical, thermal, and chemical. A neuron will propagate an electrical impulse (a nerve action potential) in response to a stimulus. The most common form of applying such stimulation is to form a transient current or voltage pulse applied through electrodes. Electrical, mechanical, and chemical stimulations have many limitations. To name a few, stimulation by such methods typically results in non-specific stimulation of neurons and/or damage to neurons. Difficulty exists in recording electrical activity from the neuron due to an electrical artifact created by the stimulus. To stimulate only one or a few neurons, fragile micro-electrodes need to be fashioned and carefully inserted into the tissue to be stimulated. Such techniques do not easily lend themselves to implantable electrodes for long-term use in stimulation of neural tissue. Mahadevan-Jansen et al. describe the use of low-power light from a free-electron laser (FEL) for optically stimulating selected individual nerve cells in vivo, while at the same time not stimulating neighboring cells with the laser light. Unfortunately, FELs are expensive, large, awkward and unwieldy.

Further, conventional optical systems include some magnetic materials, making them unsuitable for use near MRI systems.

In view of shortcomings in such conventional devices, there is a need for devices and methods that can provide inexpensive, compact, non-magnetic, and/or easy-to-use optical stimulation of nerves.

BRIEF SUMMARY OF THE INVENTION

In some embodiments, the invention provides a method and apparatus for stimulating nerves using either an infra-red (IR) diode laser or light-emitting diode (LED) (e.g., one running at a wavelength of about 1.87 microns) or a diode-pumped solid-state laser running at a wavelength of 2.1 microns (e.g., a 785-micron-wavelength laser diode pumping a Tm/Ho solid-state crystal or fiber), or a laser diode operating at a wavelength of between about 1.8 and about 2.2 microns, with a fiber light-pen, pointer and/or wand that can be used to control, direct and/or shutter the light in a non-magnetic apparatus. In some embodiments, a laser diode is used to obtain power into an optical fiber that is sufficient to optically stimulate the nerve. In other embodiments, one or more LEDs, one or more lasers, or a combination of one or more LEDs and one or more lasers is used to obtain the stimulation light.

In some embodiments, either sharing a single optical fiber or passing in one or more separate fibers next to the optical fiber that carries the IR nerve-stimulation laser signal, the invention also includes a visible laser or LED signal that illuminates and points out the nerve being stimulated, and/or a high-power surgical and/or therapeutic laser signal that is used in conjunction with the IR nerve-stimulation signal. For example, in some embodiments, a visible laser is shined down an optical fiber to point out to the surgeon where the IR nerve-stimulation laser signal will be applied; the surgeon then activates the IR nerve-stimulation laser signal and observes the response (for example, phantom-limb pain of an amputee); and once the observed response determines the nerve location to be treated, the surgical and/or therapeutic laser signal is applied to that location.

The present invention, with its ability to precisely stimulate a single nerve or a very small area of a brain with no metal or magnetic material near the subject, who, in some embodiments, may be a human patient requiring medical care, is a gateway technology that opens broad areas of medicine and surgery. In some embodiments, an enlarged digital or video image of the surgery site is displayed, and as the surgeon optically stimulates the various nerves or areas, the image is annotated (e.g., color-coded as a map of nerve function) to provide a record of which response was observed for each of the different areas stimulated. In some embodiments, once the annotated map is sufficiently complete, the surgeon can input graphical annotation to the computer identifying the extent or the exact area to which treatment is to be permitted, the visible signal (showing where the fiber is pointing) is inputted and compared to the map, such that the controller allows the surgical and/or therapeutic laser signal to be applied only to the identified allowed area.

As used herein, "optical stimulation of nerves" refers to stimulation caused by impinging light onto nerve tissue, regardless of the wavelength of the light (ultraviolet, visible, or infrared, wherein the term "light" is not necessarily restricted to light in the visible range of 400- to 700-nanometer wavelengths). The nerve being stimulated can be any nerve, such as motor or sensory nerves in the peripheral nervous system, nerve tissue of the central nervous system (nerves within the brain and spinal cord), the cranial nerves (e.g., the optic nerve, the olfactory nerve, the auditory nerve, and the like), the autonomic nervous system, as well as brain tissue and/or any other neural tissue. Thus, the tissue to which optical stimulation is applied need not itself be a "nerve" as conventionally defined, but could include brain tissue that when stimulated by light initiates a response similar to that carried by a nerve, e.g., an action potential that includes electrical and/or chemical components, and which is propagated to a location some distance from the point that was optically stimulated. As used herein, the term "subject" is an inclusive term that refers to any animal whose nerves may be stimulated by light, as the term light has been defined above; this includes non-mammalian and mammalian species, including humans, and including especially humans who may be patients receiving professional medical care. As used herein, the term "optical-fiber structure" is an inclusive term that includes a single optical fiber as well as a bundle of individual optical fibers, a fused bundle of optical fibers, star couplers, and depending on the context optionally includes ferrules, lenses, and the like used to couple light into and out of the optical fiber structure.

In some embodiments, the present invention includes at least some of the following: a first light-emitting source, a second light-emitting source, a light-beam combiner, a mechanical linkage with a trigger mechanism, a ferrule, a light-emitting-source controller, and a disposable sheath. In some embodiments, the sheath includes a lens or other optics to focus the light from the fiber to a particular spot size and/or shape. In some embodiments, a plurality of different interchangeable sheaths are provided, each having a different spot size and/or shape, allowing the surgeon to choose the appropriate light pattern, and/or to change the light pattern based on results of the first-tried sheath's light pattern and the patient response obtained.

In some embodiments, a method is practiced by generating a first laser using a first light-emitting source, generating a second laser using a second light-emitting source, transmitting the first and second laser to a beam-combiner optic using a first optical-fiber structure, transmitting the first and second laser light from the beam-combiner optic to a ferrule using a second optical-fiber structure, emitting the first and second laser light from the ferrule, regulating the first and second laser light using a mechanical linkage operatively coupled to a light-emitting-source controller; and connecting the light-emitting-source controller to the first light-emitting source via a bus.

In some embodiments, the present invention includes an apparatus having a finger-and/or-thumb control, a ferrule, a first optical-fiber structure, a second optical-fiber structure, and a disposable sheath. This apparatus is used to deliver an efficacious amount of, in some embodiments, visible and infra-red (IR) light so as to target and stimulate nerve tissue.

In some embodiments, an apparatus is constructed of an optical stimulator, a first optical-fiber structure, a radio-frequency (RF) charger, and a radio remote programmer. In some embodiments, this optical stimulator is implanted into a recipient to provide an efficacious dose of light to promote nerve stimulation. In some embodiments, the stimulation light is IR (infrared), while in other embodiments, visible light, ultraviolet, or combinations of a plurality of wavelengths are used.

In some embodiments, a method is practiced involving charging an RF recharger, supplying a charge to a battery from the RF charger, powering a controller with the battery, powering a first light source, powering a second light source, emitting light from the first light source, emitting light from the second light source, controlling the light from the first and second light sources using a radio remote programmer, combining the light from the first and second light sources via a combiner, and transmitting the combined light via an optical structure to a nerve fiber.

In some embodiments, the invention includes a kit containing a first light-emitting source, a second light-emitting source, a light-beam combiner, a mechanical linkage with a trigger mechanism, a ferrule, a light-emitting-source controller, and an optional disposable sheath. Also contained in this kit are the various materials needed to assemble the apparatus.

BRIEF DESCRIPTION OF THE DRAWINGS

FIG. 1A is a block diagram 100 of a first laser device using a mechanical trigger mechanism.

FIG. 1B is a table showing the function-selection state machine changes obtained by successive presses of an optical-stimulation function-selection button 127 shown in FIG. 1C.

FIG. 1C is a block diagram of a laser device 141 using a manually controlled selector implementing a finger or thumb control.

FIG. 1D is a block diagram of a laser device 142 using a manually controlled selector implementing a finger or thumb control for local mechanical control of the stimulation light.

FIG. 1E is a block diagram of a laser device 143 having a mister 195 and/or focus plate 194.

FIG. 1F is a block diagram of an apparatus that includes an elongated endoscope structure 180 and a nerve-stimulation structure 182.

FIG. 1G is a block diagram of a laser device 162 using a spring-loaded-tip controlled selector 167 for local mechanical control of the stimulation light.

FIG. 2A is a diagram 200 of a single light pulse as would be typically emitted using a manually controlled shutter or aperture.

FIG. 2B is a diagram 201 of a pulse train as would be generated when a light pulse device is operatively coupled and used with light source.

FIG. 2C is a diagram 202 of a shaped pulse as would be generated when a light pulse device is operatively coupled and used with light source.

FIG. 2D is a diagram 203 of a shaped train pulse as would be generated when a light pulse device is operatively coupled and used with light source.

FIG. 4 is a block diagram of a light-delivery device 400 using a manually controlled selector and delivery system of laser light.

FIGS. 7A, 7B, and 7C are perspective-, side-, and top-view block diagrams of a light-delivery device 700 using a remotely controlled fiber holder affixed to a subject for nerve stimulation using laser light.

FIG. 9A is a schematic diagram of an optical-fiber light-delivery device 901 using a grating on each of two fibers to direct light over a line at two locations along a nerve 79.

FIG. 9B is a schematic diagram of an optical-fiber light-delivery device 902 using a polished end on each of two fibers to direct light to points at two locations along a nerve 79.

FIG. 9C is a series of timing diagrams showing reinforced stimulation of an action potential along a nerve.

FIG. 10 is a schematic diagram of an optical fiber light-delivery system 1000.

DETAILED DESCRIPTION OF THE INVENTION

Figure 3A:
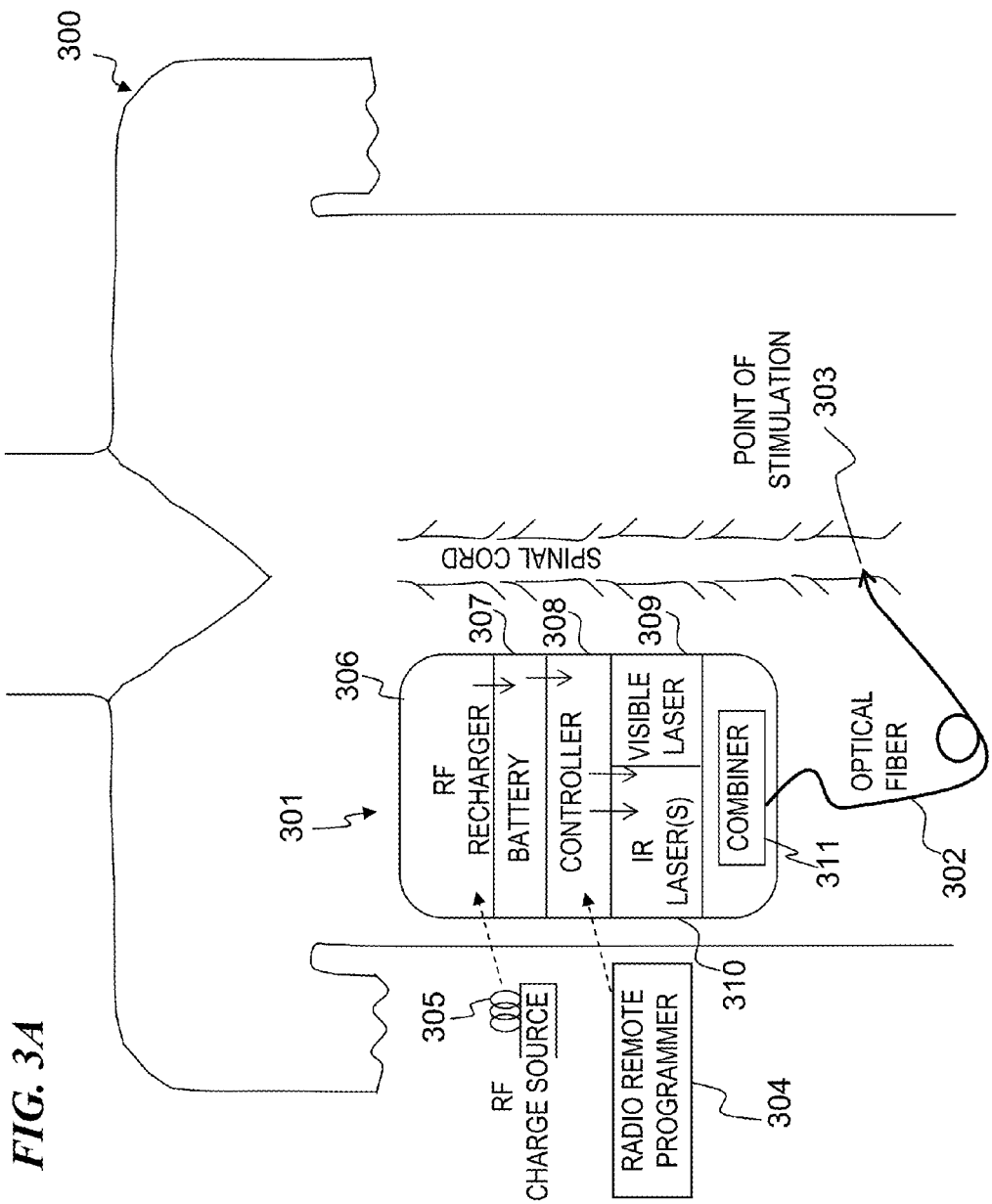
FIG. 3A is a schematic 300 detailing an implantable version of the device that is powered and controlled via an external source.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

CNAP is an abbreviation for compound nerve action potential. CMAP is an abbreviation for compound muscle action potential. As used herein "target neural tissue" is defined as any neural tissue including, but not limited to, peripheral nerves, spinal-cord tissue, and brain tissue of animals, including mammals, and specifically including humans. As used herein "electrical impulse" is defined an electrical current applied to the nerve to initiate an action potential in the neuron. As used herein "stimulation effect" is defined as propagation of an electrical signal within or along neural or muscular tissue. As used herein "single nerve fiber" is defined as a portion of a neuron, namely the axon, which carries action potentials from the cell body to the axon terminal at a synapse, or one or more of the dendrites, which accumulate signals from one or more sources and carry these to the cell body. Many nerve fibers compose a peripheral nerve, such as the sciatic nerve of a leopard frog (*Rana Pepiens*) or a mammal.

For ease of explanation and conciseness, the present invention is described as embodiments of an apparatus and method for optically stimulating nerves and/or generating nerve action potentials. CNAP is one form of nerve action potential. In other embodiments of the invention, substantially similar apparatus and methods are used for optical stimulation of other tissues, such as muscles and/or generating muscle action potentials. CMAP is one form of muscle action potential.

As used herein "hand operated" means operated by some portion of a user's hand or hands, including by one or more of the fingers, thumb, wrist and palm of the hand, or of both hands. In some embodiments, a light-delivery handpiece is hand operated to the extent that the location (i.e., on the nerve or neural tissue) to which light is delivered is determined by positioning the handpiece by hand. In some embodiments, a light-delivery handpiece is also hand operated in that a control device (such as a button, wheel, trigger, iris, shutter, and the like) is operated by hand to control the type of stimulation light (e.g., pulses, intensity, wavelength, pulse train, and the like) and/or timing of the stimulation light.

As used herein "one micron" is defined 1.0 micrometer. As used herein "a spot size of d1 microns to d2 microns," where d1 and d2 are numbers, is synonymous with "an area of a circle or other shape with a diameter in a range of from d1 micrometers to d2 micrometers," as is known to people skilled in the art. For example, a spot size in a range of 200 microns to 600 microns is synonymous with an area (e.g., of a circle) with a diameter in a range of from 200 micrometers to 600 micrometers, corresponding to an area with a size in a range of about 31,416 square microns to about 282,743 square microns, using the formula of Area=$\frac{1}{4}\pi D^2$. In some embodiments, a spot is generated by passing the light that exits an end of an optical fiber through a lens, holographic imaging pattern, or other imaging apparatus.

In other embodiments, spots with diameters of 1 micrometer or smaller to 1000 micrometers (1 mm) or larger are used; for example, about 5 micrometers, about 10 micrometers, about 15 micrometers, about 20 micrometers, about 25 micrometers, about 30 micrometers, about 35 micrometers, about 40 micrometers, about 45 micrometers, about 50 micrometers, about 55 micrometers, about 60 micrometers, about 65 micrometers, about 70 micrometers, about 75 micrometers, about 80 micrometers, about 85 micrometers, about 90 micrometers, about 95 micrometers, about 100 micrometers, about 110 micrometers, about 120 micrometers, about 130 micrometers, about 140 micrometers, about 150 micrometers, about 160 micrometers, about 170 micrometers, about 180 micrometers, about 190 micrometers, about 200 micrometers, about 210 micrometers, about 220 micrometers, about 230 micrometers, about 240 micrometers, about 250 micrometers, about 260 micrometers, about 270 micrometers, about 280 micrometers, about 290 micrometers, about 300 micrometers, about 310 micrometers, about 320 micrometers, about 330 micrometers, about 340 micrometers, about 350 micrometers, about 360 micrometers, about 370 micrometers, about 380 micrometers, about 390 micrometers, about 400 micrometers, about 410 micrometers, about 420 micrometers, about 430 micrometers, about 440 micrometers, about 450 micrometers, about 460 micrometers, about 470 micrometers, about 480 micrometers, about 490 micrometers, about 500 micrometers, about 510 micrometers, about 520 micrometers, about 530 micrometers, about 540 micrometers, about 550 micrometers, about 560 micrometers, about 570 micrometers, about 580 micrometers, about 590 micrometers, about 600 micrometers, about 610 micrometers, about 620 micrometers, about 630 micrometers, about 640 micrometers, about 650 micrometers, about 660 micrometers, about 670 micrometers, about 680 micrometers, about 690 micrometers, about 700 micrometers, about 750 micrometers, about 800 micrometers, about 850 micrometers, about 900 micrometers, about 950 micrometers, about 1000 micrometers, about 1.1 millimeters, about 1.2 millimeters, about 1.3 millimeters, about 1.4 millimeters, about 1.5 millimeters, about 1.6 millimeters, about 1.7 millimeters, about 1.8 millimeters, about 1.9 millimeters, about 2 millimeters, about 3 millimeters, about 4 millimeters, about 5 millimeters, or more than about 5 millimeters, or, in other embodiments, in ranges between any two of the above values.

In some embodiments, a laser diode emitting light with a 1.87-micron wavelength stimulates nerves. This wavelength is important because devices capable of generating this wavelength are more available than longer mid-IR wavelengths. In some embodiments, laser-diode light of a 2.1-micron wavelength is used for nerve stimulation. Laser diodes that emit 2.1-micron-wavelength light are currently in research and would most likely work as well as other wavelengths, since this wavelength, when generated by a lamp-pumped solid-state laser, has been shown to be effective in stimulating nerves. In some embodiments, a laser-diode device (having one or more emitters) outputs light that is used for nerve stimulation, wherein the light has a wavelength of between about 1.5 microns and about 6 microns; in various embodiments, for example, the wavelength is in the far infrared at about 1.5 microns, or about 1.51 microns, about 1.52 microns, about 1.53 microns, about 1.54 microns, about 1.55 microns, about 1.56 microns, about 1.57 microns, about 1.58 microns, about 1.59 microns, about 1.6 microns, about 1.61 microns, about 1.62 microns, about 1.63 microns, about 1.64 microns, about 1.65 microns, about 1.66 microns, about 1.67 microns, about 1.68 microns, about 1.69 microns, about 1.7 microns, about 1.71 microns, about 1.72 microns, about 1.73 microns, about 1.74 microns, about 1.75 microns, about 1.76 microns, about 1.77 microns, about 1.78 microns, about 1.79 microns, about 1.8 microns, about 1.81 microns, about 1.82 microns, about 1.83 microns, about 1.84 microns, about 1.85 microns, about 1.86 microns, about 1.87 microns, about 1.88 microns, about 1.89 microns, about 1.9 microns, about 1.91 microns, about 1.92 microns, about 1.93 microns, about 1.94 microns, about 1.95 microns, about 1.96 microns, about 1.97 microns, about 1.98 microns, about 1.99 microns, about 2.0 microns, about 2.01 microns, about 2.02 microns, about 2.03 microns, about 2.04 microns, about 2.05 microns, about 2.06 microns, about 2.07 microns, about 2.08 microns, about 2.09 microns, about 2.1 microns, about 2.11 microns, about 2.12 microns, about 2.13 microns, about 2.14 microns, about 2.15 microns, about 2.16 microns, about 2.17 microns, about 2.18 microns, about 2.19 microns, about 2.2 microns, about 2.21 microns, about 2.22 microns, about 2.23 microns, about 2.24 microns, about 2.25 microns, about 2.26 microns, about 2.27 microns, about 2.28 microns, about 2.29 microns, about 2.3 microns, about 2.31 microns, about 2.32 microns, about 2.33 microns, about 2.34 microns, about 2.35 microns, about 2.36 microns, about 2.37 microns, about 2.38 microns, about 2.39 microns, about 2.4 microns, about 2.5 microns, about 2.6 microns, about 2.7 microns, about 2.8 microns, about 2.9 microns, about 3 microns, about 3.1 microns, about 3.2 microns, about 3.3 microns, about 3.4 microns, about 3.5 microns, about 3.6 microns, about 3.7 microns, about 3.8 microns, about 3.9 microns, about 4 microns, about 4.1 microns, about 4.2 microns, about 4.3 microns, about 4.4 microns, about 4.5 microns, about 4.6 microns, about 4.7 microns, about 4.8 microns, about 4.9 microns, about 5 microns, about 5.1 microns, about 5.2 microns, about 5.3 microns, about 5.4 microns, about 5.5 microns, about 5.6 microns, about 5.7 microns, about 5.8 microns, about 5.9 microns, or about 6.0 microns, or, in other embodiments, in ranges between any two of the above values. In other embodiments, an LED having output wavelengths centered in one of these ranges is used as a source of light to stimulate nerves.

In still other embodiments, one or more laser diodes or LEDs that output shorter wavelengths (including short IR, visible, and/or ultraviolet light) is used as a source of light to stimulate nerves. In particular, visible wavelengths are important because devices capable of generating a great number of different ones of these shorter wavelengths are becoming more available, and use of visible light makes the location of the stimulation signal readily apparent to the user without the use of separate lasers or LEDs as visible markers. On the other hand, longer IR laser wavelengths tend to be more eye-safe (since the liquids and structures in the front of the eye absorb or block longer IR wavelengths), while shorter laser wavelengths can present an eye hazard with respect to which, precautionary protective measures must be taken. Further, different wavelengths have different penetration depths into various tissues, so a selected penetration depth can be achieved by changing wavelength without changing optical power, or by a combination of a selected wavelength and a selected power. In some embodiments, a laser diode having an output wavelength of about 0.95 microns (in the infrared) is used for nerve stimulation. In some embodiments, a laser-diode device (having one or more emitters) outputs light that is used for nerve stimulation, wherein the light has a wavelength of between about 1.5 microns and about 0.2 microns. In various embodiments, for example, the wavelength is in the infrared spectrum at about 0.7 microns, about 0.71 microns, about 0.72 microns, about 0.73 microns, about 0.74 microns, about 0.75 microns, about 0.76 microns, about 0.77 microns, about 0.78 microns, about 0.79 microns, about 0.8 microns, about 0.81 microns, about 0.82 microns, about 0.83 microns, about 0.84 microns, about 0.85 microns, about 0.86 microns, about 0.87 microns, about 0.88 microns, about 0.89 microns, about 0.9 microns, about 0.91 microns, about 0.92 microns, about 0.93 microns, about 0.94 microns, about 0.95 microns, about 0.96 microns, about 0.97 microns, about 0.98 microns, about 0.99 microns, about 1.0 microns, or about 1.01 microns, about 1.02 microns, about 1.03 microns, about 1.04 microns, about 1.05 microns, about 1.06 microns, about 1.07 microns, about 1.08 microns, about 1.09 microns, about 1.1 microns, about 1.11 microns, about 1.12 microns, about 1.13 microns, about 1.14 microns, about 1.15 microns, about 1.16 microns, about 1.17 microns, about 1.18 microns, about 1.19 microns, about 1.2 microns, about 1.21 microns, about 1.22 microns, about 1.23 microns, about 1.24 microns, about 1.25 microns, about 1.26 microns, about 1.27 microns, about 1.28 microns, about 1.29 microns, about 1.3 microns, about 1.31 microns, about 1.32 microns, about 1.33 microns, about 1.34 microns, about 1.35 microns, about 1.36 microns, about 1.37 microns, about 1.38 microns, about 1.39 microns, about 1.4 microns, about 1.41 microns, about 1.42 microns, about 1.43 microns, about 1.44 microns, about 1.45 microns, about 1.46 microns, about 1.47 microns, about 1.48 microns, about 1.49 microns, or about 1.5 microns, or, in other embodiments, in ranges between any two of the above values.

In various other embodiments, for example, the wavelength is in the visible spectrum at about 0.4 microns, or about 0.41 microns, about 0.42 microns, about 0.43 microns, about 0.44 microns, about 0.45 microns, about 0.46 microns, about 0.47 microns, about 0.48 microns, about 0.49 microns, about 0.5 microns, about 0.51 microns, about 0.52 microns, about 0.53 microns, about 0.54 microns, about 0.55 microns, about 0.56 microns, about 0.57 microns, about 0.58 microns, about 0.59 microns, about 0.6 microns, about 0.61 microns, about 0.62 microns, about 0.63 microns, about 0.64 microns, about 0.65 microns, about 0.66 microns, about 0.67 microns, about 0.68 microns, about 0.69 microns, or about 0.7 microns, or, in other embodiments, in ranges between any two of the above values.

In various other embodiments, for example, the wavelength is in the ultraviolet spectrum at about 0.1 microns, or about 0.11 microns, about 0.12 microns, about 0.13 microns, about 0.14 microns, about 0.15 microns, about 0.16 microns, about 0.17 microns, about 0.18 microns, about 0.19 microns, about 0.2 microns, about 0.21 microns, about 0.22 microns, about 0.23 microns, about 0.24 microns, about 0.25 microns, about 0.26 microns, about 0.27 microns, about 0.28 microns, about 0.29 microns, about 0.3 microns, about 0.31 microns, about 0.32 microns, about 0.33 microns, about 0.34 microns, about 0.35 microns, about 0.36 microns, about 0.37 microns, about 0.38 microns, about 0.39 microns, or about 0.4 microns, or, in other embodiments, in ranges between any two of the above values.

In some embodiments, the invention uses a nerve-stimulation signal composed of one or more wavelengths within a range between two numbers selected from the set that includes all of the above listed far-infrared-, visible-, infrared-, or ultraviolet-spectrum wavelengths.

In some embodiments, two or more different wavelengths are used in combination for nerve stimulation. In some embodiments, the different wavelengths have different penetration depths into a given tissue, so in some embodiments, the present invention applies light at a first wavelength from a first laser to achieve a first tissue-penetration depth, but applies light at a second wavelength from a second laser to achieve a second tissue-penetration depth. In some embodiments, a variable amount of each of the two or more different wavelengths is applied simultaneously to achieve a tissue-penetration depth that is variable based on the amounts (intensities) of the first and second light wavelengths. In some embodiments, the two or more different wavelengths are used in combination in cases where the simultaneous combination of two or more different wavelengths achieves higher stimulation results when applied to a specific type of neural tissue than is achieved by the application of either wavelength alone. In some embodiments, the two or more different wavelengths are passed through a single optical fiber for delivery to the target neural tissue.

In other embodiments, different IR wavelengths have different depths of penetration into living tissue (e.g., nerve tissue), and thus one IR nerve-stimulation wavelength is used for penetration to a first depth, and a second IR nerve-stimulation wavelength is used for penetration to a second depth that is different than the first depth. In some embodiments, the two or more different wavelengths are passed through a single optical fiber for delivery to the target neural tissue.

In still other embodiments, different IR wavelengths have different absorption ratios or different stimulation results for different tissue types (e.g., for different types of nerves or neural tissue), and thus one IR nerve-stimulation wavelength is used for stimulation of a first type of neural tissue, and a second IR nerve-stimulation wavelength is used for stimulation of a second type of neural tissue that is different than the first type. In some embodiments, the two or more different wavelengths are passed through a single optical fiber for delivery to the target-neural-tissue area.

In some embodiments, the two or more different wavelengths are generated by two or more solid-state light-emitting devices, such as laser diodes, light-emitting diodes, optically pumped fibers, and the like, and are then combined into a single optical fiber. In other embodiments, the two or more wavelengths are sent through separate parallel fibers or through different cores in a single fiber.

In some embodiments, the optical stimulation light is directed to a very small area of neural tissue, for example in order to stimulate a subset of one or more nerves within a nerve bundle (for example, to stimulate a motor nerve (a nerve that conducts signals from the brain to one muscle or a portion of a muscle), or to stimulate a sensory nerve (a nerve that conducts signals to the brain from a small area of touch-sensing nerves), or an auditory nerve for a single audio frequency, or an optical nerve for a small portion of the visual field or color-sensing spectrum). In some embodiments, such a precision-directed optical signal includes a single optical wavelength, while in other embodiments two or more different IR-stimulation wavelengths are used for stimulating a single nerve or neural tissue area. In some embodiments, two or more different wavelengths provide a stronger stimulation to one nerve cell or one portion of tissue, while in other embodiments two or more different IR-stimulation wavelengths provide different depths of penetration, such that a selected depth or range of depths can be chosen by selecting the wavelength(s) that reach to those depths.

In some embodiments, the optical stimulation light is directed to a larger area of neural tissue, for example in order to stimulate a larger number of nerves or brain cells. It has been found that in some embodiments, the optical stimulation of a single brain cell or a small number of brain cells is ineffective in initiating a neural response, while the optical stimulation of a larger number of brain cells is effective. In some embodiments, delivery of this larger-area optical signal includes a single optical wavelength, while, in other embodiments, two or more different wavelengths are used. In some embodiments, an optical lens, holographic imager, or other imaging device is used to direct light from an optical fiber to the larger area that is to be stimulated. In some embodiments, a grating (e.g., a distributed Bragg reflector having a characteristic grating spacing chosen to eject light from the fiber along the grating length) is imposed along a length (e.g., in various embodiments, 0.1 mm, 0.2 mm, 0.3 mm, 0.4 mm, 0.5 mm, 0.6 mm, 0.7 mm, 0.8 mm, 0.9 mm, 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, or longer than 20 mm) of the delivery end of a fiber in order that the stimulation optical signal is forced to leave the fiber over a length of the grating, in order that the optical signal is directed to neural tissue over that length of grating on the fiber. For discussion purposes, the dimension along the fiber at its emissive end is called the X-direction. In some embodiments, a plurality of optical fibers is disposed such that their ends emit light across a line perpendicular to their length. For discussion purposes, the dimension perpendicular to the fibers at their emissive end is called the Y-direction. In some embodiments, a plurality of fibers, each having a grating on its end, are placed side-by-side such that light is emitted to a larger area, wherein light has an extent in the Y-direction due to the side-by-side spacings of the multiple fibers and an extent in the X-direction due to the lengths of the gratings on each fiber. In some embodiments, one or more IR stimulation wavelengths are also chosen to be emitted across different extents along a Z-direction, such that a volume of neural tissue having selected extents in the X-direction, Y-direction, and Z-direction is stimulated using the optical stimulation signal.

In some embodiments, a plurality of optical fibers is used to deliver optical-stimulation pulses to different points along the same nerve fiber or bundle at different times. For example, in some embodiments, a first fiber A delivers an optical-stimulation pulse to point $X_A$ along a nerve at a time $t_0$, then later a second fiber B delivers an optical-stimulation pulse to point $X_B$ further along the nerve at a later time $t_4$. In some embodiments, the relative timings of the times of the optical-stimulation pulses at $t_0$ and $t_4$ are selected such that the action potential traveling along the nerve is reinforced or strengthened.

In some embodiments, one nerve is stimulated using different wavelengths applied to different locations along the nerve; for example 1.8-micron-wavelength light can be applied to a first point and 2.2-micron-wavelength light can be applied to a second point. In some embodiments, both the wavelength and the timing of the light stimulation are varied along the nerve.

In some embodiments, a diode laser is employed for nerve stimulation. This is important because a single-diode laser is a very low-cost source compared to free-electron lasers (FEL), fiber lasers or pumped solid-state lasers, just to name a few. A single emitter is used in some embodiments, but, in other embodiments, may not provide enough power for certain purposes. In other embodiments, a multiple-emitter laser-diode device is used, wherein light from a plurality of emitters is directed to a single nerve. In some embodiments, a combiner is used to combine light from a plurality of emitters into a single fiber. In some embodiments, one or more side-emitting lasers are employed, while in other embodiments surface-emitting lasers are used. In some embodiments, a combination of different laser types is used, e.g., based on the need to generate certain combinations of wavelengths or powers.

In some embodiments, the laser-diode device is coupled to one or more optical fibers that convey the light to the location at the nerve for stimulation. In other embodiments, the laser diode itself is positioned at the point of stimulation, eliminating the need for the optical fiber.

In some embodiments, a WDM (wavelength-division multiplexing) coupler is used to combine two or more wavelengths to be transmitted through a fiber to be ultimately delivered to nerve tissues. Such couplers combine light at differing wavelengths supplied to two or more optical-fiber ports, to produce a single multi-wavelength beam at an additional optical-fiber port. WDM couplers are well-known in the field of telecommunication systems; an early example is described in U.S. Pat. No. 4,296,995, with a more recent example described in U.S. Pat. No. 5,796,889. In some instances of each of the embodiments described herein, a WDM coupler is used to couple light from the emitters (e.g., laser diodes or LEDs) into an optical-fiber structure.

In at least one embodiment, it is important to make the fiber core's size or sizes small for stimulating smaller nerves. More to the point, given the small size of some nerve fibers, a fiber core and a laser diameter corresponding to (e.g., equal to or smaller than) the diameter of this nerve fiber need to be provided. In some embodiments, a fiber core much smaller than the nerve fiber is used. For example, in some embodiments, a fiber core having a one-micron (or smaller) diameter is used. In other embodiments, fibers having core diameters of 100 microns or larger are used. In some embodiments, the optical fibers are made of a glass such as silica or other suitable material (such as plastic). In some embodiments, the optical-fiber bundle used for imaging the tissue being stimulated and observed is made of plastic and/or glass fibers. In some embodiments, multiple small-core fibers can be used to simulate multiple small nerves simultaneously or independently.

In at least one embodiment, a fiber-coupling technique is implemented to increase the brightness of light in the optical fiber by coupling light from a plurality of laser emitters (e.g., from a laser-diode bar) for biological stimulation (i.e., nerve or tissue stimulation). There are many different fiber-coupling techniques that may be employed to increase the brightness of a laser-diode bar. For example, co- and contra-directional and evanescent coupling are just a few of the coupling techniques known in the art. Through empirical testing and/or modeling, a suitable effective fiber-coupling technique can be determined for use with a laser-diode bar.

In some embodiments, a single-emitter laser diode is implemented and used to direct laser light of some efficacious wavelength to a particular target nerve. As described elsewhere herein, such single-emitter laser diodes may be side-emitting and/or surface-emitting laser diodes. The efficacy of a particular diode can be determined through empirical testing and/or modeling.

In some embodiments, there is a combining and co-alignment of a visible wavelength with the IR-stimulation light in order to provide a visual cue for directing the IR-stimulation light used for stimulating a nerve. Laser light in the IR range (e.g., 700 nm-1850 nm or longer) is not visible to the human eye. Due to this fact, as a practical matter, this IR optical-stimulation light cannot be easily aimed to a particular target (e.g., a nerve fiber) using the naked eye. In some embodiments, visible light (i.e., light in the 400- to 700-nm range from a laser diode, L.E.D., or other source) is also inserted into the optical fiber or fiber bundle and used to guide movement of the emitting end of the fiber to aim the IR light so as to allow the IR light to be applied in an efficacious manner to, for example, stimulate a nerve fiber. In some embodiments, the visible light is passed through one or more fibers or fiber bundles (i.e., this can be using the same fiber(s) as the IR optical-stimulation light, or in other embodiments, using a separate fiber) so as to provide a target spot. Next (or simultaneously), IR light is passed through the same one or more fibers to the same point on a nerve fiber that the visible light previously illuminated or currently illuminates. In some embodiments, both the IR light and visible light have separate light sources that are coupled into a commonly shared optical-fiber structure, whereas, in other embodiments, a separate optical-fiber structure is used to channel each wavelength of light. In some embodiments, an optical-fiber structure is used in which at least some fibers are used to transmit light of one wavelength, while at least some other fibers are used to transmit light of a different wavelength (for example, in some embodiments, different fibers are used to carry the visible light, the IR-stimulation light, and/or the cutting/ablating/cauterizing light, and/or to return the imaging light obtained from the tissue being targeted). In some embodiments, still other optical fibers are used to carry control-light signals to and from the handpiece, such that an operator holding the handpiece can selectively command a remote light source to do his/her bidding. As described below, these optical-fiber structures are operatively coupled to a glass, ceramic plastic or some other type of ferrule or plug made from a non-magnetic material.

In some embodiments, the visible laser light is selected from one or more wavelengths empirically selected to selectively show a visible difference in reflected brightness when directed at nerve fibers as compared to blood vessels, muscles, connective and other tissues. For example, in some embodiments, a combination of red, green and/or blue laser or LED light is used. In some embodiments, green light has been found to be more effective (as an indicator of where the fiber delivery head is pointing) than red or blue light alone. In some embodiments, a fiber bundle (with plastic and/or glass fibers) capable of obtaining and transmitting optical two-dimensional color imaging to a remote location is used to convey image information from the subject (e.g., in an MRI machine) to a remote viewing location. In some embodiments, a machine-vision system is used to distinguish color features of tissues (e.g., hue, tint, and/or brightness) and/or shapes of tissues from a digital or video image, and to display an enhanced image derived therefrom for the operator.

In some embodiments, an IR video imager is used to obtain and display the location of the IR-stimulation signal without the addition of visible-wavelength light. In some embodiments, a fiber bundle or other structure capable of obtaining and transmitting optical two-dimensional IR imaging to a remote location is used to convey image information to a remote IR imager.

In some embodiments, a second, high-power laser signal (called the "surgical signal") is coupled through fiber to the stimulation area, wherein the operator can stimulate nerve tissue using a first stimulation-wavelength-and-power optical signal (called the "stimulation signal") to distinguish tissue that is to be saved from tissue that is to be cut or destroyed, and then use the high-power laser light to cut, ablate, or cauterize the tissue to be destroyed. In some such embodiments, the optical-stimulation signal is provided by a first laser source (e.g., a laser diode, optically-pumped fiber laser, or the like), and the optical surgical signal is provided by a second laser source of higher intrinsic power or energy, or of a different wavelength more suited for surgical purposes (e.g., another laser diode, optically-pumped fiber laser, or the like). In other embodiments, a single laser source is used for both the optical stimulation signal and the optical surgical signal, wherein a parameter of the signal is changed to achieve one function or the other (e.g., in some embodiments, the optical surgical signal is obtained by shortening the pulse length, for example by Q-switching, in order that a given amount of energy is delivered in a very short time to ablate a small area of tissue, or by lengthening a pulse length having a constant average energy or by increasing the number of pulses sent in a short time period in order that one or more pulses with a given average power integrate over time to heat the tissue being treated).

In some embodiments, the targeting of various nerve fibers is performed manually (e.g., by manually moving a handpiece to locate the delivery end of an optical fiber so that light energy may be directed on to the nerve to be stimulated), whereas, in other embodiments, this targeting is performed automatically through the use of targeting software (e.g., initially stored on a computer-readable medium), wherein the targeting software controls operation of a computer that moves servos or other suitable actuators to move the optical signal to impinge on a desired location. In an embodiment utilizing software, the image generated from an MRI device (e.g., a functional MRI) is used as a map to guide the targeting of an IR light source as projected through an optical tip. In some embodiments, this map describes the topology of the target area, providing significant references based upon which the IR light source can be guided. In some embodiments, an input device such as a mouse, joystick, light pen, or other suitable device is used to input commands from a surgeon or other user to direct where the software is to direct stimulation (the location of nerve tissue to be stimulated).

In some such embodiments, a remote actuator (e.g., an optical-fiber platform such as described in FIG. 6A) is on a platform fixed in relationship to a subject (e.g., patient), such that a surgeon views the tissue on a computer monitor, and inputs commands, locations, and/or other information to control movement of the remote actuator, as well as to control the visible signal, optical stimulation signal, and/or optical surgical signal that is to be sent down an optical fiber to the actuator and then to the tissue.

In some embodiments, as is disclosed below, the pulse shapes of the light passing through the device can be controlled through the use of a light-pulse device that regulates the light under control of a computer, processor or CPU (e.g., x86 series, Intel 8051 series utilizing certain computer-executable instructions stored to a computer-readable medium, or under control of a non-computer, non-programmed electronic circuit).

A computer-readable medium is defined to be a medium for carrying or having computer-executable instructions or data structures stored thereon. Such computer-readable media may be any available medium that is accessible by a general-purpose or special-purpose computer system. By way of example, and not limitation, such computer-readable media can include physical storage media such as RAM, ROM, or EPROM, removable media such as CD-ROM or other optical-disk storage, diskettes, magnetic hard-disk storage or other magnetic-storage devices, or any other media which can be used to carry or store desired program code means in the form of computer-executable instructions, computer-readable instructions, and/or data structures and which may be accessed by a general-purpose or special-purpose computer system; this physical storage media may be fixed to the computer system as in the case of EPROM or a magnetic hard drive, or removable as in the case of an EEPROM on a USB-connected device (e.g., flash memory device) or CDROM, DVD, or diskette, or can include network-connected storage (such as a hard drive connected to the internet. In some embodiments, these instructions are written in an object-oriented programming language such as C++, Java™, or Delphi™, and compiled or interpreted into some type of machine-readable format such as binary code, byte code or the like. And again, in some embodiments, these instructions are written in a structured programming language such as C, and compiled or interpreted into a machine-readable format such as binary code.

In some embodiments, various methods, systems, apparatus or the like are employed to guide the IR light to its target nerve fiber. In some embodiments, a disposable, biologically inert, non-metallic or non-magnetic optical tip at the end of a fiber is provided. In some embodiments, this tip is adjustable or interchangeable so as to allow for the spot size to vary depending on type of nerve to be stimulated. In some embodiments, this tip is configured in the form of a light pen, pointer or similar handheld device so as to allow the user to manually target a particular nerve fiber or series of fibers. In some embodiments, this optical tip is encased in or affixed to a disposable plastic sheath (e.g., a sterile sheath that is used once for an operation and then discarded), whereas in other embodiments it is encased in an end of the aforementioned light pen, pointer or similar device. In some embodiments, a sterile disposable sheath is applied to the handpiece before each use, and is discarded afterwards. In other embodiments, the handpiece, light pen, pointer or the light-delivery device itself is provided in a sterile condition, and is inexpensive enough to be disposable.

In some embodiments, the optical path is selectively interruptible by a mechanical shutter and/or variable aperture that allows the user to control the passage of laser light (i.e., the visible signal, optical-stimulation signal, optical surgical signal or the like) through the optical tip. In some embodiments, the shutter is used to start and stop the light passing through the optical tip. In some embodiments, as with the other components that form the delivery end of the device, this shutter and/or aperture is made from a non-metallic material such as a plastic, ceramic or similar material. In some embodiments, the variable aperture is adjustable to control the amount of light (e.g., the power and/or size of the spot), which, in some embodiments, also includes the start and stop of the light signal to the target tissue. In some embodiments, an iris diaphragm is provided to regulate the variable aperture through which light passes. In some embodiments, a non-metallic material such as a plastic, ceramic or similar material is used to construct the iris diaphragm. In some embodiments, the optical tip is secured to, or with, a ferrule or similar apparatus used to connect the optical tip and optical-fiber structure.

In some embodiments, the flow of light, be it IR or visible, is controlled via a mechanical linkage incorporated into the above-described handpiece, light pen or pointer. In such an embodiment, the linkage includes a trigger-like device that, when depressed or otherwise manually controlled, controls the flow of the above-disclosed light. In other embodiments, the trigger or manual control operates to manipulate an optical control signal that is coupled to a remote electro-optical control device that runs the operation, timing and function of the device. For example, in some embodiments, a remote laser transmits a laser signal down an optical fiber, and the manual control reflects back up the optical fiber a portion of the laser signal (e.g., when a first button is pressed, one pulse is reflected, when a second button is pressed, two successive pulses are reflected, and so on, or different neutral-density filters are used to vary the amount of light that is reflected). In some embodiments, more than one fiber is used to send and/or receive the optical control signal(s).

In some embodiments, a sterile, disposable covering or sheath constructed from plastic, polymer or some other substance is placed over the above-described handpiece, light pen or pointer. This disposable covering is then discarded after use of the handpiece, light pen or pointer. In some embodiments, this disposable covering includes one of a plurality of different beam-shaping optics that allow for different beam characteristics for different applications.

In some embodiments, IR light in a higher or lower range may be more or less efficacious. For example, near-IR light (e.g., in the 700-1400-nm range) may be better for nerve-damage repair (or for cutting, ablating or cauterizing), while short-wavelength IR light (e.g., in the 1400-3000-nm range) may be better for vagus nerve stimulation, etc. The efficacy of a particular IR wavelength can be determined through empirical testing and/or modeling.

In some embodiments, silica ($SiO_2$) fiber for delivering laser light to a nerve is utilized. The advantages of using silica include low attenuation loss in delivering laser light.

In some embodiments, a power supply is implemented that can provide programmable pulse shapes (e.g., pulse width, repetition rate, etc.). In some embodiments, a laser light source—be it an IR, visible or some other light source—is operatively coupled to a timer or pulse-regulating device that can control the shape, magnitude, cycles or other features of a light pulse. In some embodiments, this pulse-regulating device is used in conjunction with the above-described shutter, while in other embodiments it is used alone. In some embodiments, the pulse-regulating device is used outside of the magnetic field generated by an MRI device, so as to not present a danger to an individual using an MRI device. In some embodiments, a thumb/finger control mechanism includes a non-magnetic (e.g., plastic) component mechanism that is optically assessed in order to control the light source to drive a particular pulse shape (e.g., an optical assessment signal (e.g., an unmodulated laser or LED light signal) is sent to the component mechanism that is part of the thumb/finger control mechanism, and the state of the component mechanism, which is a function of the position of the thumb/finger control mechanism, changes a characteristic of the light and returns it as an optical control signal). Specifically, whereas in some embodiments programmable pulses are automatically generated, in at least one embodiment, pulse shapes can be modified using a thumb/finger control that can modify the pulse width, repetition rate and the like. In some embodiments, a knob, toggle or other switch is used that allows a user to modify the pulse width by turning, for example, a knob to a particular position. The use of a knob, toggle or the like to modify the various pulse shapes can be determined through assessing the ergonomic benefits of a particular switch and switch location on the above-described handpiece or light pen.

In some embodiments, a stable platform with a remote control is implemented to allow for the delivery of IR light to a target nerve fiber. In at least one embodiment, rather than manually targeting a specific nerve fiber the targeting and delivery process can be performed using a remotely operated device to move and manipulate the above-described handpiece or light pen. For example, in some embodiments, a joy stick or other control device is used to adjust, manipulate the handpiece or light pen attached to a mechanical arm such that IR light is efficaciously delivered to the target area. This arm is constructed from a non-magnetic material such as plastic, glass, ceramic or the like.

In some embodiments, certain scan techniques are used that rapidly stimulate areas automatically for use in applications such as functional MRI, using galvo-scanning mirrors or fiber bundles that accept the source light at a first end of all the fibers of the bundle and have their opposite ends spread in a predetermined pattern (such as pointing at different angles into a globe volume, or across a linear space as shown in FIG. 4) such as are used in certain helicopter infrared countermeasures (IRCMs). In at least one embodiment, it may be more effective to use some type of scanning technique to treat one or more nerve fibers than to manually target such fibers using the above-disclosed methods. In using such methods, a scan is performed of the target area (which may, for example, be a series of nerve fibers) and from this scan certain features are revealed. Once these features are revealed, an efficacious dose of IR laser light can be applied to the target area.

In at least one embodiment, a laser-wavelength-selective device is implemented to couple the visible light and provide power control or laser-safety monitoring or output-power measurement. In some embodiments, this is done with a 10% beam splitter to couple 10% of the visible laser signal into the fiber with the stimulation-wavelength signal.

In some embodiments, the present invention includes one or more light sources operatively coupled to one or more optical-fiber structures. In some embodiments, these light sources are an IR laser, or visible laser light just to name a few. In some embodiments, the optical-fiber structure is surrounded with a protective plastic covering. This optical-fiber structure is, in turn, operatively coupled to a plug constructed from glass, ceramic, plastic or some other material that does not conduct magnetic energy. This plug is then inserted into the above-described handpiece, light pen or pointer. The light from the light source is then passed though the optical tip of the handpiece, light pen or pointer. In some embodiments, this light, and its pulse shapes, can be controlled by a pulse-regulating device operatively coupled to the light source as is disclosed above.

In some embodiments, a plurality of light-emitting optical-fiber structures is used to emit efficacious IR and/or visible light to stimulate nerve tissue. In at least one embodiment, the tips of these optical-fiber structures are arranged in an array-type pattern, whereas in other embodiments the tips are arranged in a matrix-type pattern. Other patterns are also provided and are only limited by empirical testing and/or modeling to determine which patterns are more or less effective. In some embodiments, fibers arranged in an array-type pattern are oriented horizontally, relative to, for example, a human hand which may manipulate these fibers. In some embodiments, this array or matrix is operatively coupled to a light pen, wand or similarly configured instrument.

In some embodiments, in those instances where an array- or matrix-type configuration is used software is used to isolate an isomorphism between a particular light-emitting optical-fiber structure and certain nerve tissues. Put another way, once a reaction of a particular nerve tissue is determined, software can be used to determine which light-emitting optical-fiber structure actually caused the reaction on the part of the nerve tissue. The algorithm to determine which light-emitting structure caused a reaction could be a simple sequential-search algorithm whereby each light-emitting optical-fiber structure individually emits light by itself and a nerve-tissue reaction is determined to be present or absent, or it could be a more sophisticated binary-search algorithm whereby, for example, an array of light-emitting optical-fiber structures is divided in half, each sub-array tested individually to determine whether a nerve-tissue reaction is present or absent, and if one sub-array is indeed associated with a nerve-tissue reaction then that sub-array is again divided in half and the process repeated. Some embodiments use algorithms to search array-like structures and matrices, such as are well known in the art. (See *Algorithms in C++: Parts* 1-4 3$^{rd}$ *Edition*, by Robert Sedgewick, Addison Wesley 1998.)

FIG. 1A is a block diagram 100 of a first laser device using a mechanical trigger mechanism 108 mounted on a handpiece 140. In some embodiments, this example of the present invention has an IR-laser-diode bar 101 operatively coupled to a beam-combiner optic or optics 103 via one or more optical-fiber structures 111. In some embodiments, additionally, operatively attached to the beam-combiner optic or optics 103 is a visible laser 102. As with the IR-laser-diode bar 101, this too is operatively connected to the beam-combiner optic or optics 103 via one or more optical-fiber cables 111. In at least one embodiment, the beam-combiner optic or optics 103 is operatively connected to a ferrule 107 that contains a light-emitting optics or lens 115 positioned at one end of the ferrule 107. The ferrule 107 is operatively coupled to the combiner optic or optics 103 via one or more optical-fiber cables 109 through which IR laser and/or visible light is passed. In some embodiments, control of this IR and/or visible light is via a trigger 108 being pressed by the finger of user 89, which is operatively coupled to a laser controller/power controller 104 (which may alternatively be designated light-emitting-source controller 104) via mechanical linkage 106 and specifically via various control arms 112. In some embodiments, the light-emitting-source controller 104 is operatively coupled to the IR-laser-diode bar 101 via a bus 110 so as to regulate the output of laser light. In some embodiments, the ferrule 107, attached optical-fiber structures 109, trigger 108 and mechanical linkage 106 are grouped together and protected via a disposable replaceable sheath 105 to form handpiece 140. Specifically, in some embodiments, the ferrule 107, mechanical linkage 106 and trigger 108 are inserted into the disposable sheath 105 via an opening 113. In some embodiments, the disposable sheath 105 is pulled over the length of the ferrule 107 and attached optical-fiber structures 109, mechanical linkage 106, and accompanying trigger 108 until the light-emitting optics or lens 115 of the ferrule 107 is flush with the opening 114. In some embodiments, the ferrule 107, optics or lens 115, trigger 108, mechanical linkage 106, handle 132, and disposable sheath 105 are manufactured from non-metallic, non-magnetic materials such as plastics, polymers, ceramics or the like. In some embodiments, the optics or lens 115 are included as part of the disposable sheath 105. This allows the optics to be interchanged by swapping sheaths. In some embodiments, disposable sheath 105 includes some or all of the optics needed to direct light from optical-fiber ferrule 107 onto the neural tissue as desired. In some embodiments, disposable sheath 105 and its optics are interchangeable with other disposable sheaths 105 having different optics, in order to easily obtain the desired optical pattern uniquely suited for nerve or brain stimulation. In some embodiments, the light pattern desired from the optics is empirically determined. In other embodiments, the sheath 105 provides a clear window, and an interchangeable optics mechanism (e.g., a threaded or snap-in adaptor configured to easily change the imaging portion to one of a plurality of different imagers) is provided in the handpiece.

In some embodiments, an imaging optics turret is provided at the operative end of handpiece 140, such that different optical patterns, spot sizes, and/or focal lengths can be provided by selecting one of a plurality of different lenses or holographic imagers (e.g., a turret that can be rotated to select one imaging optical element of the plurality of imaging optics). In other embodiments, a zoom-type lens is provided such that spot size and/or shape and focal length can be independently changed.

In some embodiments, the optical-fiber structures 109 and/or mechanical linkage 106 are between 5 and 50 meters in length. The length of the optical-fiber structures 109 and mechanical linkage 106 can be determined through empirical selection and/or modeling so as to allow magnetic or metallic portions of this device to be a safe distance from the magnetic-field effects of an MRI device.

In some embodiments, a single optical fiber or a single optical-fiber bundle carries both the IR-light stimulation signal as well as the visible-light pointer signal, and optionally also carries a higher-power laser light beam that can be used for surgical purposes (e.g., ablation, cutting, tissue heating and/or cauterization, and the like). In some embodiments, the visible light also provides an indication of the currently selected function that is or can be activated by the user.

In some embodiments, a plurality of manually activable trigger buttons and corresponding mechanical linkages are provided to select and/or activate one or more of a plurality of different functions of the handpiece, as described below.

In other embodiments, the mechanical linkage(s) and trigger(s) are omitted and replaced with a non-magnetic optical-fiber-connected controller-selector that is manually operable to select and/or activate one or more functions. In still other embodiments, a foot-operated control is used instead.

In some embodiments of the mechanically-linked or optical-fiber-connected manual controls (or a similarly functional foot control), three buttons are provided: a first button that when pushed a first time starts a series of one or more optical pulses, which series of one or more optical pulses optionally can automatically stop after a period of time determined by the function selected, or optionally can stop only after the user presses this first button a second time; a second button that, when pressed, advances a function-selecting state machine to the next one of a plurality of different optical-stimulation functions (e.g., no stimulation function is selected, or selecting the duration, intensity, pulse rate, pulse shape, pulse-train shape or pattern, and/or wavelength(s), and the like, for the IR stimulation light), wherein these functions are activated and/or deactivated by pressing the first button; and a third button that, when pressed, advances a state machine to the next one of a plurality of different optical-surgery functions (e.g., no surgical function is selected, or ablation, cutting, cauterizing, and the like functions for the high-powered laser light) that are activated and/or deactivated by pressing the first button. In some embodiments, successive presses of the stimulation or surgery function-selection buttons cycle through each of the items on the menu(s) of functions available.

In some embodiments, a single actuation/control button 108 is used both to select a stimulation function (e.g., by successive single long-duration presses of button 108 to select different functions as shown, e.g., in FIG. 1B) and to control triggering or timing of the stimulation light (e.g., by a quick double-click of button 108).

In some embodiments, upon changing the stimulation and/or surgery function by pressing of the respective function-selection buttons, the color of the visible light being sent down the optical fiber changes to a different color (e.g., hue, saturation, and/or intensity) and/or pulse (brightness pulsations) pattern, wherein the visible light color and/or pulsing of the light intensity is indicative of the function selected, thus providing instant feedback to the user concerning which function is currently active. For example, in some embodiments, a steady light of one of a plurality of different colors indicates that a stimulation function has been selected, wherein the color indicates which of the stimulation functions has been selected; whereas a quickly pulsating light of one of a plurality of different colors (also different than the stimulation-indicating colors) indicates that a surgery function has been selected, wherein the color of the pulsing light indicates which of the surgery functions has been selected. In some embodiments, audio feedback is also provided as the selection buttons cycle through the menus of functions available (such as a synthesized or recorded voice or a set of distinctive tones that announces which function has been selected).

FIG. 1B is a table 192 showing the function-selection state machine changes obtained by successive presses of an optical-stimulation function-selection button 108 (FIG. 1A) or 127 (FIG. 1C) according to some embodiments of the present invention, wherein in an initial state no stimulation function is selected (i.e., when activation button 117 is pressed when the function selector controlled by button 127 is in its initial state, no optical stimulation signal is sent). After one press of function-selection button 127, a first optical-stimulation function is selected (e.g., when activation button 117 is pressed, the stimulation signal starts, and when activation button 117 is released, the stimulation signal stops, or a pulse 200 of a predetermined temporal length is generated (see FIG. 2A)). After a second press of function-selection button 127, a second optical-stimulation function is selected (e.g., a ramped pulse 202 of a predetermined temporal length is generated (see FIG. 2C) when activation button 117 is pressed). After a third press of function-selection button 127, a third optical-stimulation function is selected (e.g., a repeated pulse train 201 of a predetermined number of pulses and temporal length is generated (see FIG. 2B) when activation button 117 is pressed). After a fourth press of function-selection button 127, a fourth optical-stimulation function is selected (e.g., a varying height or ramped pulse train 203 of a predetermined temporal length is generated (see FIG. 2D) when activation button 117 is pressed). After a fifth press of function-selection button 127, the initial no-operation state is again selected, wherein no stimulation function is selected. Additional presses of function-selection button 127 then again progress through successive states of the function menu.

FIG. 1C is a block diagram of a laser device (handpiece) 141 that uses a manually controlled selector 121 implementing a finger or thumb control. In some embodiments, in lieu of a trigger 108 shown in FIG. 1A, a thumb-and/or-forefinger-controlled activation button 117 that is one element of a control apparatus is used to control the flow of IR and/or visible light. In one embodiment, control signals enter and exit via a single optical-fiber structure 120. In other embodiments, the input signal is sent through fiber 120, and the return control signal is returned via fiber 128. In some embodiments, in contrast to sheath 105 of FIG. 1A, disposable sheath 116 includes one or more disposable (or one or more reusable) optics (such as a lens or holographic imager). This optical-fiber structure 120 is operatively connected to a selector 121 that, in turn, is operatively connected to the thumb-and-forefinger control apparatus consisting of activation button 117 and function-selection button 127. This selector 121 controls the amount of IR or visible light exiting the light-emitting optics or lens in ferrule 119 and ultimately the sheath lens or optics 114. In some embodiments, IR-stimulation light and/or visible light is transmitted to the light-emitting optics or lens 119 via one or more optical-fiber structures 118. The light-emitting optics or lens 119 is held in place via a ferrule 122 to which these optics or lenses 119 are operatively coupled. In some embodiments, the ferrule 122, light-emitting optics or lens 119, thumb-and-forefinger-controlled activation button 117 and function-selection button 127, selector 121, and disposable sheath 116 are manufactured from non-metallic, non-magnetic materials such as plastics, polymers, ceramics or the like.

In some embodiments, a source optical signal (e.g., a laser signal) is sent to the function-selection unit 121 of handpiece 140 through optical fiber 120, and the function-selection unit 121 modifies this optical controller signal (e.g., by pulsing it off for a short period of time each time activation button 117 is pressed at a particular function setting that has been established by presses of function-selection button 127, or selectively changing the intensity using, e.g., a neutral-density filter, when activation button 117 is pressed at a different particular function setting that has been established by presses of function-selection button 127), and returning the modified signal, e.g., by reflecting the signal back through the same optical fiber, or by routing it back through a parallel return optical fiber 128. These optical control signals to and from the handpiece 140 allow a user holding handpiece 140 to select and/or activate one or more functions of the optical-nerve-stimulation and/or optical-surgery unit 100 (see FIG. 1A).

In some embodiments, optical-fiber structures 118, 120 and 128 are between 5 and 50 meters in length. The length of the optical-fiber structures 118 and 120 can be determined through empirical testing and/or modeling so as to allow the magnetic or metallic portions of this device to be a safe distance from the magnetic effects of an MRI device.

FIG. 1D is a block diagram of a laser device (handpiece) 142 using a manually controlled selector implementing a finger or thumb control 145 for local mechanical control of the stimulation light. In some embodiments, a shutter 147 is operated by button 146 (in other embodiments, a user-controlled variable iris is provided instead of or in addition to shutter 147). In some embodiments, a turret 144 having a plurality of different lenses (e.g., having different focal lengths, spot sizes, and/or cylinder/astigmatism (to focus to a long narrow spot or line on the nerve), neutral-density filters, holographic imagers or other optics) is rotatable using ratchet-pawl 149 operated by button 148.

FIG. 1E is a block diagram of a laser device (handpiece) 143 having a mister 195 and/or focus plate 194. Handpiece 143 is substantially the same as handpiece 141 of FIG. 1C, but with the addition of a spring-loaded-tip light controller 167, mister 195 having a squeeze bulb 193 containing a sterile saline solution and/or index-of-refraction-matching liquid that is applied by spraying or drops through nozzle 196, either directly onto nerve 69 in tissue 68, and/or onto focus plate 194. In some embodiments, focus plate 194 (made of glass, plastic, or other material transparent to the light wavelengths of interest) is of a thickness such that when lens 114 is pressed on one face and the other face is pressed onto nerve 69, then the light is focussed to a spot size that is desired. In some embodiments, use of focus plate 194 also keeps the nerve moist and alive by preventing evaporation. In some embodiments, mister 195 can be used to apply a moistening liquid or gel onto nerve 69 or onto the nerve-side face and/or outside face of focus plate 194 (besides keeping the nerve moist and alive, this provides an index-of-refraction matching that reduces reflections). In some embodiments, lens 114 is mounted on a spring-loaded selector activation tip 167, such that when the tip 167 is pressed onto a nerve or onto focus plate 194, the stimulation light is activated. In some such embodiments, selector buttons 127 and 117 are omitted, such that the handpiece 143 is selectively activated only when tip 167 is pressed against the subject or other object. In some embodiments, a mechanical shutter (such as shutter 147 of FIG. 1D) replaces selector 161, and is activated to allow light to be emitted when the tip 167 is pressed. In some embodiments, such a spring-loaded tip helps to ensure that the correct focal distance is used.

FIG. 1F is a block diagram of an apparatus that includes an elongated endoscope structure 180 and a nerve-stimulation structure 182. In some embodiments, elongated endoscope structure 180 has an image-obtaining end 185 (e.g., a lens configured to form an image onto a first end of optical-fiber bundle 183) configured to be inserted into a small opening in a subject to enable viewing of an interior tissue of the subject; a first laser diode operable to output a laser beam having a first wavelength, and that is capable of directly stimulating neural tissue of a subject, wherein light of the first wavelength has a first tissue-penetration profile; a fiber holder operable to hold an optical fiber having a first end optically coupled to receive the laser beam from the first laser diode and configured to deliver the laser beam to a second end to stimulate neural tissue of the viewed interior tissue to the subject; and a user-input interface operable to obtain user input and based on the user input, to control application of the first laser beam. In some embodiments, at a second end of optical-fiber bundle 183, a lens is provided for direct viewing of the image on the end of optical-fiber bundle 183, or in other embodiments, a video camera is used to acquire the image for display on a video monitor.

FIG. 1G is a block diagram of a laser device (handpiece) 162 using a spring-loaded-tip controlled selector 167 for local mechanical control of the stimulation light and/or surgical/ therapeutic light. In some embodiments, a ramp on spring-loaded-tip controlled selector 167 slides along the corner of shutter 147, forcing the shutter open when the tip is pressed against something. In some embodiments, a foot-controlled switch or selector (not shown) is activated by the user to select the type of optical signal, and/or to activate or select the timing of the light pulse, such that light is emitted under the control of the user by a selector that is located away from the handpiece and the subject. In some embodiments, both this external selector and the spring-loaded tip must be pressed simultaneously to allow a pulse to be emitted.

In some embodiments of any of the Figures and descriptions herein, a thin transparent membrane 168 (such as plastic surgical tape or sterilized Saran Wrap™) is placed over and/ or in contact with the nerve to keep it from drying out (drying can cause tissue damage and changes the reflectivity to the stimulation light signal). Some embodiments of the invention use a method of stimulating and/or treating nerves that includes covering the nerve with a transparent material (which is either flexible membrane or rigid substrate, or a combination of the two, depending on the embodiment), and delivering an efficacious amount of light through the transparent material. In some embodiments, the transparent material is configured to prevent drying. In some embodiments, the transparent material is configured to ensure a proper focus of the light. In some embodiments, the material is partially transparent, in order to reduce the intensity of the delivered light signal by a predetermined amount. In other embodiments, the material is substantially fully transparent, in order to deliver a maximum amount of light.

FIG. 2A, FIG. 2B, FIG. 2C, and FIG. 2D depict various diagrams 200, 201, 202 and 203 showing a single light pulse, a pulse train, a shaped pulse and a shaped train respectively. In some embodiments, these various types of pulses can be generated via a light-emitting-source controller 104 (alternatively designated a laser controller/power controller 104) operatively coupled to an IR-laser-diode bar 101 via a bus 110 such as that disclosed above. In other embodiments, other pulse forms are used, the efficacies of which are determined through empirical testing and/or modeling.

FIG. 3A is a schematic 300 detailing an implantable version of the device that is powered and controlled via an external source. In some embodiments, an optical stimulator 301 is implanted into a subject (e.g., a patient) to provide an efficacious amount of IR-light stimulation to a nerve fiber. In some embodiments, this optical stimulator 301 contains components including an RF recharger 306, battery 307, controller 308, visible-laser source 309, IR-laser source 310 and combiner 311, with each being operatively coupled to each other such that the RF recharger 306 provides electrical power to the battery 307, which, in turn powers the controller 308. The controller 308 provides electrical power and control signals to the visible-laser source 309 and IR-laser source 310, regulating type and intensity of pulse generated by each of these sources. In some embodiments, the light from these sources (i.e., 309 and 310) is sent to a combiner 311 where the light is combined into a single beam. In some embodiments, the combiner 311 is operatively coupled to an optical-fiber structure 302 that is then positioned such that it can deliver an efficacious amount of IR light to a point of stimulation 303. In some embodiments, this point may be nerve fibers located along the spinal cord, whereas in other embodiments this point of stimulation 303 may be some other group of nerve fibers. As with other embodiments, light from the visible-laser source 309 is used to position the optical-fiber structure 302 relative to a point of stimulation 303. Once the optical-fiber structure 302 is positioned, IR laser light may be applied.

In at least one embodiment, control of the optical stimulator 301 is via a radio remote programmer 304 that sends control signals to the above-described controller 308. In some embodiments, an RF charge source 305 is used to supply electrical power to the optical stimulator 301.

Figure 3B:
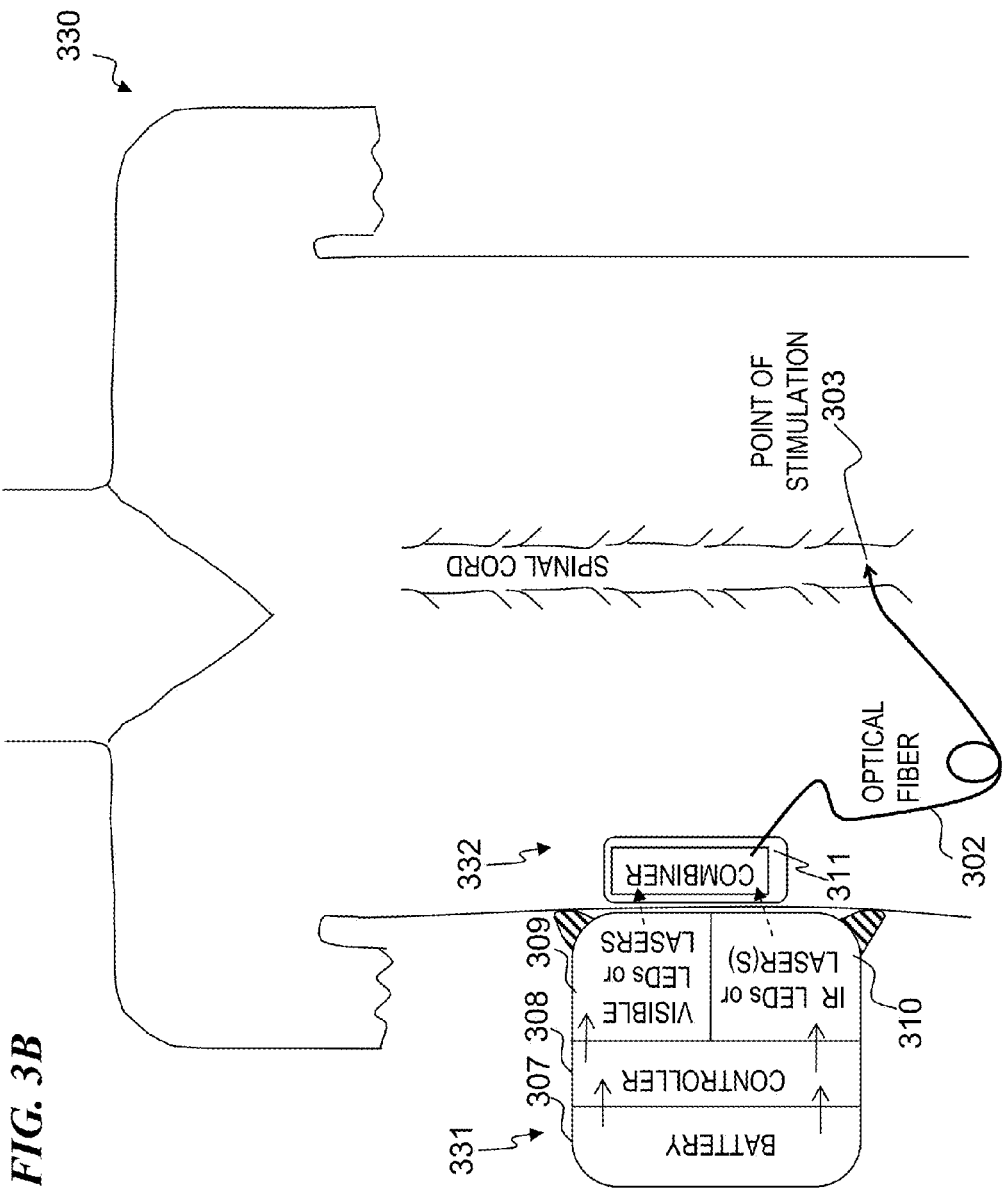
FIG. 3B is a schematic 330 detailing a partially implantable and partially external version of the device.

FIG. 3B is a schematic detailing a partially implantable and partially external version of a device 330 similar in its ultimate function to device 300 of FIG. 3A. In some embodiments, only the combiner 311 and fiber 302 (together forming the implanted portions 332) are implanted (i.e., essentially passive portions of the device), and stimulation light is transmitted transcutaneously from an external unit 331 having the active components, such as battery 307, controller 308, visible-laser source 309, and IR-laser source 310. This allows the active components to be readily serviced, programmed or changed, and to be removed from the subject when not needed. In use, these active external components are pressed against the skin of the subject over combiner 311, which receives the light signals that pass through the skin, and combines the light and delivers it through fiber structure 302 to the one or more internal points of stimulation 303. In some embodiments, fiber structure 302 delivers stimulation or therapeutic light to a plurality of different positions on one or more nerves.

FIG. 4 is a block diagram of a light-delivery device 400 using a manually controlled selector 404 and delivery system 410 of laser light. In some embodiments, delivery system 410 includes a multi-fiber ferrule 405 presenting a plurality of optical-fiber-structure ends 407 closely spaced apart along a line and placed into a delivery head 401. Fiber bundle 406 includes a plurality of fibers that, in some embodiments, are each separately controllable to selectively deliver stimulation light signals to one or more of the plurality of optical-fiber-structure ends 407.

In some cases, for each fiber in bundle 406 a single-emitter diode with a single-mode fiber is used, depending on the nerve size. In some embodiments, the head 401 is placed across a nerve bundle within which the desired nerve of interest is located. Individual optical fibers of fiber bundle 406 are illuminated with stimulation light successively, in order to locate a particular nerve of interest. This allows the user to move the light beam small distances between adjacent nerves without moving the delivery head or having to manually adjust small distances by hand. In some embodiments, a foot control having the same functionality is used in place of button or lever 404 and selector wheel 409, in order that small hand movements (as might be needed to actuate button 404) do not end up moving optical delivery head 401 relative to the nerve bundle.

In some embodiments, nerve-stimulating IR light is emitted from the one or more of the plurality of optical-fiber ends 407 in a successive sequence as controlled, e.g., through the depression of a button or lever 404 by the operator's finger 89, that controls movement of ratcheting selector wheel 409, which interrupts light passing from light-source fiber 417 to light-sensor fiber 418. In some embodiments, light-source fiber 417 and light-sensor fiber 418 are used to control delivery of optical-nerve-stimulation light through the stimulation fiber 406. In some embodiments, the effectiveness of the IR-light stimulation is determined by observing muscle twitches, through the patient (or other subject) reporting a touch or other sensation, or by, for example, observing an fMRI image. In some embodiments, light delivered through fiber bundle 406 is controlled to sequentially scan the light signal 499 across head 401.

In some embodiments, the pattern and speed of scanning is predetermined by a computer program, while in other embodiments the pattern is manually controlled by operator 89. In some embodiments, the computer program controls the emission of stimulation laser light in some type of pattern based upon an algorithm (e.g., a programmed binary search, sequential search, or the like) so as to determine which optical-fiber end 407 delivered an efficacious dose of IR light to the nerve of interest. This allows placement of head 401 across a region of tissue that contains the specific nerve of interest at some unknown position, and then scanning the position of the light output to the different optical-fiber ends 407 to locate the specific nerve without further movement of head 410. In some embodiments, the algorithm includes one or more of the following: optically scanning a plurality of tissue areas, detecting a response of interest, and determining which of the scanned tissue areas, when optically stimulated, causes the response of interest. In some embodiments, the method further includes outputting visible light to point out a physical location of the scanned tissues that caused the response of interest (e.g., shining a laser light out the one fiber end 407 that would illuminate the selected nerve). In some embodiments, the algorithm includes delivering different temporal patterns and/or intensity profiles of one or more light pulses all to a single location, and then repeating this for other locations. In some embodiments, the start and/or progression of the algorithm is operator controlled (e.g., in some embodiments, a finger control such as control mechanism 430 having one or more separately activable mechanisms (e.g., buttons) 404 and one or more light-interrupter wheels 409, connected to respective optical control-signal fibers 417 and 418 of FIG. 4).

The actual reaction or response of nerve tissue to IR-light stimulation would, in some embodiments, be determined through empirical observation (muscle twitches), subject reporting (of a touch sensation, taste sensation, or other sensation), by or some other method known in the art. In some embodiments, the user changes the position and/or function (e.g., changing the pulse length or intensity) of the handpiece on the basis of the response. In other embodiments, the response is detected by the stimulation system, and the function of the stimulation system automatically adjusts the stimulation based on the response feedback (e.g., in some embodiments, a stimulation signal is repeated until the response is detected, and then the stimulation stops and/or an audio or visual indication of the response is output by the stimulation system). The manipulation of the array head itself is facilitated, in, at least one embodiment, through the use of an ergonomically designed handle 412, which is covered by a replaceable, disposable, sterile sheath 411, and by the feedback to the user provided by having visible light delivered to the area that would be stimulated by the IR stimulation signal and/or the other audio and/or visual indications.

In some embodiments, the invention provides an apparatus containing a first light-emitting source, a second light-emitting source, a light-beam combiner, a mechanical linkage with a trigger mechanism, a ferrule, a light-emitting-source controller, and a disposable sheath. In some embodiments, the apparatus includes emitting IR light from the first light-emitting source. In at least one embodiment, the apparatus wherein the second light-emitting source emits visible light. Still, in at least one embodiment, the apparatus wherein the first light-emitting source is operatively coupled to the light-beam combiner via a first optical-fiber structure. In some embodiments, the apparatus wherein the second light-emitting source is operatively coupled to the light-beam combiner via a second optical-fiber structure. In some embodiments, the apparatus wherein the light-beam combiner is operatively coupled to the ferrule via a third optical-fiber structure. In at least one further embodiment, the apparatus wherein the mechanical linkage with a trigger mechanism is operatively coupled to the light-emitting-source controller via an arm. And yet in still one further embodiment, the apparatus wherein the light-emitting-source controller is operatively coupled to the first light-emitting source via a bus.

In some embodiments, light-delivery device 400 also includes light-sensing capabilities in the same head configuration, wherein an optical-nerve-stimulation light signal is sent out one or more of the fibers and a change in the appearance of the nerve or the surrounding tissue is sensed to determine whether or not the correct nerve was selected by the stimulation signal. For example, in some embodiments, a stimulation signal is sent out a first fiber and the fibers on either side are sensed (in the visible, UV and/or IR light spectrum) to determine if the desired response occurred.

In other embodiments, light-delivery device 400 also includes light-sensing capabilities in the same head configuration, wherein an observation light signal (i.e., having one or more selected light frequencies) is sent out one or more of the fibers in bundle 406 (or, in other embodiments, ambient room illumination is used), and the color or the appearance of the nerve or the surrounding tissue is sensed through that fiber end 407 or neighboring optical fibers to determine whether the location of tissue selected by the observation signal was nerve tissue or other tissue based on differences in the color of the reflected light or other sensed. In some embodiments, a visible light is sent out on one or more of the fibers in bundle 406 to illuminate and point out to the surgeon where the nerves are located (one or more of the fiber ends 407 would illuminate just the nerve tissue without illuminating other tissue).

Figure 5:
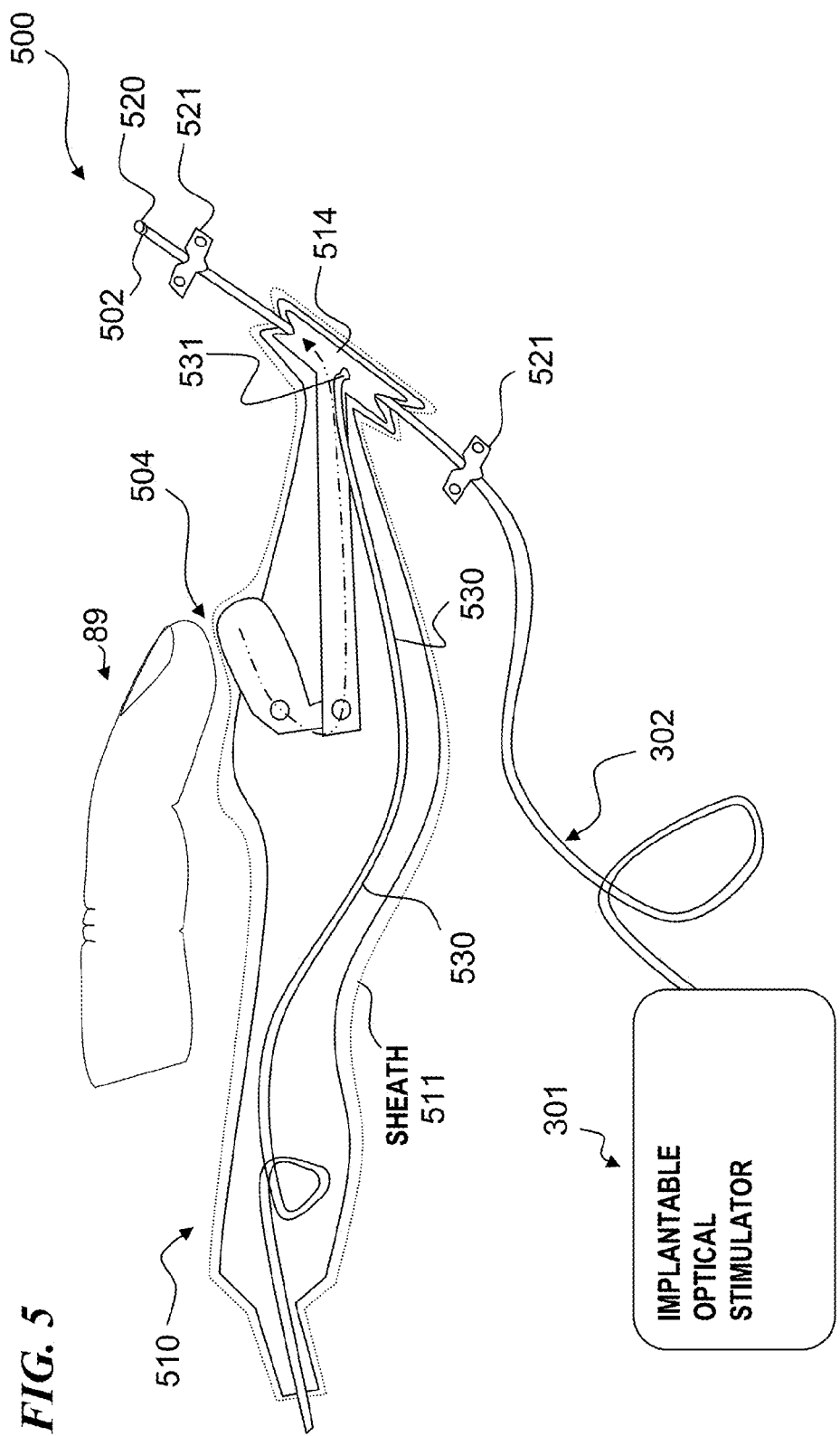
FIG. 5 is a block diagram of a light-delivery device 500 using a manually controlled fiber holder and releaser for guiding and implanting fiber for nerve stimulation using laser light.

FIG. 5 is a block diagram of a light-delivery device 500 using a manually controlled fiber-holder-and-releaser 514 for guiding and implanting an optical fiber 302 connected to delivery system 301 for delivery of optical nerve-stimulation signals of laser light. In some embodiments, light-delivery device 500 includes an ergonomically designed pen-like handle 510 covered by an optional replaceable, disposable, sterile sheath 511. In some embodiments, a button 504 releasably holds implantable optical fiber 302 that optionally includes an optic-interface end 520 (such as a tiny lens). In some embodiments, once the proper location for stimulating a nerve of interest (e.g., using any of the above embodiments combined with or along with light-delivery device 500) optical-fiber end 502 will be affixed to that location in the patient, for example, using suture-able tie-downs 521 sutured to the surrounding tissue. Once optical-fiber end 502 is affixed, button 504 is operated to release the fiber 302 from holder 514 and handle 510 is removed. In some embodiments, handle 510 includes its own optical fiber 530 that injects light (such as auxiliary stimulation or visible light for identifying a specific nerve) from its end 531 through the side and into optical fiber 302. This allows leaving just the crucial implantable fiber 302, while removing the surgeon-assist type fiber(s) 530. Some embodiments of the invention combine the functions and features of device 500 with one or more of the embodiments of FIGS. 1-4 above.

Figure 6A:
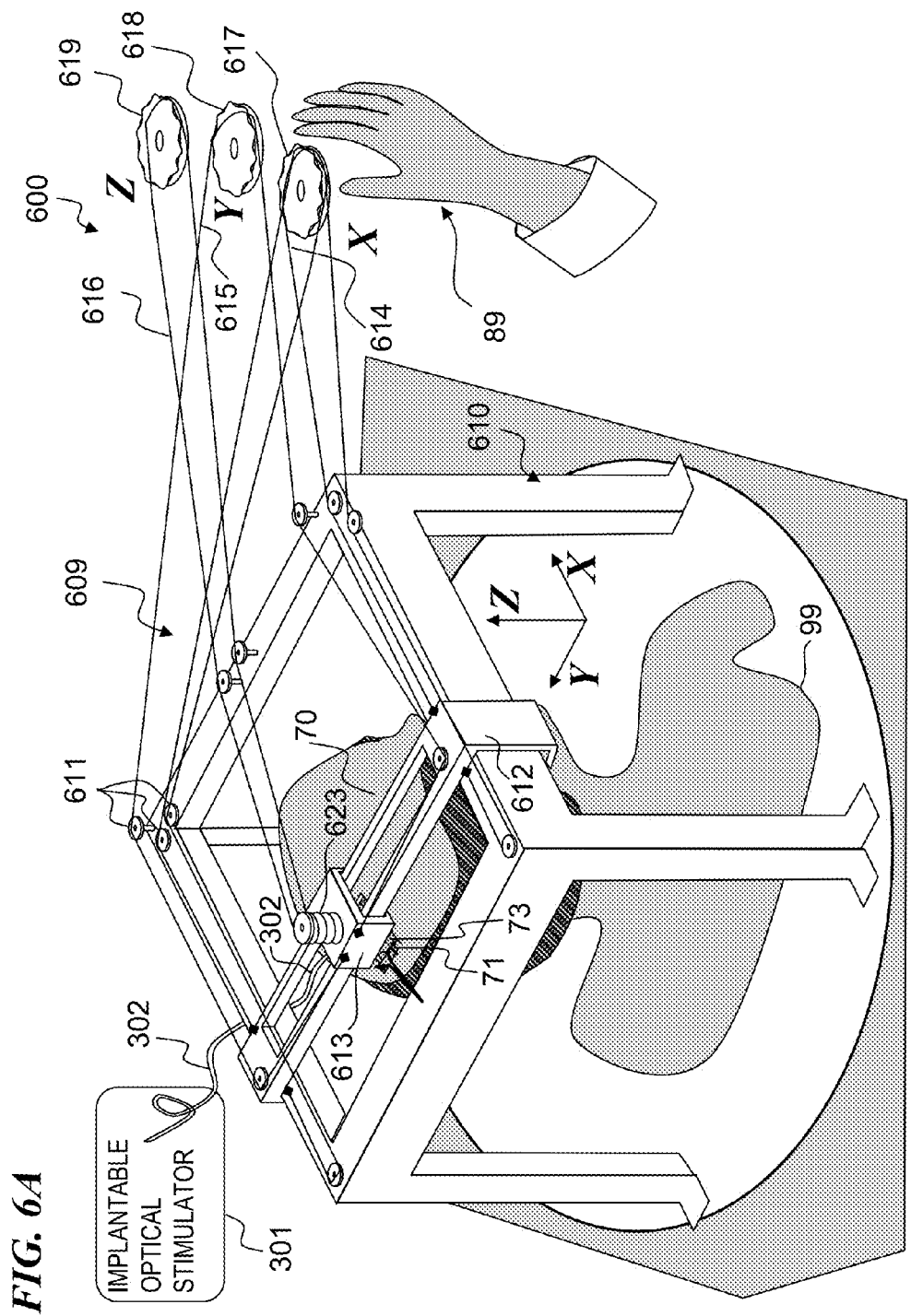
FIG. 6A is a perspective-view block diagram of a light-delivery device 600 using a remotely controlled frame-and-carriage system 609 for delivery of optical-nerve stimulation laser signals.

FIG. 6A is a perspective-view block diagram of a light-delivery device 600 using a remotely controlled frame-and-carriage system 609 for delivery of optical-nerve stimulation laser signals. In some embodiments, light-delivery device 600 is used for guiding and/or implanting an optical fiber 302 connected to implantable optical stimulation system 301. In some embodiments, a plastic frame 610 is affixed to a patient platform (such as an MRI machine 608) configured to provide a suitable platform for holding and stabilizing the optical fiber 302 as it is positioned and has light passed through it. Frame 610 is of a size to suit the needs of the situation, and in some embodiments, the patient is by-in-large immobilized in station 609 relative to frame 610 to obtain precise control of the position of the stimulation light relative to the area being stimulated. In some embodiments, X-carriage 612 moves the stimulation-delivery head 623 in the X-direction (e.g., front-and-back relative to the patient 99) based on a manual rotation (e.g., by the hand 89 of a user) of the X-control knob 617, which moves plastic cables 614 (e.g., in some embodiments, non-stretch gel-spun polyethylene or Nylon fishing line) around pulleys 611 suitably situated. In some embodiments, Y-carriage 613 moves the stimulation-delivery head in the Y-direction (e.g., left-and-right relative to the patient 99) based on a manual rotation of the Y-control knob 618, which moves plastic cables 615 around pulleys 611 suitably situated. In some embodiments, threaded stimulation-delivery head 623 moves the stimulation-delivery head in the Z-direction (e.g., towards and away relative to the patient 99) based on a manual rotation of the Z-control knob 619, which moves plastic cables 616 around pulleys 611 suitably situated, and thus rotates threaded stimulation-delivery head 623 towards or away from the patient 99. In some embodiments, Y-carriage 613 also carries optics (e.g., a lens that focuses an image onto a fiber-bundle array that carries the image signal as light to a remotely located CMOS or CCD imager array) to obtain a video or digital image of the surgical site. In the embodiment shown, frame 610 is large enough (e.g., 50 cm along each side of frame 610, in some embodiments) to fit around the patient 99, and is affixed to the surgical table (not shown), and the patient's head is immobilized (e.g., strapped in place) to minimize movement of the surgical site relative to the Y-carriage 613 and the fiber head. In some embodiments, computer-controlled motors (e.g., see motors 667, 668, and 669 of FIG. 6B below) replace the hand-operated knobs 617, 618, and 619 to move the fiber head in the X, Y, and Z-directions. In some embodiments, additional computer-controlled motors and/or hand-operated knobs allow movements in additional degrees of freedom (e.g., pitch and yaw of direction the fiber head is pointing).

In some embodiments, implantable optical stimulation (IOS) system 301 is first implanted under the patient's skin in the upper chest area, and optical fiber 302 is threaded under the skin to the vicinity of the area to be stimulated (e.g., to a brain lesion or epileptic focus) and connected to stimulation-delivery head 623. Manually-operable position controllers 617-619 then move the shuttle and thus the fiber's light-delivery end to each of various locations and optical stimulations are applied, until the desired location is located, whereupon the optical fiber 302 is released from head 623 and fixed in place (e.g., by sutures or other appropriate means). IOS system 301 then applies therapeutic optical stimulation as needed, on an ongoing basis.

Figure 6B:
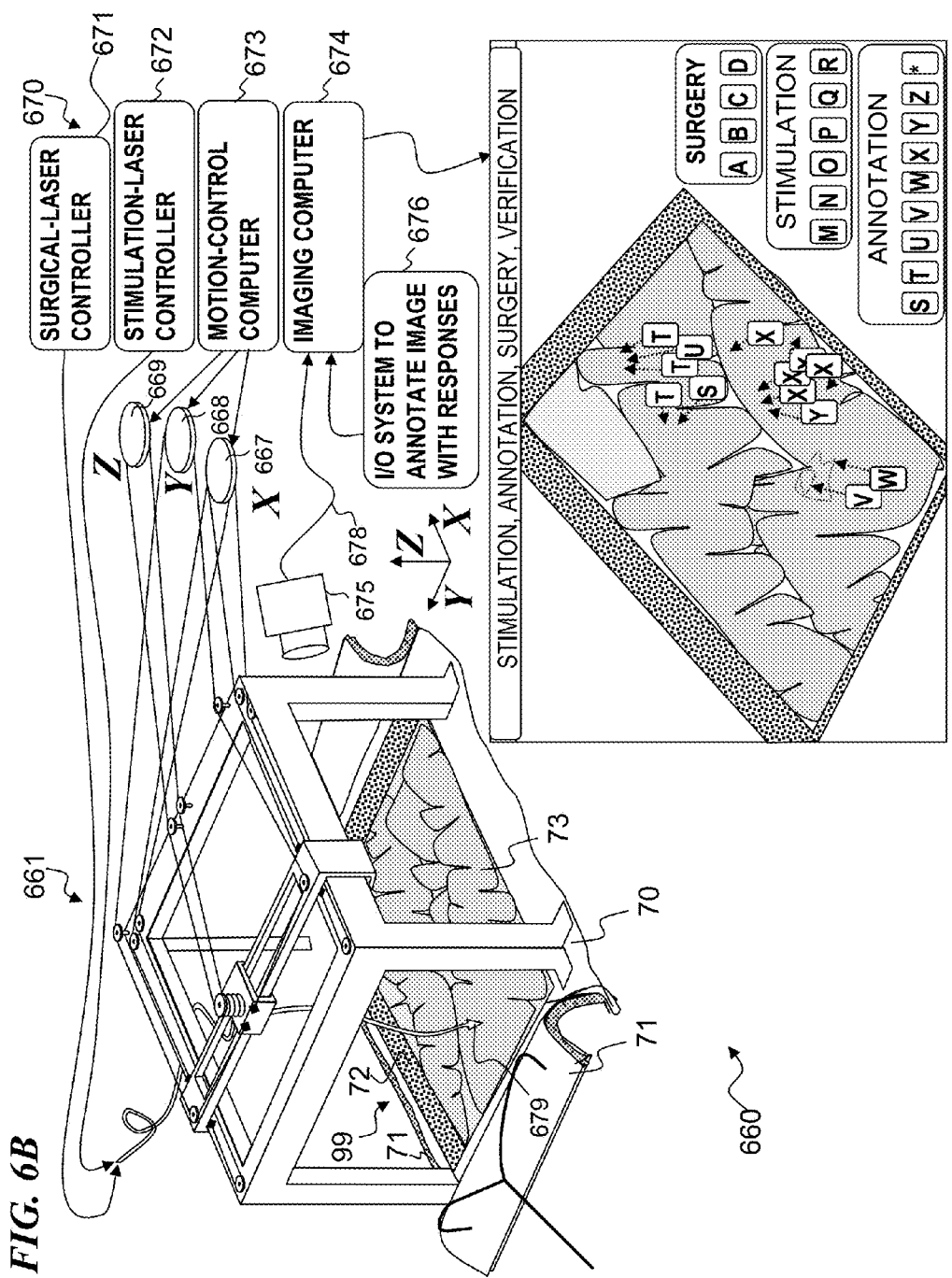
FIG. 6B is a schematic diagram of a computer-aided optical-stimulation and/or optical-surgery device 660, according to some embodiment of the present invention.

FIG. 6B is a schematic diagram of a computer-aided optical-stimulation and/or optical-surgery system 660, according to some embodiments of the present invention. In some embodiments, system 660 includes controller 670 and frame-and-carriage system 661. In the embodiment shown, frame-and-carriage system 661 is identical in operation to frame-and-carriage system 609 of FIG. 6A, except that system 661 is small enough (e.g., 5 cm along each side of frame-and-carriage system 661, in some embodiments) to affix directly to the patient 99. For example, in some embodiments, frame 661 is temporarily screwed to the skull 70 of patient 99, such that the patient's head need not be as immobilized (e.g., strapped in place) for cases where it may be desirable to allow the patient to move her or his head in response to the IR stimulation signal.

In some embodiments, controller 670 includes a laser-surgical-signal controller 671, a laser-stimulation-signal controller 672, a motion-control computer 673, and imaging, display, and annotation computer 674, a display or monitor 671, and an input/output (I/O) system 676, and a digital camera 675. In some embodiments, a non-metallic optical-fiber bundle 678 (e.g., one or more fibers wound in a large circle to form an array of 10,000 or more fibers wound in an, e.g., 5-meter-circumference circular form with an approximate rectangular or square cross-section (e.g., 100 fibers by 100 fibers in 5 mm by 5 mm cross section), and the bundle is then cleaved such that the fibers at each end occupy corresponding positions) and the 5-meter-long bundle is used to carry the image from the surgery site to a remote imaging device such as a CCD (charge-coupled device) or CMOS (complementary metal-oxide-semiconductor) in place of camera 675.

In some embodiments, motion-control computer 673 runs motors 667, 668, 669 and the like to position and point the fiber head 679 at each of a plurality of different locations of the brain 73 of the patient 99. In some embodiments, the skin 71 of the patient's scalp 70 is retracted, and a hole is cut through the skull bone 72 to expose a portion of the brain 73, and frame-and-carriage system 661 is temporarily attached to the skull 72 with screws. The image obtained from camera 677 through fiber bundle 678 is displayed on monitor 675. In some embodiments, a set of software icons (a "toolbox") is visually presented on monitor 675 to allow the user (e.g., surgeon) to control the motion-control computer 673 and the stimulation controller 672. In some embodiments, I/O system 676 includes a mouse, light-pen pointer, joystick and/or voice recognition software for the user to control operations of system 670, and to annotate the image on monitor 675 to indicate the responses obtained from each of the stimulations (e.g., color coding and/or text or icons to indicate each of the responses obtained or sensed). In some embodiments, the user can then indicate the surgical or therapeutic operation to be performed and the spatial extent of the operation, which information is then sent to surgical-laser controller 671 to perform the operation. In some embodiments, the motion programming and stimulation is then again performed to determine the success or extent or response obtained. In some embodiments, the operations of this paragraph are iteratively repeated as needed.

Figure 6D:
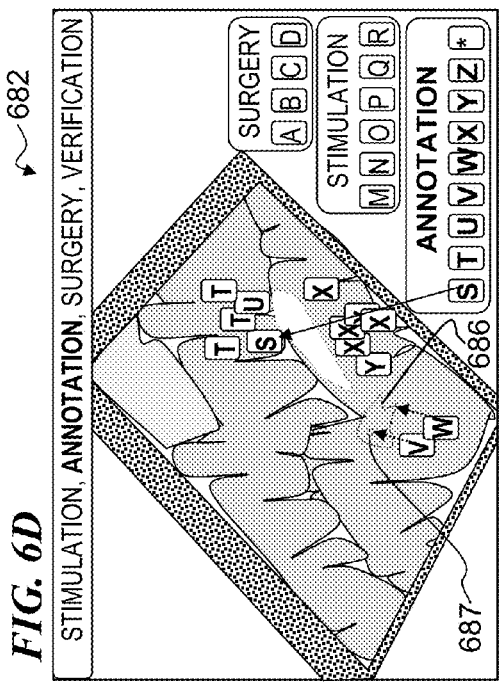
FIG. 6D depicts a screen shot 682 of a display of information from device 660.
Figure 6F:
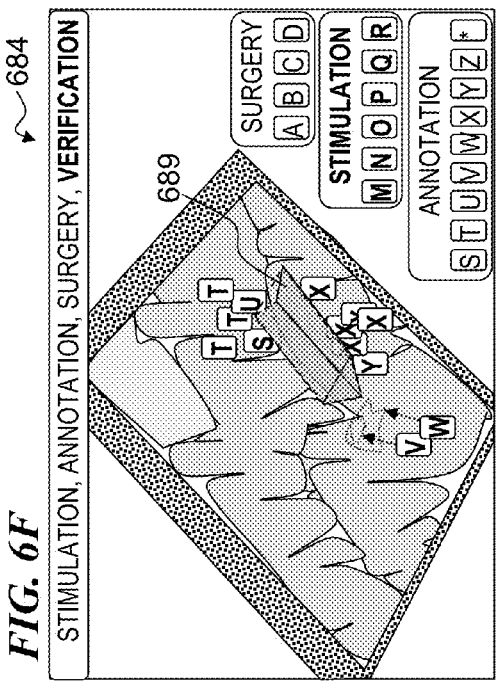
FIG. 6F depicts a screen shot 684 of a display of information from device 660.
Figure 6C:
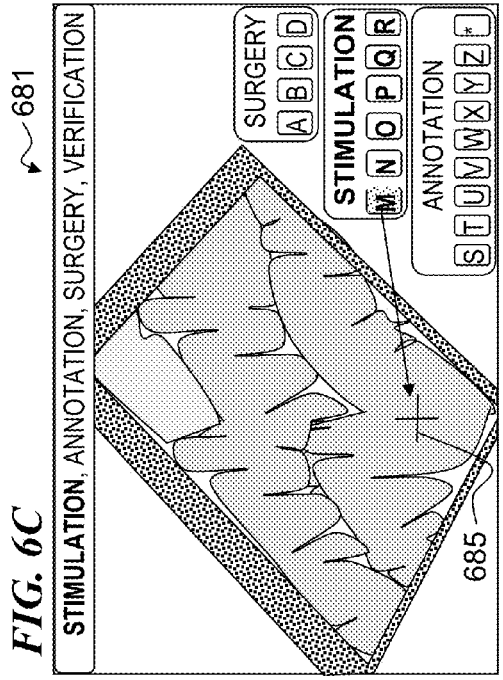
FIG. 6C depicts a screen shot 681 of a display of information from device 660.

FIG. 6C depicts a screen shot 681 of a display of information from computer-aided optical-stimulation and/or optical-surgery system 660 of FIG. 6B. At this point, a starting screen is shown having an image of the surgical site on the subject 99 (e.g., showing an exposed portion of the subject's brain through an opening in the skull). Also on this screen are one or more toolbars and/or drop-down menus that allow a user to stimulate areas of the brain (e.g., using one or more different stimulation light wavelengths, intensities, pulse widths, pulse trains, shapes of pulse intensity, and the like), annotate the image, and control other functions of system 660, as well as to record to a storage medium various images of the operation for documentation and later review. For example, at this point, the STIMULATION toolbar is highlighted to show that various functions (these are denoted M, N, O, P, Q, and R here. but other methods of presenting information and obtaining user input (such as radio buttons, full text, graphical depictions, icons and the like) are used in other embodiments). In some embodiments, a crosshair target 685 is superimposed over the brain image to show the selected position for a stimulation signal to be applied, and an arrow from the selected function (e.g., M) moves dynamically to visually connect the selected function with the point that will be stimulated. In some embodiments, the user can use a mouse or other graphical-user-interface (GUI) input device to move the crosshair target 685 (which then runs motors 667, 668, 669 under control of motion-control computer 673 to move the light-emitting end to stimulate the exact position indicated) and to select the stimulation function. In some embodiments, the imaging computer detects the location of light emitted, and automatically positions the crosshair target 685 to indicate the location on display. In some embodiments, the annotation information is displayed to the side, with a leader line connecting the annotation to the points of stimulation and response. This allows the computer system to "remember" and keep track of each stimulation location (along with an annotation of the response obtained) over a period of time while the surgeon performs other duties and stimulates other areas to form a complete function map of the exposed brain area, in order that the surgeon can go back later to perform surgery, therapy, or additional stimulation.

In some embodiments, once the opening surgery is performed and system 660 is attached in place, most or all of the subsequent operation is done through the computer interface. In some embodiments, this allows an experienced surgeon to perform much of the surgery either from across the room or from a geographically remote location, for example, connected from a remote computer workstation by an internet connection that transmits image information to the remote location and control information to the local portion of system 660.

FIG. 6D depicts a screen shot 682 of a display of information from system 660, showing one exemplary annotation result. For example, at this point, the ANNOTATION toolbar is highlighted to show that various functions (these are denoted S, T, U, V, W, X, Y, Z and * here. but in other embodiments, other methods of presenting information and obtaining user input (such as radio buttons, full text, graphical depictions, icons and the like) are used). In some embodiments, outline maps 686 of the areas associated with various groups of response to the light stimulation (e.g., "finger motor control," "arm touch sense," "smell," or "sight") are defined and drawn by the computer under control of the surgeon, as well as much finer annotations 687 of exactly which response was obtained by stimulation of each point (e.g., "knuckle joint flexure of left index finger"). In some embodiments, color coding is used as an indicator. In some embodiments, icons and/or abbreviations are used. In some embodiments, as the mouse pointer is moved over an icon or spot and is clicked, a pop-up description appears providing more information that was stored previously, and this information is hidden again when the mouse pointer moves off that spot.

Figure 6E:
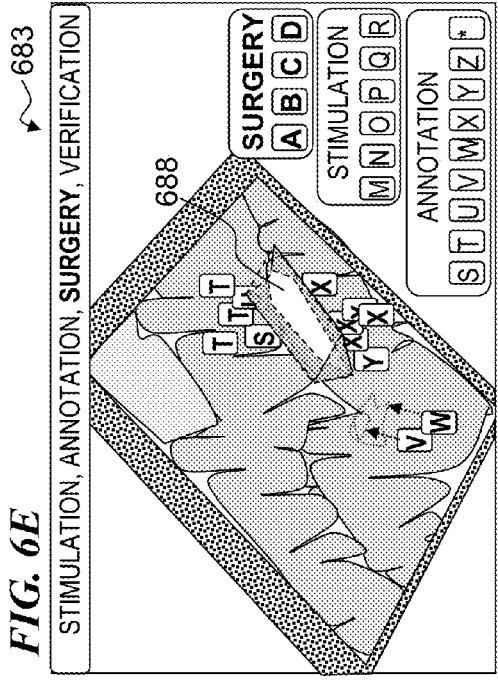
FIG. 6E depicts a screen shot 683 of a display of information from device 660.

FIG. 6E depicts a screen shot 683 of a display of information from system 660, showing one exemplary surgery planning and execution function. For example, at this point, the SURGERY toolbar is highlighted to show that various functions (these are denoted A, B, C and D here. but in other embodiments, other methods of presenting information and obtaining user input (such as radio buttons, full text, graphical depictions, icons and the like) are used). In some embodiments, once the generalized outline maps of the areas associated with various groups of response and/or the detailed functional maps have been generated, the surgeon uses her or his input device (such as a mouse) to define the surgical operation to be performed, and the allowed extent 688 of the surgery, in order that the computerized system 660 can check each subsequent command for whether that portion of the surgery is to be allowed or prohibited (this helps the surgeon "stay within the lines" during an cutting, ablation, or cauterization, for example). In some embodiments, once the extent of the surgery has been delineated, the computer verifies the proposed operation and presents the surgeon with any warnings that may be appropriate for the proposed surgery. In some embodiments, the surgeon can then manually operate the positioning of the light-delivery head and the timing and power to be used for each portion of the cutting, and the computer will enforce the "stay within the lines" definition earlier provided, and will also permit the surgeon to override the limits or redefine the borders and the type of surgery being performed. In some embodiments, the software will also detect certain emergency situations or exigent actions needed, and visually and/or audibly notify the surgeon of the exigency and of the proposed corrective measures that can be applied, and/or can perform the corrective measures automatically under computer control, such that those responses can be preprogrammed and checked under quiet and diligent consideration before the emergency arises.

FIG. 6F depicts a screen shot 684 of a display of information from system 660 once a portion of surgery has been completed. For example, at this point, the VERIFICATION/STIMULATION toolbar is highlighted to show that various functions (these are denoted M, N, O, P, Q and R here. but other methods of presenting information and obtaining user input (such as radio buttons, full text, graphical depictions, icons and the like) are used in other embodiments). The image now shows the brain with a portion 689 that has been removed by the just-completed surgery, and the stimulation and annotation functions can be repeated to check brain functions and results and to determine whether additional surgery may be needed before concluding the operation.

In some embodiments, an optical-fiber-bundle-coupled video camera is configured to image the area being stimulated, and an interactive graphical user interface program is provided to overlay the image with graphics, color, tinting, and/or textual information to annotate the image of the portion of the brain being stimulated, such that the surgeon can create a visual record of the lesions, functions or responses observed for each portion of the imaged area of the brain. This annotated image assists the surgeon to see where to excise, resection, cauterize, implant radioactive seeds (e.g., for cancer treatment), implant optical fiber(s) (e.g., for treatment of epilepsy or orgasmic dysfunction) and the like.

In some embodiments, the present invention uses a frame-and-carriage system 609 (see FIG. 6A) that includes a plastic X-shuttle (or X-carriage) 612 that moves the optical fiber in the X-direction, a plastic Y-shuttle (or Y-carriage) 613 that moves the optical fiber in the Y-direction, each operated by plastic lines (e.g., non-stretch fishing lines of gel-spun polyethylene, Nylon or other suitable material) 614 and 615, respectively, which are coupled to hand-controls 617 and 618, respectively. Some embodiments also include a Z-direction actuator 623 (e.g., a stimulation-delivery head 623 having a threaded shuttle operated by plastic lines 616 from hand-control 619, in some embodiments). In some embodiments, an operator 89 manually operates hand-controls 617, 618, and/or 619. In other embodiments, a computer-assisted actuator system is used, e.g., wherein computer-controlled rotary servos control rotation of controls 617, 168, and 619. By making frame 610, its pulleys, shuttles, lines, screws, and other parts out of plastic, glass, ceramic or other suitable non-magnetic material, system 600 can be used in an MRI machine or other similar environment, where devices that included a magnetic material would be unsuitable, or in an X-ray machine, where devices that included a metallic material would be unsuitable.

Figure 7A:
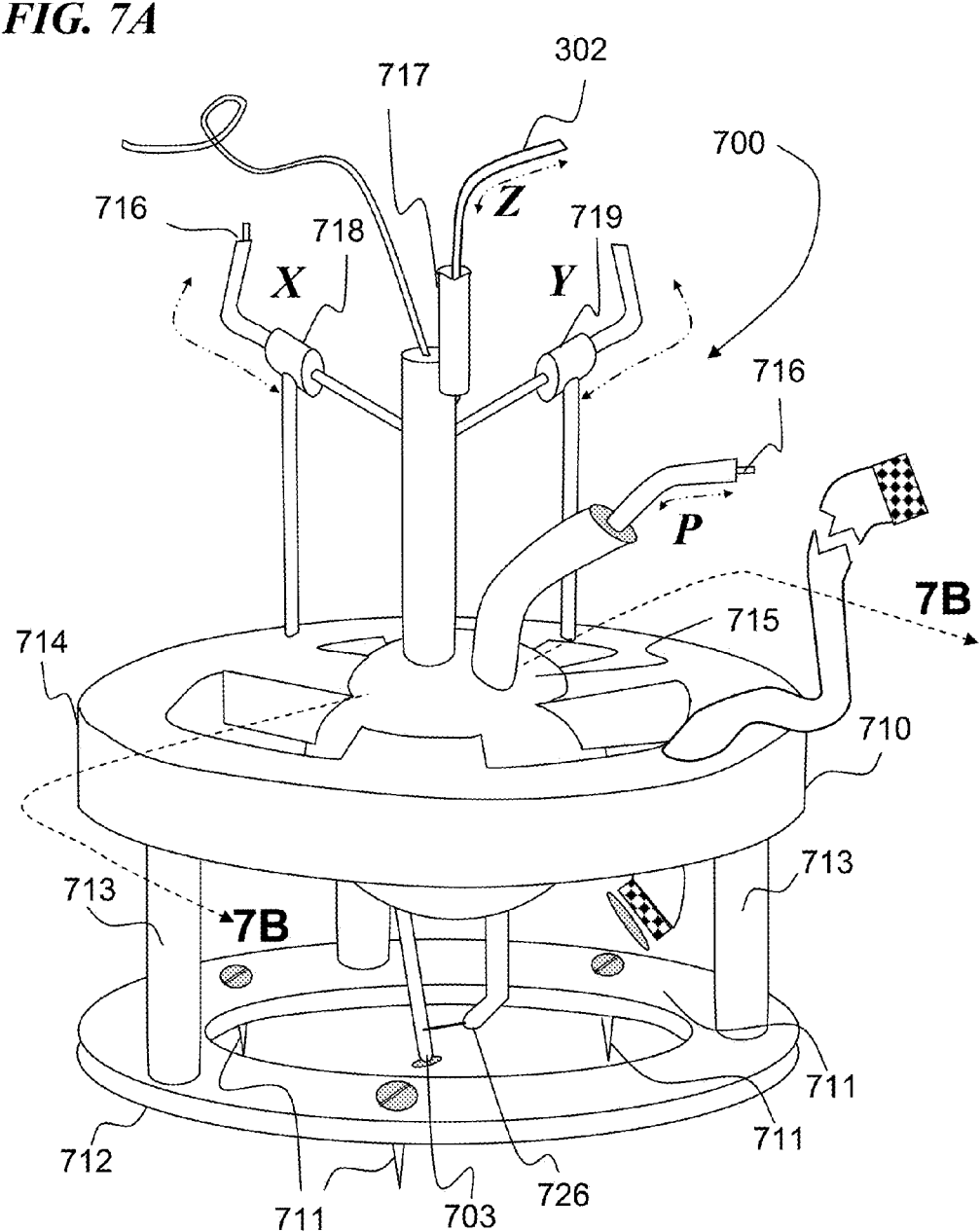

In other embodiments (as shown in FIG. 7A, FIG. 7B, and FIG. 7C, described below), a different small frame 700 is affixed to the patient (e.g., in some embodiments, screwed to the patient's cranium using, for example, plastic (e.g., Nylon™) screws, in order that even if the patient's head moves, the optical fiber does not move relative to the nerve or brain area that light from the fiber is stimulating).

FIG. 7A, FIG. 7B and FIG. 7C are perspective-, side-, and top-view block diagrams, respectively, of a light-delivery device 700 using a remotely controlled fiber holder 710 affixed to a subject 99 for nerve stimulation using laser light. In some embodiments, fiber holder 710 includes a base 712 held to patient 99 using plastic screws 711 (e.g., screwed into the cranium 796 within skin opening 797 around a hole 798 drilled into the cranium 796 to expose the brain 795 where optical stimulation occurs). Posts 713 hold platform 714 above base 712. In some embodiments, platform 714 forms a spherical socket for a ball-and-socket joint to hold spherical ball actuator 715. The top post 725 of spherical ball actuator 715 is moved by X-actuator 718 and Y-actuator 719, that allow control of the X and Y positions of fiber end 703, while Z-actuator 717 allows the fiber end 703 to be moved in the Z-direction and P-actuator 716 (which is connected through actuating end 726 to fiber end 703) allows changing the bending angle of fiber end 703. In some embodiments, additional actuators allow control of additional degrees-of-freedom (e.g., twisting the fiber end 703 to different compass directions). In some embodiments, these four or more actuators include stiff plastic cables within plastic sheaths, to provide push-pull control of position from a distant operator position. In some embodiments, an operator 89 manually operates controls 716, 717, 718, and/or 719. In other embodiments, a computer-assisted actuator system is used.

In some embodiments, an imaging fiber bundle 730 is used with any of the above systems, in particular the embodiments of FIG. 6A or FIG. 6B and FIG. 7B. In some embodiments, imaging fiber bundle 730 includes optics 731 that obtain an image conveyed by fiber bundle 732, in order to obtain imaging to a remote viewing area in a non-magnetic manner. In some embodiments, a video enhancement of the image from the distal end of the fiber bundle 732 is performed and shown on a monitor (such as a liquid-crystal-display (LCD) computer screen). In some embodiments, this image shows the operator 89 where the laser light is directed by imaging the IR laser light (e.g., by a suitable charge-coupled-device (CCD) imager) of the stimulation signal as shown on the patient 99, thus eliminating the need for the visible laser pointer signal.

In some embodiments, a high-power laser is also coupled to the optical fiber (or carried in its own separate fiber), in order to provide a capability for cutting or ablating tissue (e.g., nerve or brain tissue that has been located and identified by the light stimulation signals). This allows the surgeon to stimulate a brain area (or other nerve tissue) to more precisely locate specific regions that are to be saved versus other areas that are to be cut, cauterized or ablated. Thus, a surgeon wanting to excise a tumor or an epileptic focus can better locate and identify, e.g., borders of a lesion and surrounding functional portions of the brain using the optical-fiber-delivered optical stimulation according to the present invention, and then use the optical-fiber-delivered cutting or ablating function.

(In an article in *Epilepsia.* 1991 March-April; 32(2):179-86 titled "Intractable epilepsy and structural lesions of the brain: mapping, resection strategies, and seizure outcome," the authors (Awad I. A., Rosenfeld J., Ahl J., Hahn J. F., and Luders H. of the Department of Neurosurgery, Cleveland Clinic Foundation, OH 44195-5228) noted: "Forty-seven patients with structural brain lesions on neuroimaging studies and partial epilepsy intractable to medical therapy were studied. Prolonged noninvasive interictal and ictal EEG recording was performed, followed by more focused mapping using chronically implanted subdural electrode plates. Surgical procedures included lesion biopsy, maximal lesion excision, and/or resection of zones of epileptogenesis depending on accessibility and involvement of speech or other functional areas. The epileptogenic zone involved exclusively the region adjacent to the structural lesion in 11 patients. It extended beyond the lesion in 18 patients. Eighteen other patients had remote noncontiguous zones of epileptogenesis. Postoperative control of epilepsy was accomplished in 17 of 18 patients (94%) with complete lesion excision regardless of extent of seizure focus excision. Postoperative control of epilepsy was accomplished in 5 of 6 patients (83%) with incomplete lesion excision but complete seizure focus excision and in 12 of 23 patients (52%) with incomplete lesion excision and incomplete focus excision. The extent of lesion resection was strongly associated with surgical outcome either in itself (p less than 0.003), or in combination with focus excision. Focus resection was marginally associated with surgical outcome as a dichotomous variable (p=0.048) and showed a trend toward significance (p=0.07) only as a three-level outcome variable. We conclude that structural lesions are associated with zones of epileptogenesis in neighboring and remote areas of the brain. Maximum resection of the lesion offers the best chance at controlling intractable epilepsy; however, seizure control is achieved in many patients by carefully planned subtotal resection of lesions or foci.")

In some embodiments, the present invention provides a more precise, reliable and efficacious method for such surgery, in that the optical stimulation of nerve and brain tissue can provide more precise results than previous methods (such as the above-mentioned EEG recording followed by mapping using chronically implanted subdural electrode plates), the screwed-on cranial platform can provide a more stable and perhaps precise platform from which to perform excision and/or resections using laser light sufficiently powerful to cut and/or cauterize the relevant tissues. Because of the low mass and relatively high flexibility of optical fibers, they are more readily maneuvered by computer-controlled servos that can be programmed to perform precision surgical procedures as controlled by a surgeon.

Figure 8A:
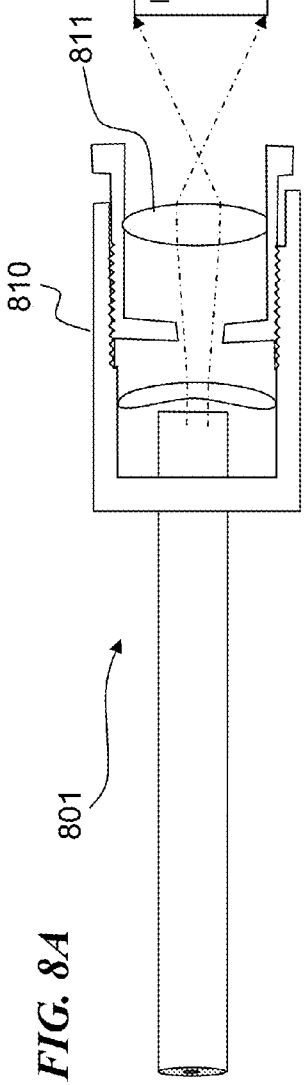
FIG. 8A is a schematic diagram of an optical-fiber light-delivery device 801 using a lens-type imager to direct light over an area.

FIG. 8A is a schematic diagram of an optical fiber light-delivery device 801 using a lens-type imager to direct light from a fiber's delivery end over an area of a nerve or neural tissue. In some embodiments, a replaceable/changeable imaging end 810 having one or more lenses (or, in other embodiments, holographic imagers) 811 is selected to obtain the desired size and shape of the illuminated area that will be irradiated with the IR stimulation signal. The changeable imaging end 810 shown in FIG. 8A is shown with a threaded capsule, however other embodiments use other connection methods, such as, for example, a snap-in fitting. While optical stimulation of a single nerve can be accomplished easily by directing the IR stimulation light to a very small point, when attempting to stimulate brain tissue a larger spot is typically needed. Thus, according to each situation, a spot size suitable for that situation is needed, so having the ability to easily change the imaging end 810 according to the needs of a situation is very helpful. It is also useful for assisting in empirically determining an optimal imaging configuration or spot size.

As used herein, the "launch end" on an optical fiber is not limited to just the fiber's first end, but can also be the point or length along the fiber to which light from a source (such as a laser diode) is coupled to insert the light into the fiber, and the "delivery end" is not limited to just the fiber's second end, but can also be the point or length along the fiber from which light from the fiber is ejected to illuminate and/or stimulate a nerve or neural tissue.

Figure 8B:
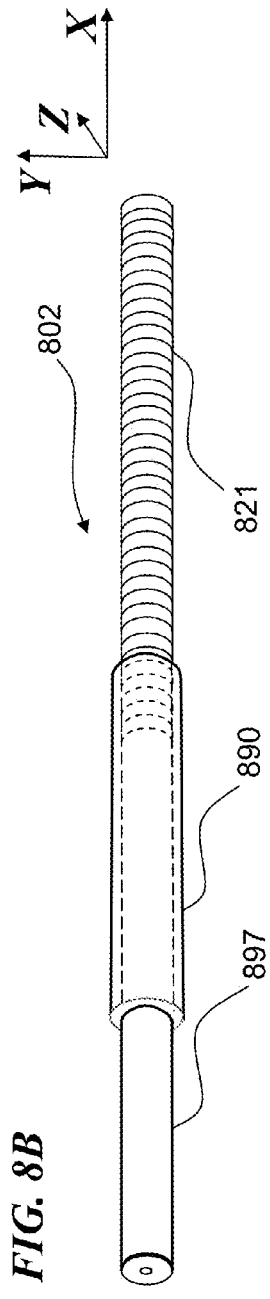
FIG. 8B is a schematic diagram of an optical-fiber light-delivery device 802 using a grating on a fiber to direct light over a line.

FIG. 8B is a schematic diagram of an optical fiber light-delivery device 802 using a grating on a fiber's delivery end to direct light over a line. In some embodiments, fiber 897 has a grating 821 imposed on its end (e.g., by etching, implanting, or other suitable means), wherein grating 821 causes the laser IR stimulation light signal to leak out over the length of grating 821, providing a line of light for nerve stimulation. In some embodiments, an opaque sleeve 890 is movably fitted over a portion of fiber 897 and grating 821, wherein sleeve 890 can be moved lengthwise along fiber 897 to expose a variable portion of grating 821 in order to easily change the length of the line in the X-direction along which light is emitted. Thus, without changing fibers, the length in the X-direction over which light is emitted can easily be changed by sliding sleeve 890 to a position that exposes that length of the grating 821.

Figure 8C:
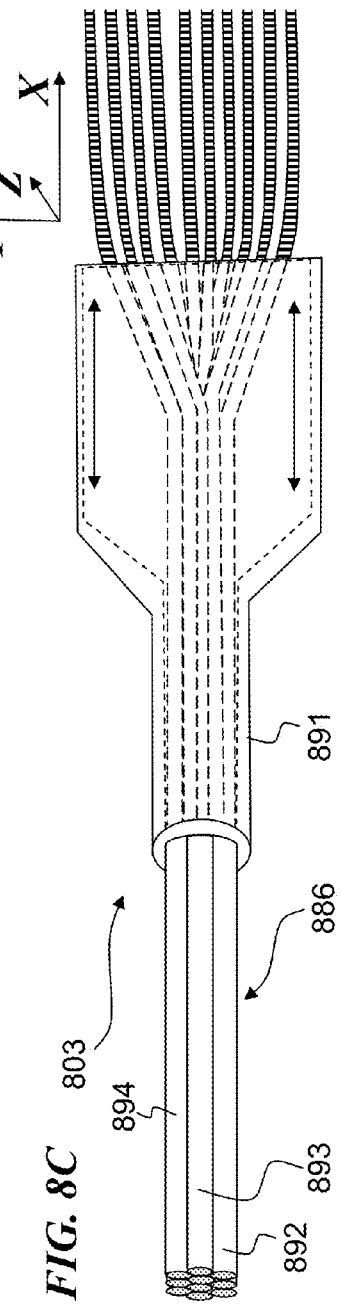
FIG. 8C is a schematic diagram of an optical-fiber light-delivery device 803 using gratings on a plurality of fibers to direct light over an area.

FIG. 8C is a schematic diagram of an optical-fiber light-delivery device 803 using gratings on each one of a plurality of fibers to direct light over an area. In some embodiments, a bundle of fibers 886 is provided having a plurality of individual fibers 892, 893, through 894 (in some embodiments, up to 25 or more individual fibers are provided; however, any number of fibers from two fibers up through hundreds or thousands of fibers is contemplated). In some embodiments, a first movable opaque sleeve 891 is provided such that the length in the X-direction over which light is emitted can easily be changed. In some embodiments, a second movable opaque sleeve (not shown) is provided such that the length in the Y-direction over which light is emitted can easily be changed. In some embodiments, each individual fiber 892-894 has light launched into it by one or more individually activable laser diodes, such that the length in the Y-direction over which light is emitted can easily be changed, or such that one or more individual ones of the plurality of individual fibers 892, 893, through 894 can be illuminated to provide one or more selectable extents in the Y-direction to which an optical stimulation signal is sent. In some embodiments, two or more individual laser wavelengths are selectably coupled to the launch end of each fiber, such that the depth in the Z-direction to which light is directed can easily be changed by selecting the one or more wavelengths that penetrate to that depth. When different types of cells or tissues have varying responses that depend on the wavelength of the light used for stimulation, the type of cell or tissue to be stimulated is selectable by choice of appropriate stimulation wavelength (s).

FIG. 9A is a schematic diagram of an optical-fiber light-delivery device 901 using a grating on each of two optical fibers 896 and 897 to direct light over lines (i.e., along a length of nerve) at two locations $X_A$ 77 and $X_B$ 78 along a nerve 79. In some embodiments, either nerve location $X_A$ 77 or nerve location $X_B$ 78 is stimulated by sending a pulse of stimulation light into the launch end of fiber 896 or fiber 897, respectively, and the resulting response for each stimulation is observed (e.g., by watching a muscle twitch), sensed (e.g., by having the patient report the sensation they feel), or imaged (e.g., by using a functional MRI imaging system). In other embodiments, both nerve location $X_A$ 77 and nerve location $X_B$ 78 are successively stimulated by sending a pulse of stimulation light into the launch end of fiber 896 and fiber 897, respectively, at slightly different times (e.g., where the second stimulation pulse is sent at a time corresponding to the speed of the action potential traveling along that nerve at a distance and time delta relative to the first stimulation pulse), and again recording the resulting response for the paired stimulations as above. In yet other embodiments, simultaneous light-stimulation pulses are sent to nerve location $X_A$ 77 and nerve location $X_B$ 78 and the response is observed and/or recorded. As described above for FIG. 8B, in some embodiments, the exposed grating length of the delivery end is variable using a sleeve or other suitable variable aperture.

FIG. 9B is a schematic diagram of an optical-fiber light-delivery device 902 using a polished end on each of two optical fibers 899 and 895 to direct light to points at nerve location $X_A$ 77 and nerve location $X_B$ 78 along a nerve 79. This embodiment is similar to that of FIG. 9A, except that the delivery end of each fiber has the stimulation light exiting from the physical end of the fiber (e.g., a cleaved end), and the delivered light is directed onto and stimulates one respective point along nerve 79. The operation or use of this device is as described above for FIG. 9A.

In some embodiments, action potentials are all-or-none, binary occurrences and therefore are not reinforceable—once an action potential is triggered, it goes to the end of the axon and causes neurotransmitter release into the synaptic cleft. However, if a nerve is cut or damaged by disease, it may be desirable to start an action potential and then restart the action potential beyond the damaged area.

FIG. 9C is a series of timing diagrams of optical energy and/or nerve voltage versus distance X along the nerve in arbitrary units, showing "reinforced" stimulation of an action potential along a nerve, as stimulated at successive times by a device such as device 901 or device 902 described above. At a time $t_0$, an optical stimulation pulse A is sent down a first optical fiber (896 or 895) to nerve location $X_A$ 77 wherein it triggers a response that includes an action potential 920, which begins propagation down the nerve 79. At a slightly later time $t_1$, the action potential 920 has traveled to point $X_1$ 71 along nerve 79. At a still later time $t_2$, the action potential 920 has traveled to point $X_2$ 72 along nerve 79. At a yet later time $t_3$, the action potential 920 has traveled to point $X_3$ 73 along nerve 79. At a yet later time $t_4$, the action potential 920 has traveled to point $X_B$ 78 along nerve 79, and a second light pulse B is sent down a second optical fiber (897 or 899) in a manner that is timed to reinforce (or, in other embodiments, to counteract) the action potential 920 traveling along nerve 79. At a yet later time $t_5$, the reinforced action potential 920 has traveled to point $X_5$ 75 along nerve 79.

FIG. 10 is a schematic diagram of an optical-fiber light-delivery system 1000. In some embodiments, system 1000 includes a handpiece 140 to be held by a user who manually directs and activates the stimulation and/or surgical optical energy. (In other embodiments, a frame-based light-delivery unit such as unit 609 of FIG. 6A or unit 661 of FIG. 6B or unit 700 of FIG. 7A is used.) The optical energy is delivered by one or more optical fibers in optical-fiber structure 109. In some embodiments, one or more optical-stimulation sources 101 emit IR (or light of another suitable wavelength) nerve-stimulation light, which is coupled by light-beam combiner and/or coupler 103 to optical-fiber structure 109. In some embodiments, optical-stimulation sources 101 include one or more infra-red laser diodes emitting light at one or more different wavelengths (e.g., 1.87 microns, 2.2 microns, or other efficacious wavelengths) under control of light-emitting-source controller 104.

In some embodiments, one or more visible-light sources 102 emit visible indicator light (i.e., light having one or more visible wavelengths suitable for indicating to a user where the stimulation light or surgical light will be delivered), which is coupled by light-beam combiner and/or coupler 103 to optical-fiber structure 109. In some embodiments, visible-light sources 102 include one or more visible-light LEDs, incandescent lamps, and/or laser diodes emitting light at one or more different wavelengths (e.g., 0.45-micron blue light (e.g., gallium-indium nitride devices), 0.55-micron green light (e.g., gallium-indium nitride LED or laser-diode devices), 0.63-micron red light (e.g., gallium-arsenide LED or laser-diode devices), or other wavelengths useful for pointing and/or delivering to the user function-state information such as different colors or pulsing characteristics to indicate which function has been selected) under control of light-emitting-source controller 104.

In some embodiments, one or more high-power laser sources 1001 emit high-power laser light (or very short pulse laser light), which is coupled by light-beam combiner and/or coupler 103 to optical-fiber structure 109. In some embodiments, high-power laser sources 1001 include one or more high-power lasers or laser diodes or optically-pumped-fiber lasers emitting light at one or more different wavelengths (e.g., 1.55 microns, or other wavelengths useful for surgical purposes) under control of light-emitting-source controller 104. In some embodiments, the high-power laser light effects a burning or cutting operation where heat results from the laser interaction with the tissue (i.e., absorbing photon energy from the laser light and converting it to heat). This can result in cauterizing the surrounding tissue and reducing bleeding. In other embodiments, the very short pulse laser light (e.g., femtosecond pulses that concentrate power into a very short time period) effects an ablation or tiny explosion that removes tissue with substantially no heating of surrounding tissue.

In some embodiments, a set of machine control instructions (programmable control code to adjust, time, or otherwise control pulse shape, timing, intensity, and the like) is stored on computer-readable medium 1004 (for example, a compact FLASH memory fob, diskette, CDROM, or network connection (e.g., the internet)), which is connectable to control one or more operations or functions of light-emitting-source controller 104.

In some embodiments, an imaging and control computer 1020 provides automated control signals 1025 to light-emitting-source controller 104, wherein the controller 104 controls the timing, pulse characteristics, wavelength, intensity and like characteristics of the light. In some embodiments, a hand-operated manual control 108 includes one or more buttons, or a rotary control or other actuator form, and is manually operable to remotely control one or more functions of light-emitting-source controller 104 via signals 1008 to imagining and control computer 1020. In other embodiments, a separate hand or foot control (not connected to the handpiece) that provides similar functionality is used in place of manual control 108. In some embodiments, one or more sensors 1030 are configured to sense one or more responses of subject 99 to the optical stimulation of the subject's nerve 77 (or other neural tissue). In some embodiments, the signal(s) 1035 from sensor(s) 1030 pass to imaging and control computer 1020 and are used to augment control of light-emitting-source controller 104 (e.g., changing or terminating a stimulation pulse once the desired response is achieved). In some embodiments, automated or programmed control generated by imaging and control computer 1020 augments or modifies the control commands from manual control 108 based on predetermined criteria, in order to prevent erroneous commands or accidental actuations of manual control 108 from doing harm or performing non-allowed procedures.

In some embodiments, imaging and control computer 1020 also obtains images from one or more digital cameras 1021 and/or 1022, and displays the resulting images on display 1024. In some embodiments, one or more input devices 1023 allow a user to annotate the obtained images using tinting, color, overlaid diagrams, and the like to provide a record of the areas stimulated and the resulting responses. For example, various areas of an exposed brain of a patient can be successively stimulated, and the functions indicated by the responses observed or sensations reported can be recorded as color overlays of the image of the brain, and/or an excision or resection can be planned and plotted on the image. In some embodiments, a set of machine control instructions (programmable control code to augment the imaging, annotation, control functions, and the like) is stored on computer-readable medium 1005 (for example, a diskette, CDROM, or network connection (e.g., the internet)), which is connectable to control one or more operations of imaging and control computer 1020.

In some embodiments, one or more of the items labeled herein as "plastic" are implemented using some other non-magnetic material such as ceramic or structured carbon nanotubes, or the like. In other embodiments, one or more of the items labeled herein as "laser diodes" are implemented instead as light-emitting diodes (LEDs) or as optically-pumped solid-state optical amplifiers (e.g., semiconductor laser-like devices that are pumped optically).

In some embodiments, the invention provides a method that includes generating a first laser using a first light-emitting source, generating a second laser using a second light-emitting source, transmitting the first and second laser to a beam-combiner optic using a first optical-fiber cable, transmitting the first and second laser light from the beam-combiner optic to a ferrule using a second optical-fiber cable, emitting the first and second laser light from the ferrule, regulating the first and second laser light using a mechanical linkage operatively coupled to a light-emitting-source controller; and connecting the light-emitting-source controller to the first light-emitting source via a bus. In some embodiments, the method further includes generating IR light from a first light-emitting source. In some embodiments, the method additionally includes generating visible light from a second light-emitting source. In at least one embodiment, this method includes protecting the ferrule and the mechanical linkage via a disposable plastic sheath. In some embodiments, the method includes emitting a single pulse of light via appropriate action of a light-emitting-source controller. In some embodiments, the method further incorporates emitting a pulse train of light via appropriate action of a light-emitting-source controller. In some embodiments, the method includes emitting a shaped pulse of light via appropriate action of a light-emitting-source controller. In still further embodiments, the method includes emitting a shaped train of light via appropriate action of the light-emitting-source controller.

In at least one embodiment, the invention includes an apparatus comprising a finger-and/or-thumb control, a ferrule, a first optical-fiber cable, a second optical-fiber cable, and a disposable sheath. This apparatus is used to deliver an efficacious amount of, in some embodiments, visible and IR light so as to target and stimulate nerve tissue. In some embodiments, the apparatus includes a configuration wherein the first optical-fiber cable is used to send control signals. In some embodiments, the apparatus includes a configuration wherein the second optical-fiber cable is used to send laser light.

In some embodiments, an apparatus is constructed of an optical stimulator, a first optical-fiber cable, an RF charger, and a radio remote programmer. In some embodiments, this optical stimulator is implanted into a recipient to provide an efficacious dose of IR light to promote nerve stimulation. In some embodiments, this optical stimulator includes an RF recharger, a battery, a controller, a first light-emitting source, a second light-emitting source, and a combiner.

In some embodiments, a method is practiced involving charging an RF recharger, supplying a charge to a battery from the RF charger, powering a controller with the battery, powering a first light source, powering a second light source, emitting light from the first light source, emitting light from the second light source, controlling the light from the first and second light sources using a radio remote programmer, combining the light from the first and second light sources via a combiner, and transmitting the combined light via an optical cable to a nerve fiber. In some embodiments, the method includes transmitting IR light via an optical cable to a nerve fiber. In at least one embodiment, the method includes transmitting visible light via an optical cable to a nerve fiber for the purpose of designating a target nerve fiber.

Some embodiments include a kit that includes a first disposable sheath that includes a first optical system configured to focus light into a first predetermined pattern that is efficacious to optically stimulate a nerve. In some embodiments, the kit further includes a second disposable sheath that includes a second optical system configured to focus light into a second predetermined pattern, different than the first, wherein the second optical system is efficacious to optically stimulate a nerve. In some embodiments, the sheath(s) of this kit are configured to fit over a handle such as handle 132 of FIG. 1C, handle 412 of FIG. 4, handle 512 of FIG. 5, or fiber end 703 of FIG. 7B, and provide one or a plurality of different focus patterns (providing different sizes or shapes of focussed light).

In some embodiments, a kit containing various components is included, this kit containing a first light-emitting source, a second light-emitting source, a light-beam combiner, a mechanical linkage with a trigger mechanism, a ferrule, a light-emitting-source controller, and a disposable sheath. Also contained in this kit are the various materials needed to assemble the apparatus.

In some embodiments, the ferrule and the mechanical linkage are covered with a disposable plastic sheath.

In some embodiments, a single pulse of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a pulse train of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a shaped, non-square pulse of light is emitted based on a manual user input (such as the press of a button or the rolling of a wheel) that is coupled mechanically, electrically or optically to the light-emitting-source controller (e.g., a unit that applies electrical power to a laser diode).

In some embodiments, a shaped pulse train of light is emitted based on a manual user input (such as the press of a button or the rolling of a wheel) that is coupled mechanically, electrically or optically to the light-emitting-source controller (e.g., a unit that applies electrical power to a laser diode).

Some embodiments of the present invention include an implantable apparatus that has an optical-light stimulator operable to generate a light signal that will stimulate a nerve, a first optical fiber operatively coupled to receive light from the stimulator and deliver the light to the nerve, a power source operatively coupled to power the stimulator, and a receiver configured to receive programming commands from a wireless remote programmer, in order to selectively control operation of the stimulator based on a set of data that was wirelessly received.

In some embodiments, the apparatus is configured to be implanted in the body of a mammal. In some embodiments, the power source is a battery. In some embodiments, the stimulator further includes an RF recharger operable to receive RF energy and recharge the battery. In some embodiments, the stimulator further includes a first light-emitting source and a second light-emitting source operatively coupled to be controlled by the stimulator. In some embodiments, the stimulator further includes an optical combiner operatively coupled to combine light from the first light-emitting source and the second light-emitting source into an optical fiber.

Some embodiments of the present invention include a method that includes charging a battery using RF energy, powering a controller from the battery, remotely programming the controller, selectively emitting light from a first light source under control of the controller, selectively emitting light from a second light source under control of the controller, combining the light from the first and second light sources, and transmitting the combined light to a nerve.

In some embodiments of this method, the selectively emitting light from the first light source includes emitting IR laser light from a laser diode. In some embodiments, the selectively emitting light from the second light source includes emitting visible light.

Some embodiments of the present invention include a kit that includes a first light-emitting source, a second light-emitting source, a light-beam combiner, a mechanical linkage with a trigger mechanism, a ferrule, a light-emitting-source controller, and a disposable sheath.

Some embodiments of the present invention include an apparatus that includes an optical fiber, an optical-fiber holder operable to optically couple the optical fiber to a nerve, and an optical sensor operable to distinguish nerve tissue from other tissue based on a sensed optical color.

Some embodiments further include one or more additional optical fibers, wherein an illumination light is delivered to the nerve tissue using one or more of the plurality of optical fibers, and the sensed optical color is sensed through one or more of the optical fibers.

Some embodiments of the present invention include a method that includes generating light from a first laser-diode device, the light having a wavelength between about 1.8 microns and about 2.2 microns, and stimulating a nerve with the light. In some embodiments, the light from the first laser-diode device is in a range of between about 1.80 microns and about 1.85 microns, or in a range of between about 1.81 microns and about 1.86 microns, or in a range of between about 1.82 microns and about 1.87 microns, or in a range of between about 1.83 microns and about 1.88 microns, or in a range of between about 1.84 microns and about 1.89 microns, or in a range of between about 1.85 microns and about 1.90 microns, or in a range of between about 1.86 microns and about 1.91 microns, or in a range of between about 1.87 microns and about 1.92 microns, or in a range of between about 1.88 microns and about 1.93 microns, or in a range of between about 1.89 microns and about 1.94 microns, or in a range of between about 1.90 microns and about 1.95 microns, or in a range of between about 1.91 microns and about 1.96 microns, or in a range of between about 1.92 microns and about 1.97 microns, or in a range of between about 1.93 microns and about 1.98 microns, or in a range of between about 1.94 microns and about 1.99 microns, or in a range of between about 1.95 microns and about 2.00 microns, or in a range of between about 1.96 microns and about 2.01 microns, or in a range of between about 1.97 microns and about 2.02 microns, or in a range of between about 1.98 microns and about 2.03 microns, or in a range of between about 1.99 microns and about 2.04 microns, or in a range of between about 2.00 microns and about 2.05 microns, or in a range of between about 2.01 microns and about 2.06 microns, or in a range of between about 2.02 microns and about 2.07 microns, or in a range of between about 2.03 microns and about 2.08 microns, or in a range of between about 2.04 microns and about 2.09 microns, or in a range of between about 2.05 microns and about 2.10 microns, or in a range of between about 2.06 microns and about 2.11 microns, or in a range of between about 2.07 microns and about 2.12 microns, or in a range of between about 2.08 microns and about 2.13 microns, or in a range of between about 2.09 microns and about 2.14 microns, or in a range of between about 2.10 microns and about 2.15 microns, or in a range of between about 2.11 microns and about 2.16 microns, or in a range of between about 2.12 microns and about 2.17 microns, or in a range of between about 2.13 microns and about 2.18 microns, or in a range of between about 2.14 microns and about 2.19 microns, or in a range of between about 2.15 microns and about 2.20 microns, or in a range of between about 2.16 microns and about 2.21 microns, or in a range of between about 2.17 microns and about 2.22 microns, or in a range of between about 2.18 microns and about 2.23 microns, or in a range of between about 2.19 microns and about 2.24 microns, or in a range of between about 2.20 microns and about 2.25 microns.

Some embodiments of the method further include conveying the light from the laser-diode device to the nerve using an optical fiber. In some embodiments, the laser-diode device includes a plurality of emitters, and the method further includes combining the light from at least two of the plurality of emitters into the optical fiber.

Some embodiments of the method further include affixing the optical fiber to a frame fixed in positional relationship relative to a patient. Some embodiments of the method further include remotely controlling a positioning of the light relative to the nerve.

Some embodiments of the present invention include an apparatus that includes a first disposable sheath that includes a first optical system configured to focus light into a first predetermined pattern that is efficacious to optically stimulate a nerve.

Some embodiments are supplied as a kit that further includes a second disposable sheath that includes a second optical system configured to focus light into a second predetermined pattern, different than the first, which is efficacious to optically stimulate a nerve.

Some embodiments of the present invention include an apparatus that includes a first light-emitting source operative to emit an optical signal at a first wavelength that is capable of directly stimulating a nerve of a patient; an optical-fiber structure having a first end and a second end; a light-beam coupler that is configured to direct light from the first light-emitting source into the first end of the optical-fiber structure; a light-emitting-source controller operatively coupled to the first light-emitting source and the second light-emitting source to selectively control light output thereof; and a light-delivery unit operatively coupled to the second end of the optical-fiber structure, wherein the light-delivery unit, the optical-fiber structure or both the light-delivery unit and the optical-fiber structure are configured to direct the optical signal onto neural tissue.

In some embodiments, the first light-emitting source emits infra-red (IR) light from a laser diode.

Some embodiments further include a second light-emitting source operative to emit an optical signal at a second wavelength that is capable of directly stimulating a nerve, wherein the second wavelength is different than the first wavelength and has a different penetration depth into a given tissue, and wherein light at the first wavelength is applied to achieve a first tissue-penetration depth, and light at the second wavelength is applied to achieve a second tissue-penetration depth.

Some embodiments further include a second light-emitting source operative to emit an optical signal at a second wavelength that is capable of directly stimulating a nerve, wherein the second wavelength is different than the first wavelength and has a different penetration depth into a given tissue, and variable amounts of the first and second different wavelengths are applied simultaneously to achieve a tissue-penetration depth that is variable based on the intensities of the first and second wavelengths of light.

Some embodiments further include a third light-emitting source, wherein the third light-emitting source emits visible light, and wherein the light-beam combiner is operatively coupled to direct light from the third light-emitting source into the optical-fiber structure.

In some embodiments, the light-delivery unit includes a handpiece configured to be held by hand during delivery of the nerve stimulation, and the apparatus further includes a disposable sheath configured to cover at least a portion of the handpiece to provide a sterile covering.

Some embodiments further include a user-operable control mechanism operatively coupled to the controller to control a function of the controller, the control mechanism being configured to be operated in conjunction with the handpiece.

In some embodiments, the user-operable control mechanism is mounted on the handpiece, and configured to be hand operated by a user.

In some embodiments, the user-operable control mechanism is mechanically linked to the light-emitting-source controller.

In some embodiments, the light-delivery unit includes a frame configured to be affixed to the patient, and a moveable light-delivery head connected to the frame and configured to be changeably positioned to deliver light to one of a plurality of locations on the patient.

Some embodiments of the present invention include a method that includes obtaining, from a first laser diode, a first laser beam having a first wavelength that is capable of directly stimulating neural tissue; transmitting the first laser beam in an optical-fiber structure; imaging the first laser beam from the optical-fiber structure onto a location on the neural tissue for stimulation of the neural tissue; and obtaining user input and based on the user input, controlling the first laser beam. In some embodiments, the first laser beam has an infra-red (IR) wavelength.

Some embodiments of the method further include obtaining a second laser beam having a second wavelength that is capable of directly stimulating a nerve, wherein the second wavelength is different than the first wavelength and has a different penetration depth into a given tissue; transmitting the second laser beam in the optical-fiber structure; applying light at the first wavelength to achieve a first tissue-penetration depth; and applying light at the second wavelength to achieve a second tissue-penetration depth.

Some embodiments further include obtaining a second laser beam having a second wavelength that is capable of directly stimulating a nerve, wherein the second wavelength is different than the first wavelength and has a different penetration depth into a given tissue; transmitting the second laser beam in the optical-fiber structure; and applying variable amounts of the first and second different wavelengths simultaneously to achieve a tissue-penetration depth that is variable based on the intensities of the first and second wavelengths of light.

Some embodiments further include obtaining a third light beam having a visible-light wavelength; transmitting the third light beam in the optical-fiber structure; and imaging the third light beam from the optical-fiber structure as an indication of where the first laser beam is directed.

Some embodiments further include providing a handpiece for manually directing the location of the imaged stimulation light; and covering at least a portion of the handpiece with a sterile cover.

In some embodiments, the obtaining user input includes coupling a control mechanism to a laser controller to control a function of the controller, wherein the control mechanism is configured to be operated in conjunction with the handpiece.

In some embodiments, the control mechanism is mounted on the handpiece, and the obtaining user input includes coupling a manual operation of the control mechanism by a user to control the first laser beam.

Some embodiments further include providing a handpiece for manually directing the location of the imaged stimulation light, wherein the obtaining user input includes coupling a user-operated control mechanism to a laser controller to control a function of the controller, wherein the control mechanism is separate from the handpiece and is configured to be operated such that operation of the control mechanism is independent of movement of the handpiece.

Some embodiments further include providing a light-delivery unit for directing the location of the imaged stimulation light, wherein the light-delivery unit includes a frame configured to be affixed to the patient, and a moveable light-delivery head connected to the frame; and positioning the light-delivery head to deliver light to one of a plurality of locations on the patient.

Some embodiments of the present invention include an apparatus that includes means for generating a first laser beam having a first wavelength that is capable of directly stimulating neural tissue of a patient, wherein light of the first wavelength has a first tissue-penetration profile; means for transmitting the first laser beam; means for imaging the transmitted first laser beam onto a location on the neural tissue for stimulation of the neural tissue; and means for obtaining user input and based on the user input, controlling the first laser beam.

In some embodiments, the means for generating the first laser beam includes a laser diode and means for controlling electrical power to the laser diode to control timing and intensity of the first laser beam.

Some embodiments further include means for visibly indicating a location on the patient at which nerve stimulation is to be obtained by application of the first laser beam.

Some embodiments further include means for generating a second laser beam having a second wavelength that is capable of directly stimulating neural tissue of a patient, wherein light of the second wavelength has a second tissue-penetration profile different than the first tissue-penetration profile, and wherein the means for generating the second laser beam is optically coupled to the means for imaging.

Some embodiments further include means for generating a third laser beam that is capable of optically cutting tissue, wherein the means for generating the third laser beam is optically coupled to the means for imaging.

In some embodiments, the apparatus is made of materials compatible with use within a magnetic field of an operating magnetic resonance machine.

Some embodiments of the present invention include an apparatus that includes an elongated endoscope structure having an image-obtaining end configured to be inserted into a small opening in a patient to enable viewing of an interior tissue of the patient; a first laser diode operable to output a laser beam having a first wavelength, and that is capable of directly stimulating neural tissue of a patient, wherein light of the first wavelength has a first tissue-penetration profile; a fiber holder operable to hold an optical fiber having a first end optically coupled to receive the laser beam from the first laser diode and configured to deliver the laser beam to a second end to stimulate neural tissue of the viewed interior tissue of the patient; and a user-input interface operable to obtain user input and based on the user input, to control application of the first laser beam.

Some embodiments further include the optical fiber.

In some embodiments, the fiber holder is further configured to implant and release the optical fiber in the patient.

Some embodiments include combinations of elements from different ones of the above-described Figures and specifications. Some embodiments of the invention include a computer-readable medium that has instructions stored thereon for causing a suitably programmed information processor to perform methods that include one or more of the functions or subfunctions described herein.

Some embodiments of the present invention include an apparatus that includes a first light-emitting source operative to emit an optical signal at a first wavelength that is capable of directly stimulating muscle tissue of a subject; an optical-fiber structure having a first end and a second end; a light-beam coupler that is configured to direct light from the first light-emitting source into the first end of the optical fiber structure; a light-emitting-source controller operatively coupled to the first light-emitting source to selectively control light output thereof; and a light-delivery unit operatively coupled to the second end of the optical-fiber structure, wherein the light-delivery unit, the optical fiber structure or both the light-delivery unit and the optical-fiber structure are configured to direct the optical signal onto muscle tissue. In some embodiments, the first light-emitting source emits infra-red (IR) light from a laser diode.

Some embodiments of the muscle stimulator further include a second light-emitting source operative to emit an optical signal at a second wavelength that is capable of directly stimulating muscle tissue, wherein the second wavelength is different than the first wavelength and has a different penetration depth into a given tissue, and wherein light at the first wavelength is applied to achieve a first tissue-penetration depth, and light at the second wavelength is applied to achieve a second tissue-penetration depth.

Some embodiments of the muscle stimulator further include a second light-emitting source operative to emit an optical signal at a second wavelength that is capable of directly stimulating muscle tissue, wherein the first wavelength is different than the second wavelength and has a different penetration depth into a given tissue, and variable amounts of the first and second different wavelengths are applied simultaneously to achieve a tissue-penetration depth that is variable based on the intensities of the first and second wavelengths of light.

Some embodiments of the muscle stimulator further include a third light-emitting source, wherein the third light-emitting source emits visible light, and wherein the light-beam combiner is operatively coupled to direct light from the third light-emitting source into the optical-fiber structure.

In some embodiments of the muscle stimulator, the light-delivery unit includes a handpiece configured to be held by hand during delivery of the muscle tissue stimulation, and the apparatus further includes a disposable sheath configured to cover at least a portion of the handpiece to provide a sterile covering.

Some embodiments of the muscle stimulator further include a user-operable control mechanism operatively coupled to the controller to control a function of the controller, the control mechanism being configured to be operated in conjunction with the handpiece.

In some embodiments of the muscle stimulator, the user-operable control mechanism is mounted on the handpiece, and configured to be hand operated by a user. In some embodiments, the user-operable control mechanism is mechanically linked to the light-emitting-source controller. In some embodiments, the light-delivery unit includes a frame configured to be affixed to the subject, and a moveable light-delivery head connected to the frame and configured to be changeably positioned to deliver light to one of a plurality of locations on the subject.

Another aspect of some embodiments of the invention include a method that includes obtaining, from a first laser diode, a first laser beam having a first wavelength that is capable of directly optically stimulating an action potential in a tissue of an animal; transmitting the first laser beam in an optical-fiber structure; applying the first laser beam from the optical-fiber structure onto a location on the tissue for stimulation of the tissue; and obtaining user input and based on the user input, controlling the first laser beam.

In some embodiments, the first laser beam has an infra-red (IR) wavelength.

In some embodiments, the tissue is muscle tissue, and the action potential is a muscle action potential.

In some embodiments, the tissue is neural tissue, and the action potential is a nerve action potential.

Some embodiments further include obtaining a second laser beam having a second wavelength that is capable of directly stimulating muscle tissue, wherein the second wavelength is different than the first wavelength and has a different penetration depth into a given tissue; transmitting the second laser beam in the optical-fiber structure; applying light at the first wavelength to achieve a first tissue-penetration depth; and applying light at the second wavelength to achieve a second tissue-penetration depth.

Some embodiments further include obtaining a second laser beam having a second wavelength that is capable of directly stimulating muscle tissue, wherein the second wavelength is different than the first wavelength and has a different penetration depth into a given tissue; transmitting the second laser beam in the optical-fiber structure; and applying variable amounts of the first and second different wavelengths simultaneously to achieve a tissue-penetration depth that is variable based on the intensities of the first and second wavelengths of light.

Some embodiments further include obtaining a third light beam having a visible-light wavelength; transmitting the third light beam in the optical-fiber structure; and imaging the third light beam from the optical-fiber structure as an indication of where the first laser beam is directed.

Some embodiments further include providing a handpiece for manually directing the location of the imaged stimulation light; and covering at least a portion of the handpiece with a sterile cover.

In some embodiments, the obtaining user input includes coupling a control mechanism to a laser controller controlling the first laser diode in order to control a function of the controller, wherein the control mechanism is configured to be operated in conjunction with the handpiece.

In some embodiments, the control mechanism is mounted on the handpiece, and wherein the obtaining user input includes coupling a manual operation of the control mechanism by a user to control the first laser beam.

Some embodiments further include providing a handpiece for manually directing the location of imaged stimulation light, wherein the obtaining user input includes coupling a user-operated control mechanism to a laser controller to control a function of the controller, wherein the control mechanism is separate from the handpiece and is configured to be operated such that operation of the control mechanism is independent of movement of the handpiece.

Some embodiments further include providing a light-delivery unit for directing the location of the imaged stimulation light, wherein the light-delivery unit includes a frame configured to be affixed to the subject, and a moveable light-delivery head connected to the frame; and positioning the light-delivery head to deliver light to one of a plurality of locations on the subject.

Some embodiments of the present invention include an apparatus that includes means for generating a first laser beam having a first wavelength that is capable of directly stimulating an action potential in muscle tissue of a subject, wherein light of the first wavelength has a first tissue-penetration profile; means for transmitting the first laser beam; means for imaging the transmitted first laser beam onto a location on the muscle tissue for stimulation of the action potential in the muscle tissue; and means for obtaining user input and based on the user input, controlling the first laser beam.

In some embodiments, the means for generating the first laser beam includes a laser diode and means for controlling electrical power to the laser diode to control timing and intensity of the first laser beam.

Some embodiments further include means for visibly indicating a location on the subject to which optical muscle stimulation is to be obtained by application of the first laser beam.

Some embodiments further include means for generating a second laser beam having a second wavelength that is capable of directly stimulating muscle tissue of a subject, wherein light of the second wavelength has a second tissue-penetration profile different than the first tissue-penetration profile, and wherein the means for generating the second laser beam is optically coupled to the means for imaging.

Some embodiments further include means for generating a third laser beam that is capable of optically cutting tissue, wherein the means for generating the third laser beam is optically coupled to the means for imaging.

In some embodiments, the means are compatible with use within a magnetic field of an operating magnetic resonance imaging (MRI) apparatus.

Some embodiments of the present invention include an apparatus that includes an elongated endoscope structure having an image-obtaining end configured to be inserted into a small opening in a subject to enable viewing of an interior tissue of the subject; a first laser diode operable to output a laser beam having a first wavelength, and that is capable of directly stimulating muscle tissue of a subject, wherein light of the first wavelength has a first tissue-penetration profile; a fiber holder operable to hold an optical fiber, the optical fiber having a first end configured to be optically coupled to receive the laser beam from the first laser diode and configured to deliver the laser beam to a second end to stimulate neural tissue of the viewed interior tissue of the subject; and a user-input interface operable to obtain user input and based on the user input, to control application of the first laser beam. Some embodiments further include the optical fiber.

In some embodiments, the fiber holder is further configured to implant and release the optical fiber in the subject.

In some embodiments, a high-power diode laser array is used for one or more of the light sources used in the above described embodiments. For example, some embodiments use high-power MQW (multiple quantum well) multiple-emitter laser arrays available from Princeton Lightwave Inc., 2555 Route 130 South Suite 1, Cranbury, N.J. 08512, whose laser arrays output laser light with up to 30 watts or more power at 1.45 to 1.55 microns and up to 12 watts or more power at 1.85 microns. In some embodiments, the present invention uses lasers such as described in "218 W quasi-CW operation of 1.83 μm two-dimensional laser diode array" by M. Maiorov et al., Electronics Letters, Vol. 35 No. 8, 15 Apr. 1999. Some embodiments use the structures described for such lasers modified to produce other IR wavelengths. In some embodiments, the present invention uses light sources such as described in U.S. Pat. No. 6,639,930 titled "Multi-level closed loop resonators and method for fabricating same" which issued Oct. 28, 2003; U.S. Pat. No. 6,556,611 titled "Wide stripe distributed Bragg reflector lasers with improved angular and spectral characteristics" which issued Apr. 29, 2003; U.S. Pat. No. 6,459,715 titled "Master-oscillator grating coupled power amplifier with angled amplifier section" which issued Oct. 1, 2002; U.S. Pat. No. 6,417,524 titled "Light emitting semiconductor device" which issued Jul. 9, 2002; U.S. Pat. No. 6,363,188 titled "Mode expander with co-directional grating" which issued Mar. 26, 2002; U.S. Pat. No. 6,339,606 titled "High power semiconductor light source" which issued Jan. 15, 2002; U.S. Pat. No. 6,301,279 titled "Semiconductor diode lasers with thermal sensor control of the active region temperature" which issued Oct. 9, 2001; and U.S. Pat. No. 6,184,542 titled "Superluminescent diode and optical amplifier with extended bandwidth" which issued Feb. 6, 2001; each of which is incorporated by reference.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-En-

What is claimed is:

1. A method comprising:
obtaining, from a first solid-state laser, a first laser beam having a first wavelength that is capable of directly optically stimulating an action potential in a neural tissue of an animal;
transmitting the first laser beam in an optical-fiber structure, wherein the first solid-state laser is a laser diode, and wherein the first laser diode and the optical-fiber structure are operatively coupled to a non-magnetic surgical-instrument handpiece;
applying the first laser beam from the optical-fiber structure onto a location on the tissue for stimulation of the tissue;
obtaining manual user input and when the input is received and based on the user input, controlling the first laser beam to start a series of one or more optical pulses to stimulate an action potential in the neural tissue;
obtaining a second high-power laser beam from a second solid-state laser operatively coupled to the surgical-instrument handpiece; and
performing a cutting operation at the tissue location using the second high-power laser beam.

2. The method of claim 1, wherein the first laser beam has an infra-red (IR) wavelength.

3. The method of claim 1, further comprising:
covering at least a portion of the handpiece with a replaceable sterile cover.

4. The method of claim 1, wherein the obtaining user input includes coupling a control mechanism to a laser controller controlling the first solid-state laser's diode in order to control a function of the controller, and wherein the control mechanism is configured to be operated in conjunction with the handpiece.

5. The method of claim 4, wherein the control mechanism is mounted on the handpiece.

6. The method of claim 1, wherein the obtaining user input includes coupling a user-operated control mechanism to a laser controller to control a function of the controller, and wherein the control mechanism is separate from the handpiece and is configured to be operated such that operation of the control mechanism is independent of movement of the handpiece.

7. The method of claim 1, wherein the obtaining of the user input includes receiving an activation signal from a finger-operated trigger.

8. The method of claim 1, wherein the first laser diode and the optical-fiber structure form part of an elongated endoscope structure having an image-obtaining end configured to be inserted into a small opening in a subject to enable viewing of an interior tissue of the subject, and wherein light of the first wavelength has a first tissue-penetration profile.

9. The method of claim 1, wherein the first laser diode and the optical-fiber structure form part of an elongated endoscope structure having an image-obtaining end configured to be inserted into a small opening in a subject to enable viewing of an interior tissue of the subject, wherein light of the first wavelength has a first tissue-penetration profile, wherein the endoscope structure further comprises an implantable optical fiber, and wherein the method further comprises:
implanting and releasing the optical fiber in the subject.

10. The method of claim 1, wherein the obtaining of user input further includes obtaining user input that specifies a user-specified spatial extent of a surgical operation, and wherein the applying of the first laser beam results in a spatial pattern at the tissue location based on the obtained user-specified spatial extent.

11. The method of claim 10, wherein the obtaining user input further includes coupling a control mechanism to a laser controller controlling the first laser diode in order to control a function of the controller, wherein the control mechanism is mounted on the handpiece.

12. The method of claim 10, further comprising:
coupling a user-operated control mechanism to a laser controller to control a function of the controller, wherein the control mechanism is separate from the handpiece and is configured to be operated such that operation of the control mechanism is independent of movement of the handpiece.

13. A method comprising:
obtaining, from a first solid-state laser, a first laser beam having a first wavelength that is capable of directly optically stimulating an action potential in a neural tissue of an animal, wherein the first laser beam has an infra-red (IR) wavelength;
transmitting the first laser beam in an optical-fiber structure;
applying the first laser beam from the optical-fiber structure onto a location on the tissue for stimulation of the tissue;
obtaining user input and based on the user input, controlling the first laser beam to stimulate an action potential in the neural tissue;
obtaining a second laser beam having a second wavelength that is capable of directly stimulating neural tissue, wherein the second wavelength is different than the first wavelength and has a different penetration depth into a given tissue;
transmitting the second laser beam in the optical-fiber structure;
applying light at the first wavelength to achieve a first tissue-penetration depth; and
applying light at the second wavelength to achieve a second tissue-penetration depth.

14. A method comprising:
obtaining, from a first solid-state laser, a first laser beam having a first wavelength that is capable of directly optically stimulating an action potential in a neural tissue of an animal, wherein the first laser beam has an infra-red (IR) wavelength;
transmitting the first laser beam in an optical-fiber structure;
applying the first laser beam from the optical-fiber structure onto a location on the tissue for stimulation of the tissue;
obtaining user input and based on the user input, controlling the first laser beam to stimulate an action potential in the neural tissue;
obtaining a second laser beam having a second wavelength that is capable of directly stimulating neural tissue, wherein the second wavelength is different than the first wavelength and has a different penetration depth into a given tissue;
transmitting the second laser beam in the optical-fiber structure; and
applying variable amounts of the first and second different wavelengths simultaneously to achieve a tissue-penetration depth that is variable based on the intensities of the first and second wavelengths of light.

15. A method comprising:
obtaining, from a first solid-state laser, a first laser beam having a first wavelength that is capable of directly optically stimulating an action potential in a neural tissue of an animal, wherein the first laser beam has an infra-red (IR) wavelength;
transmitting the first laser beam in an optical-fiber structure;
applying the first laser beam from the optical-fiber structure onto a location on the tissue for stimulation of the tissue;
obtaining manual user input and when the input is received and based on the user input, controlling the first laser beam to start a series of one or more optical pulses to stimulate an action potential in the neural tissue;
obtaining a second light beam having a visible-light wavelength;
transmitting the second light beam in the optical-fiber structure; and
imaging the second light beam from the optical-fiber structure as an indication of where the first laser beam is directed.

16. The method of claim 15, further comprising:
providing a light-delivery unit for directing the first laser beam to the tissue location, wherein the light-delivery unit includes a frame configured to be affixed to the subject, and a moveable light-delivery head connected to the frame; and
positioning the light-delivery head to deliver light to one of a plurality of locations on the subject.

17. The method of claim 15, further comprising:
providing a second laser that is a solid-state laser;
emitting a high-power second laser beam from the second solid-state laser; and
obtaining second user input and based on the second user input, cutting tissue at the tissue location using the high-power second laser beam.

18. The method of claim 15, wherein the first solid-state laser is a laser-diode bar.

19. The method of claim 15, further comprising providing a handpiece for manually directing the first laser beam to the tissue location, wherein the obtaining user input includes coupling a control mechanism to a laser controller controlling the first solid-state laser's diode in order to control a function of the controller, and wherein the control mechanism is configured to be operated in conjunction with the handpiece.

20. The method of claim 15, further comprising providing a handpiece for manually directing the first laser beam to the tissue location, wherein the obtaining user input includes coupling a user-operated control mechanism to a laser controller to control a function of the controller, and wherein the control mechanism is separate from the handpiece and is configured to be operated such that operation of the control mechanism is independent of movement of the handpiece.

21. A method comprising:
obtaining, from a first solid-state laser, a first laser beam having a first wavelength that is capable of directly optically stimulating an action potential in a neural tissue of an animal;
transmitting the first laser beam in an optical-fiber structure;
applying the first laser beam from the optical-fiber structure onto a location on the tissue for stimulation of the tissue;
obtaining manual user input and when the input is received and based on the user input, controlling the first laser beam to start a series of one or more optical pulses to stimulate an action potential in the neural tissue, wherein the obtaining of user input further includes obtaining user input that specifies a user-specified spatial extent of a surgical operation, and wherein the applying of the first laser beam results in a spatial pattern at the tissue location based on the obtained user-specified spatial extent;
providing a light-delivery unit for directing the first laser beam to the tissue location, wherein the light-delivery unit includes a frame configured to be affixed to the subject, and a moveable light-delivery head connected to the frame; and
positioning the light-delivery head to deliver light to one of a plurality of locations on the subject.

* * * * *